United States Patent [19]

Bertoncini

[11] Patent Number: 5,380,437
[45] Date of Patent: Jan. 10, 1995

[54] MULTIFUNCTIONAL FILTRATION APPARATUS

[75] Inventor: Joseph Bertoncini, Darnestown, Md.

[73] Assignee: Biomedical Research And Development Laboratories, Inc., Gaitherburg, Md.

[21] Appl. No.: 12,515

[22] Filed: Feb. 2, 1993

[51] Int. Cl.⁶ .............................................. B01D 29/00
[52] U.S. Cl. ............................... 210/416.1; 73/863.23; 73/863.32; 210/232; 210/258; 210/406; 210/455; 422/101; 435/311
[58] Field of Search ..................... 210/232, 252, 323.1, 210/247, 258, 341, 406, 416.1, 455, 456; 141/8, 65; 73/863.23, 863.32, 863.33, 864.11, 864.35; 422/101, 102, 103, 104; 435/296, 312, 311

[56] References Cited

U.S. PATENT DOCUMENTS

| | | | |
|---|---|---|---|
| 4,167,875 | 9/1979 | Meakin | 210/323.1 |
| 4,600,694 | 7/1986 | Clyde | 435/312 |
| 4,649,967 | 3/1987 | Bruenstein et al. | 141/59 |
| 4,661,458 | 4/1987 | Berry et al. | 435/311 |
| 4,787,988 | 11/1988 | Bertoncini et al. | 210/406 |
| 4,810,471 | 3/1989 | Wachob et al. | 422/101 |
| 4,828,801 | 5/1989 | Lombardy | 422/102 |
| 4,846,970 | 7/1989 | Bertelsen et al. | 210/232 |
| 4,879,431 | 11/1989 | Bertoncini | 435/311 |
| 4,889,812 | 12/1989 | Guinn et al. | 435/313 |
| 4,902,481 | 2/1990 | Clark et al. | 422/101 |
| 4,921,792 | 5/1990 | Trawinski et al. | 435/41 |
| 4,927,604 | 5/1990 | Mathus et al. | 422/101 |
| 4,978,507 | 12/1990 | Levin | 422/100 |
| 5,002,890 | 3/1991 | Morrison | 435/311 |
| 5,009,780 | 4/1991 | Sarrasin | 210/406 |
| 5,057,432 | 10/1991 | Wangersky et al. | 435/289 |
| 5,096,582 | 3/1992 | Lombardi et al. | 210/321.75 |
| 5,108,603 | 4/1992 | Schuette | 210/321.72 |
| 5,108,704 | 4/1992 | Bowers et al. | 422/101 |
| 5,110,556 | 5/1992 | Lyman et al. | 422/101 |
| 5,190,666 | 3/1993 | Bisconte | 210/455 |
| 5,273,718 | 12/1993 | Sköld et al. | 422/101 |
| 5,306,420 | 4/1994 | Bisconte | 210/232 |

Primary Examiner—Sun Uk Kim
Attorney, Agent, or Firm—Breneman & Georges

[57] ABSTRACT

A multifunctional filtration apparatus is provided for the automated transfer, separation and filtration which accommodates all types of filter papers or filter mediums including aerophobic filter mediums such as nitrocellulose, nylon, biological membranes as well as aerophyllic filter mediums. The automated multifunctional filtration apparatus includes a first manifold and one or more separation chambers disposed on one side of a filter medium and a second manifold disposed on the other side of the filter medium. The multifunctional filtration apparatus provides for the high speed transfer, separation of gaseous and liquid components of a fluid before filtration without cross contamination of multiple samples by utilizing the first manifold to transfer fluids containing filtrable substances from test tubes or sample plates to a separation chamber disposed above the filter medium where the gases and liquids are separated and the gases removed before the utilization of the second manifold to provide for the filtration of the filterable substances on the filter medium. Subsequent addition of wash fluids or reagents for further reaction of the filterable substances can also be accomplished utilizing the novel multifunctional filtration apparatus. As a result the automated multifunctional filtration apparatus can be used for all types of filter paper or filter mediums used such as paper, glass, fiber synthetic and traditional filter papers as well as biological membranes or filter mediums having reactive or reactable surfaces for filtering and reacting captured filterable substances.

63 Claims, 34 Drawing Sheets

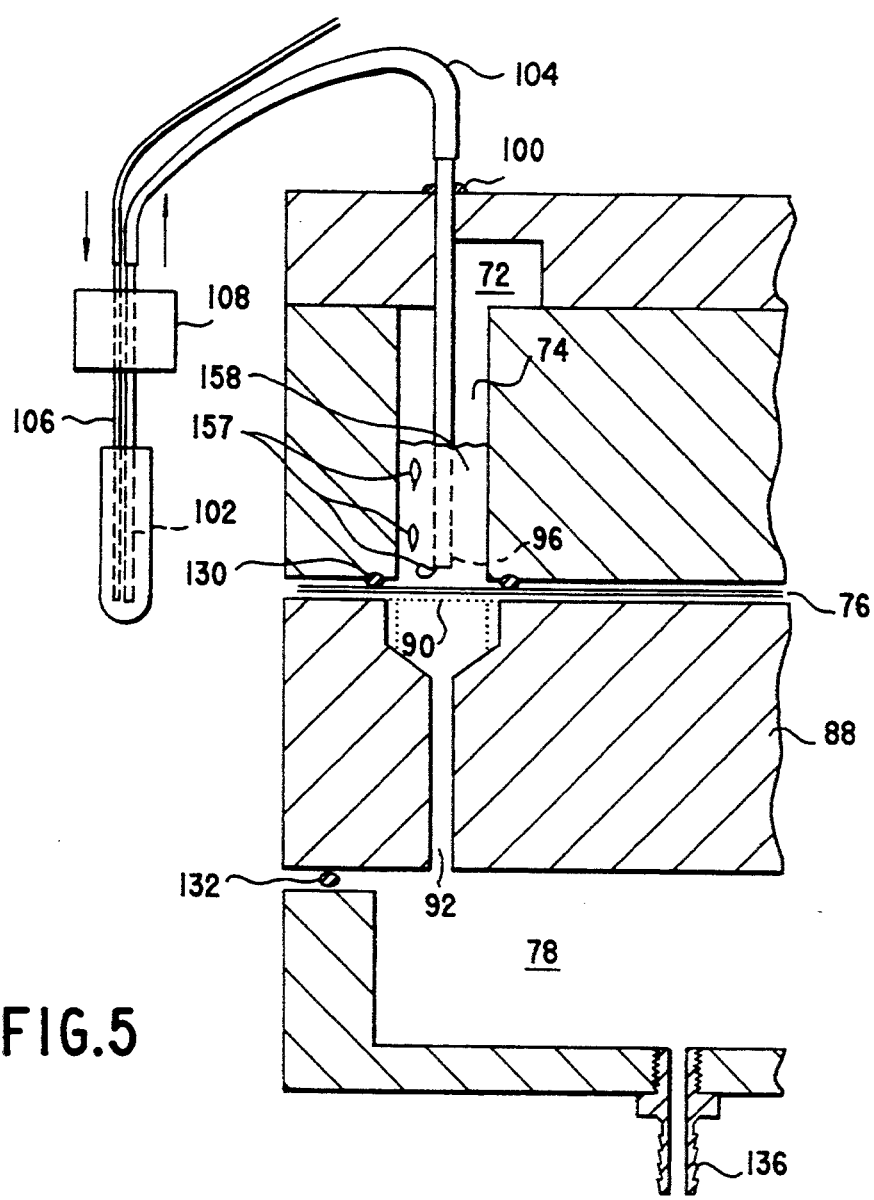
FIG.5
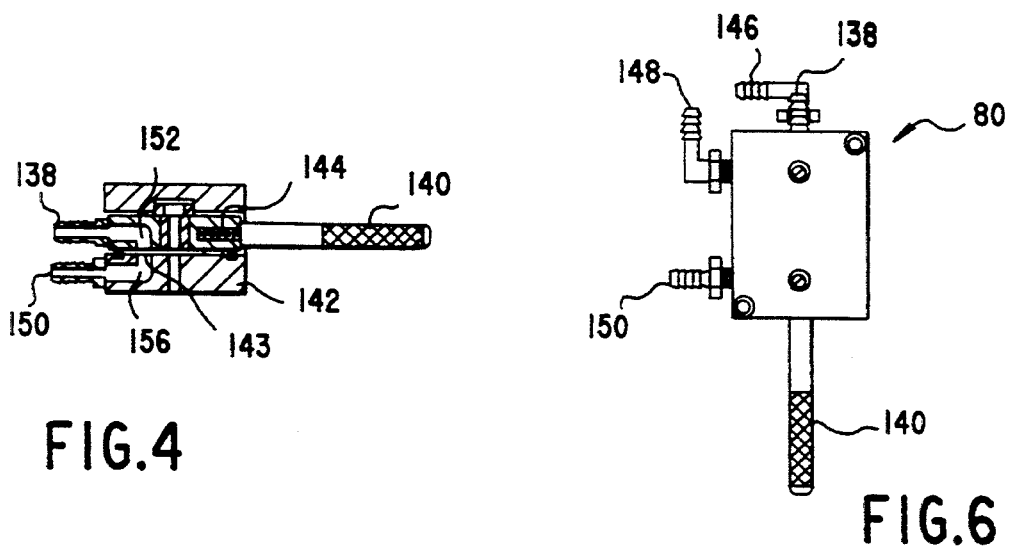
FIG.4
FIG.6

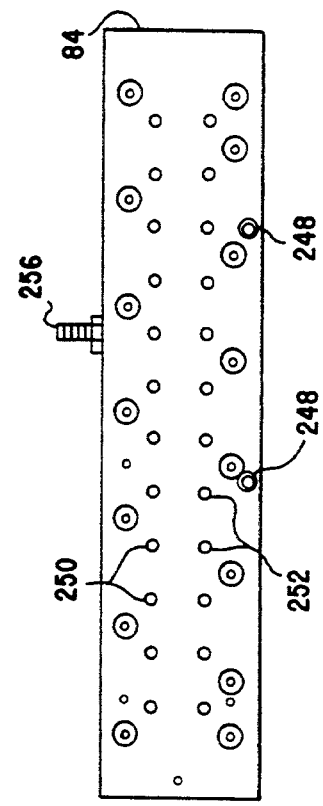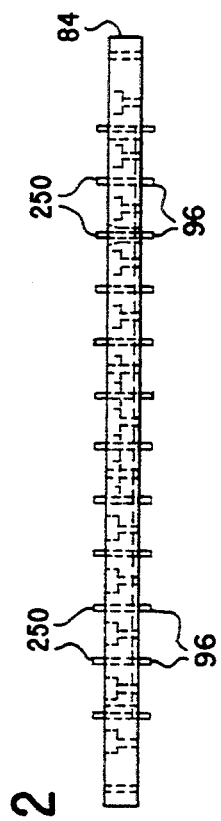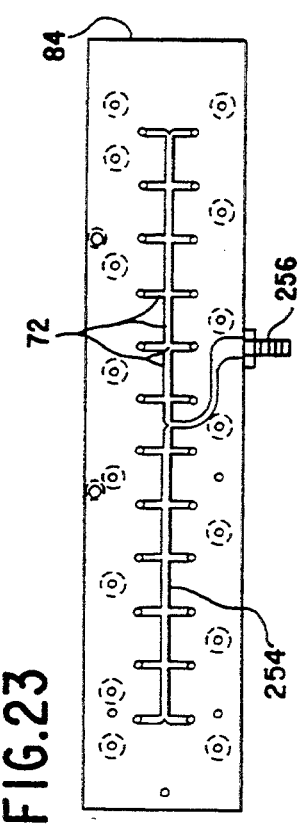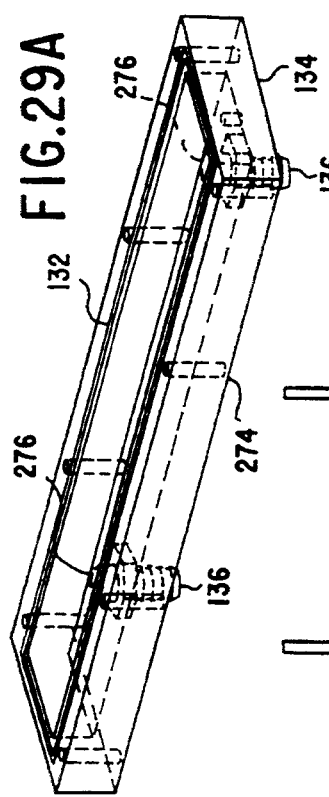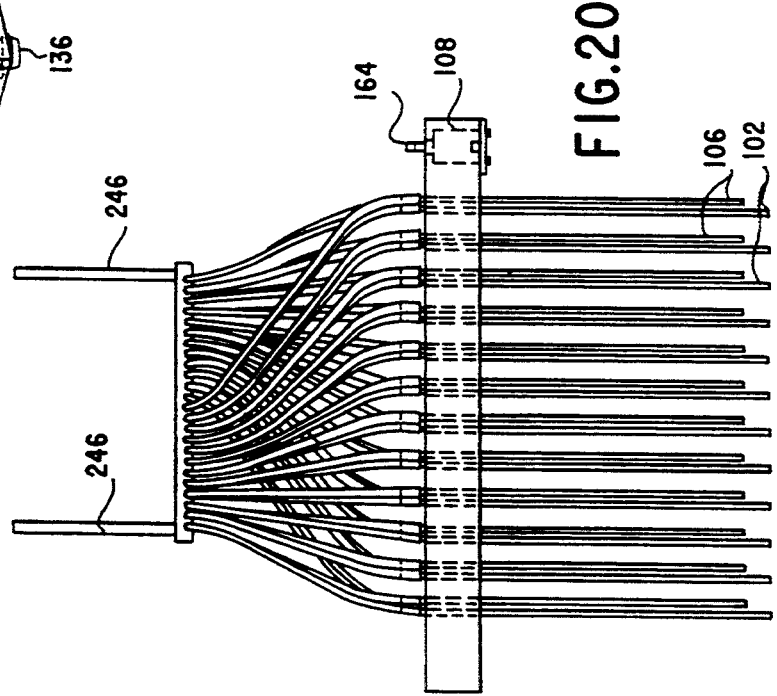

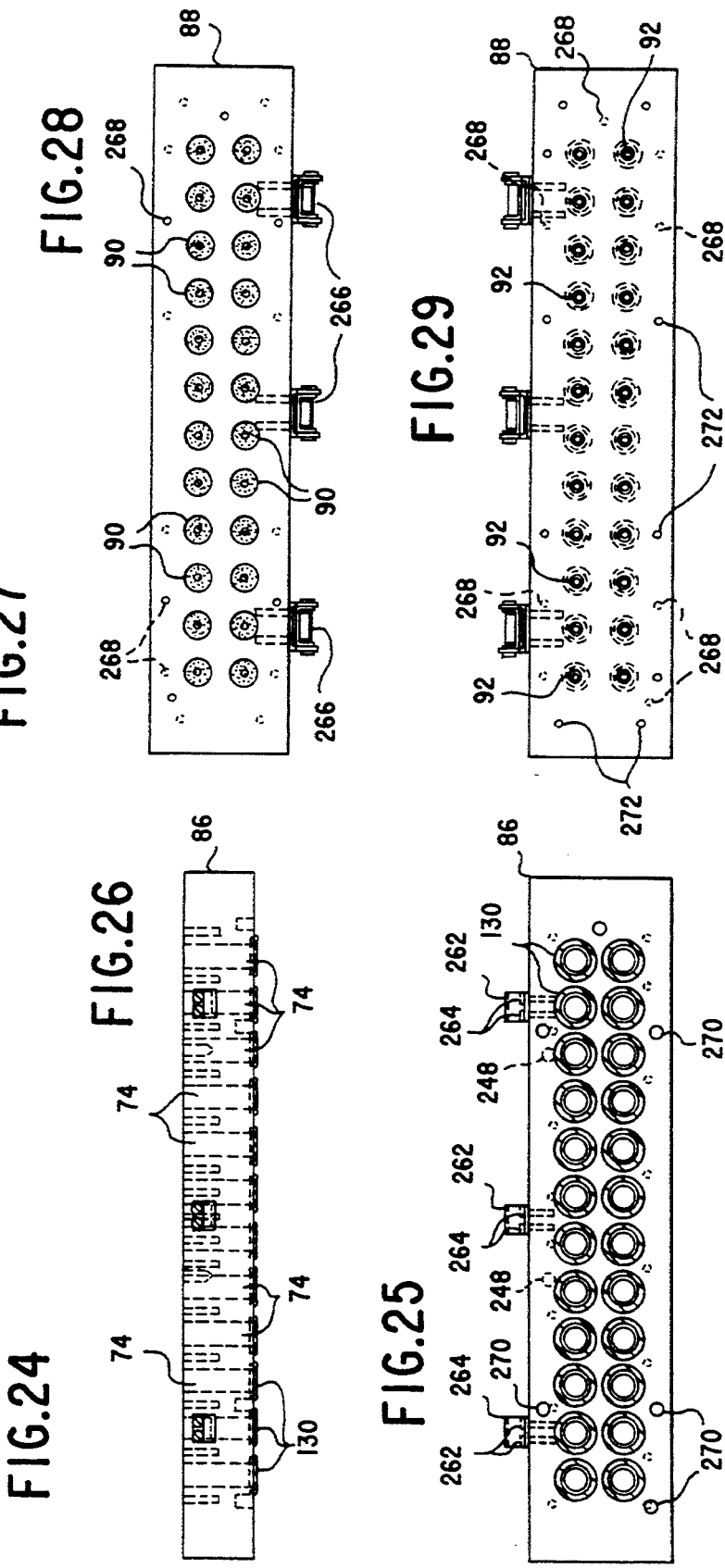

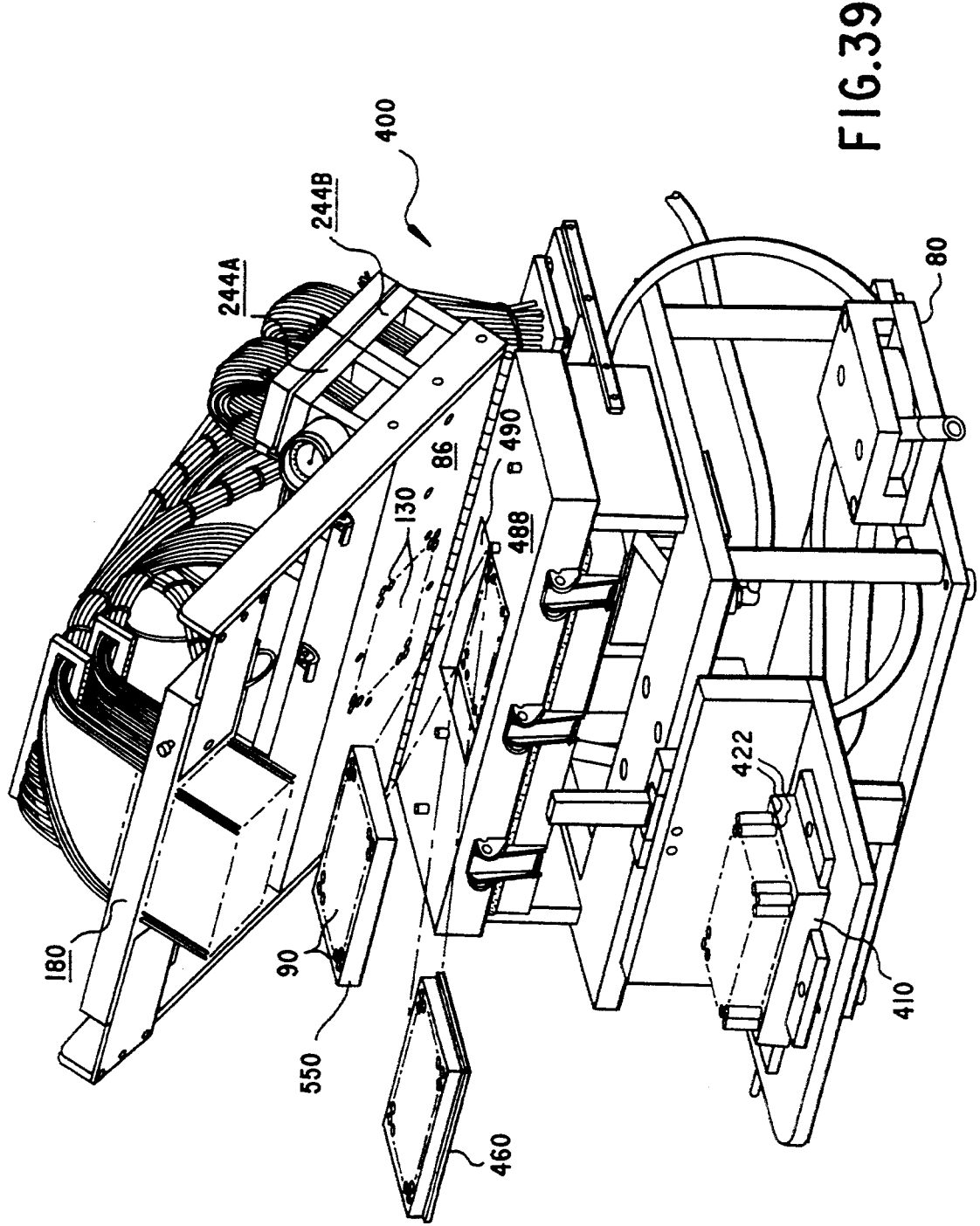

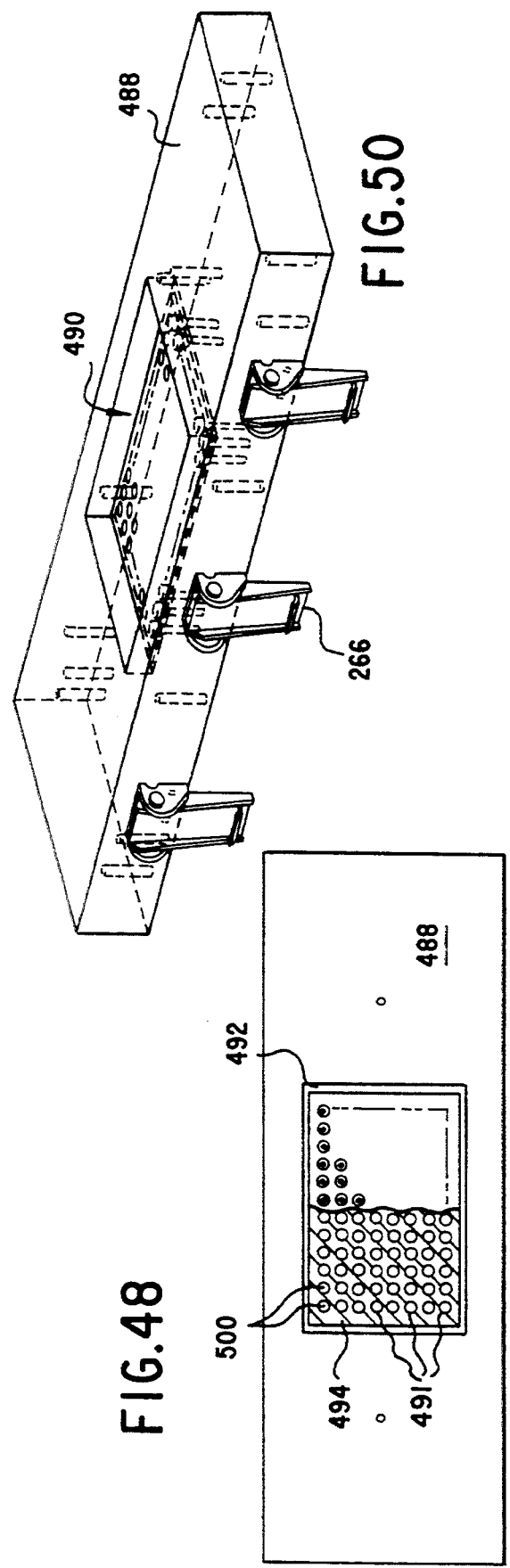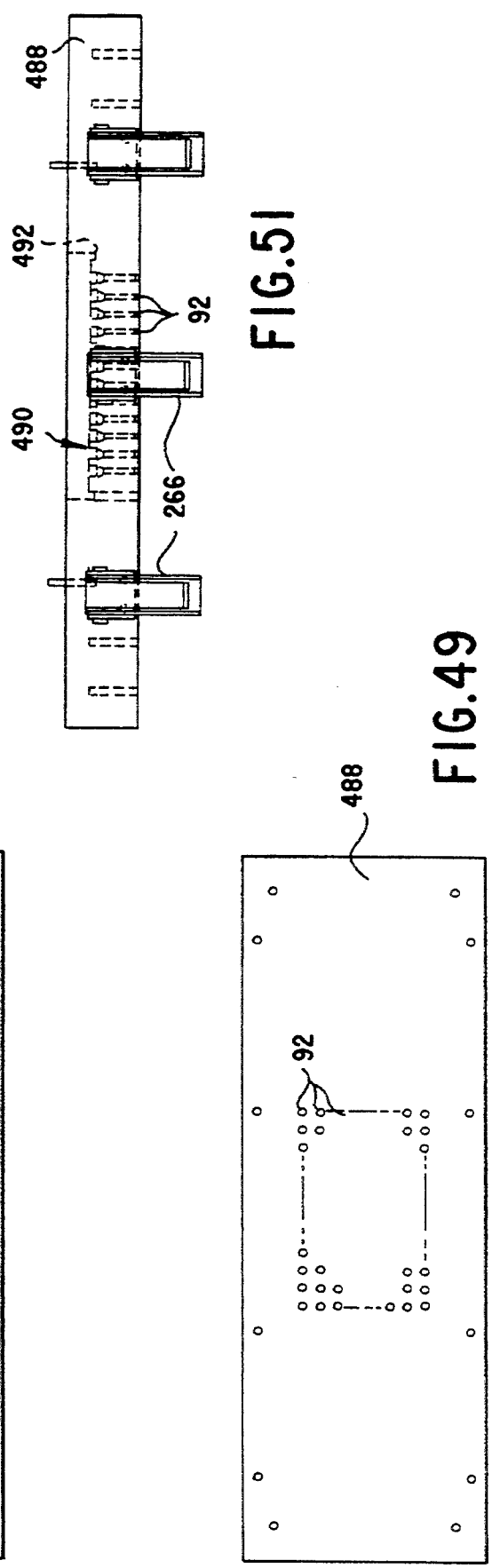

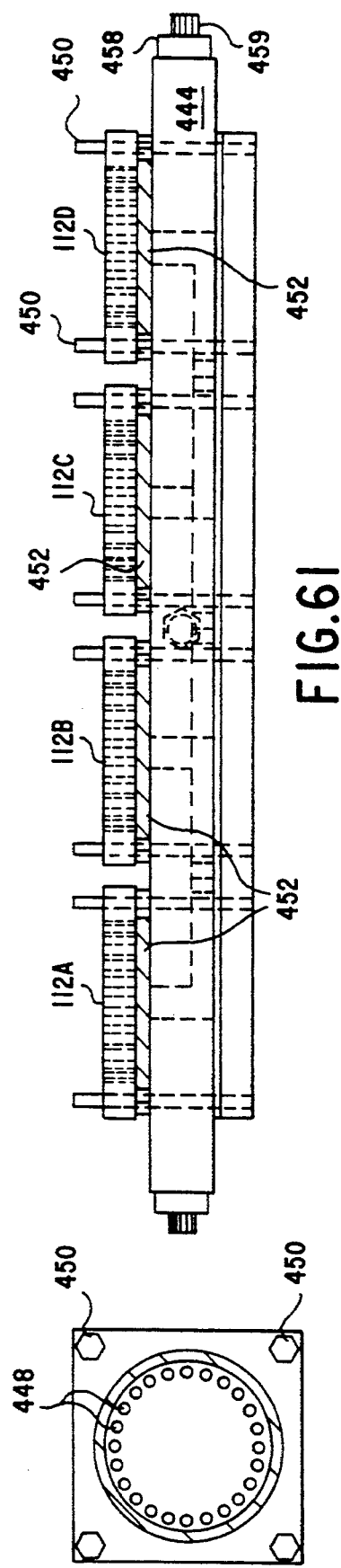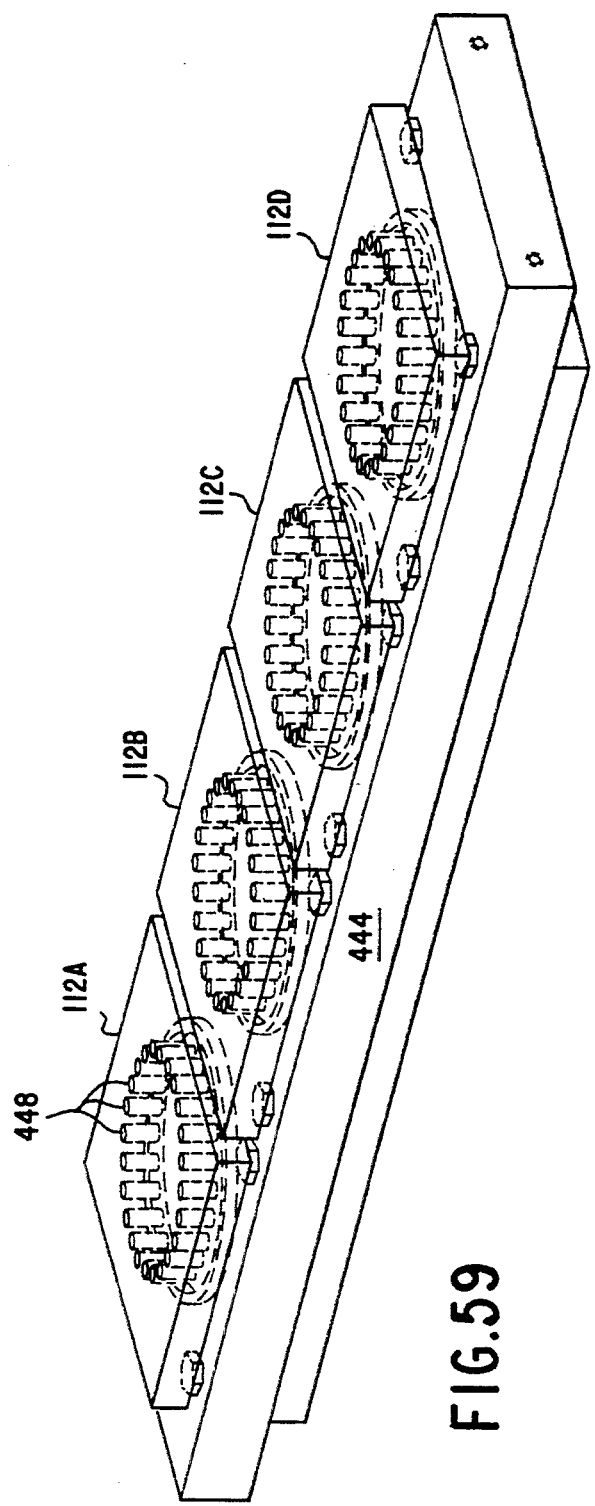

MULTIFUNCTIONAL FILTRATION APPARATUS

BACKGROUND OF THE INVENTION

1. Field Of The Invention

The present invention pertains to a multifunctional filtration apparatus for use in the laboratory for chemical and biological testing including the high speed transfer, filtration and treatment of samples containing filtrable substances. More particularly the invention pertains to a device for transferring and collecting filtrable substances on a filter medium utilizing a vacuum and a first manifold to transfer single or multiple samples from test tubes or micro sample plates to a separation chamber and employing the first manifold to separate the liquid and gaseous components of the transferred fluid containing filterable substances before separating the liquid and filterable substances by utilizing the filter medium and a second manifold. The first manifold and separation chamber are disposed on one side of the filter medium and the second manifold is disposed on the other side of the filter medium.

The invention is applicable to all types of filter mediums such as nitrocellulose, paper, nylon and other aerophobic filter mediums including biological membranes and to biological testing for which automated handling was not heretofore possible due to problems of rupturing the filter medium or membrane when the filter medium or membrane was exposed to air or other gases under pressure. The invention allows automation to be used in test procedures which heretofore could not accommodate the drawing of air into the filterable substances or filter medium due to the introduction of inaccurate results or the rupture of the filter medium caused by the entrainment of such air into the filter medium or filterable substances. The invention is able to handle any type of filter medium as well as air sensitive filtered materials captured in the filter by employing automated filtering techniques to replace the heretofore tedious manual operations where vacuum could not be used due to the aerophobic nature of the filter medium which would result in breaking, tearing, rupturing or contamination of the filter medium with air or other gases.

The invention more particularly pertains to a device for the automated transfer and separation of liquid, gaseous components and filterable substances by the utilization of the filter medium as a means for capturing the filterable substances while utilizing a first manifold to transfer and remove gaseous components from the transferred fluids in the separation chamber and utilizing the second manifold to remove liquids and filter the filterable substances on the filter medium. The invention is applicable to all types of laboratory and biological testing and filtering applications including the use of standard biological sample plates which include individual sample wells having volumes of around 0.5 ml for transferring the 0.5 ml sample, separation of the liquid and gas components from the transferred fluids and subsequently filtering the sample through either a filter or another micro filter plate with nitrocellulose filter bottoms by making slight modifications of the layered housing to provide for the separation of the liquid, particulate and gaseous materials utilizing the combination of a first manifold, second manifold and separation chamber.

2. Description Of The Prior Art

The prior art includes many different types of apparatus for filtering and transferring fluids and liquids. Many of the prior art devices for the rapid transfer of fluids utilize a vacuum source and a manifold to assist in the rapid transfer of fluids. Some of the prior art devices utilize two manifolds but none of the known prior art devices employ a first manifold and a separation chamber disposed on one side of a filter medium for transferring samples and then separating the air or the gaseous components of a transferred fluid from the liquid components of the transferred fluid before separating the liquid and solid or semi solid filterable substances by filtration through a filter medium.

In addition none of the known prior art devices provides a multifunctional filtration apparatus which is capable of high speed precision filtering of any fluid containing a filtrable substance through any type of filter medium including nitrocellulose, nylon or biological membranes which are aerophobic and which will not allow air to pass through the filter medium. None of known prior art provides a multifunctional filtration apparatus which allows the quick modification of the filtration apparatus from an aerophobic to an aerophyllic filter medium and from chemical to biological applications and for accommodating biological sample plates with nitrocellulose filter bottoms by substituting layers in the multilayered multifunctional filtration apparatus.

The most pertinent known prior art for filtering fluids is the Bertoncini, et al. U.S. Pat. No. 4,787,988. This prior art patent employs a first manifold, filter medium and a second manifold but does not employ a separation chamber and does not provide for the automated high speed transfer of filterable substances from one group of containers to another. U.S. Pat. No. 4,787,988 further requires test tubes to be manually placed in the device before the layers are put in place including the filter medium layer before the entire device is manually turned over and a vacuum applied to draw the liquid and filterable material in the liquid through the filter medium.

Bertoncini, et al. U.S. Pat. No. 4,787,988 unlike the present invention does not provide for the automated transfer of fluids from test tubes to a separation chamber to separate liquid and gaseous components before filtration. In addition U.S. Pat. No. 4,787,988 is not multifunctional since it is not suited for the filtration and handling of fluids through aerophobic filter membranes or mediums such as nitrocellulose since no separation chamber is provided between the first and second manifolds. In addition the first and second manifolds are not utilized in combination with one another to transfer fluids from a remote group of test tubes to the filter medium and thereafter provide for the separation of the gaseous and liquid components before filtration through a filter medium.

Other prior art such as Gruenstein, et al. U.S. Pat. No. 4,649,967 provides for the multiple transfer of fluids from one set of test tubes to another set of test tubes utilizing a vacuum and a manifold and a valve. Gruenstein '967 does not filter the transferred fluids and does not have a second manifold or a separation chamber. U.S. Pat. No. 4,649,967 merely provides for the transfer of fluids from one group of containers to a second group of containers. U.S. Pat. No. 4,649,967 is not suitable for nitrocellulose filter paper or filter mediums which are aerophobic and as such would not allow air to pass through a filter medium or filter membrane.

Aerophobic filter mediums or membranes such as nitrocellulose which do not allow air to pass through such as is used in biological testing where the addition of air under a vacuum to the filter results in damage to the filter medium or causes errors in the test results due to the reaction of air with the sample has heretofore required the manual transfer of fluids to a device such as disclosed in Lombardy U.S. Pat. No. 4,828,801. In such aerophobic filter mediums liquids containing filterable materials are introduced manually to either drain through the nitrocellulose filter medium or be drawn through by means of a vacuum on only one side of the filter medium to allow the vacuum to speed up the filtration process. A similar device is shown in Levin U.S. Pat. No. 4,978,507 which similarly provides for the manual loading of each of the samples to a membrane or nitrocellulose sheet along with the utilization of a manifold and vacuum only on one side of the filter for drawing filtrable mediums through the nitrocellulose filter or membrane which is not pervious to gases. In such devices the step of transferring the samples has heretofore been accomplished manually and not accomplished by the automated transfer of fluids with a vacuum.

Other prior art patents pertaining to multi well apparatus for biological and biochemical analysis generally provide a manifold on the bottom side of the filter medium to draw liquids containing filtrable matter through the filter medium after manually filling the wells. In all such biological applications cross-contamination between the various sample wells is prevented by clamping the various layers together with a filter medium or membrane disposed between the layers. In all such known prior art filterable fluids must be manually transferred or loaded into the wells. Such prior art includes Bowers, et al. U.S. Pat. No. 5,108,704; Mathus, et al. U.S. Pat. No. 4,927,604; Clark, et al. U.S. Pat. No. 4,902,481; and Schuette U.S. Pat. No. 5,108,603. In all of these prior art examples the fluids containing filtrable substances are manually loaded in the micro sample plate or test tubes before a vacuum is applied to draw the filtrate component of the fluid through the filter medium. In all such applications the automated transfer of fluids is lacking as well as the utilization of a separation chamber to provide for the separation of liquid from gaseous components from the transferred fluids before filtration.

In all known prior art, unlike the invention, washing and subsequent reagent addition steps are again accomplished manually. In the known prior art pertaining specifically to nitrocellulose and aerophobic filter mediums such as inter alia Bowers, et al. U.S. Pat. No. 5,108,704, Schuette, U.S. Pat. No. 5,108,603 and Levin, U.S. Pat. No. 4,978,507 the tops of the wells are left open to allow gaseous components of a fluid to escape to the atmosphere instead of being captured and removed by the first manifold. This of course limits the prior art filter systems since a rapid transfer of fluids is not possible since all transfers and addition of wash solutions and reagents must be made manually into the sample wells of the prior art apparatus or into the openings of the wells of micro sample plates which prevent the high speed washing or addition of solvents or reaction chemicals.

The invention in contrast to the prior art provides for the high speed transfer of fluids, washing as well as the addition of reaction reagents by the utilization of a combination of a separation chamber and a first manifold located on one side of the filter medium and a second manifold located on the other side of the filter medium. With this arrangement samples can be individually and quickly transferred from a number of test tubes, or wells of a micro sample plate or containers quickly and in a single step without cross-contamination and thereafter filtered, washed and reagent materials added all without the numerous manual steps heretofore required in the prior art. The invention is also applicable to all types of filter mediums whether air impervious or not by the utilization of the separation chamber to separate and provide for the removal of gaseous components from the liquid component of introduced fluids before the solid or filtrable components are removed by the filter medium through the activation of the second manifold.

The features of the invention allows the invention to be configured in a number of different arrangements to allow the multifunctional filtration apparatus to be used for a number of different types of filtering procedures and applications in which fluids are individually removed, transferred and the components separated before filtration through any number of different types of filter mediums. These aspects of the invention also allow for the automated and controlled addition and collection of wash fluids or reagents to provide for the washing or further reacting or other processing steps which in the prior art required a number of separate manual and tedious steps that have been obviated by the novel multifiltration apparatus of the invention.

The invention in further contrast to the prior art can be configured in a number of different arrangements to allow any type and quantity of filtrable materials to be transferred to a separation chamber and the liquid and gaseous components separated before separation of the liquid and filtrable components by filtration followed by subsequent washing and reagent addition operations by the use of high speed vacuum techniques. The invention further allows for the use of all types of filter mediums whether or not they are gas impervious so that gases can be removed before filtration in order to prevent the air or gases from destroying, deforming or otherwise interfering or reacting with the filter medium or filtered materials.

SUMMARY OF THE INVENTION

The disadvantages and limitations of prior art apparatus and manual methods for transferring handling and filtering fluids where gas impervious filter mediums are utilized is obviated by the invention. The invention provides for the high speed transfer and automated filtration using all types of filters or biological membranes by providing for the automated transfer and high speed separation of fluids into their liquid and gaseous components and filtering filtrable materials from the liquids while preventing gaseous components of the fluid from interfering with the filtration process or collected filtrate. The invention also provides for the high speed and individual treatment of each of the samples including washing and reagent addition steps without cross-contamination between one or more of the individual samples.

The apparatus of the invention provides for the high speed transfer of fluids and filtering out filterable constituents by employing a first manifold to transfer from one to a plurality of discrete samples from a sample source to one or more separation chambers where gaseous components are separated from liquid components of a fluid containing a filtrable substance. Once the fluids are transferred along with any air drawn by a vacuum to the separation chamber the liquid and gases are separated in the separation chamber by the first manifold. The second manifold is then activated to remove filtrable substances from the liquid. The second manifold is disposed on the opposite side of the filter medium from the first manifold.

A valve is provided for individually accessing the first manifold and the second manifold either separately or in combination. The valve provides for the removal of the gaseous components through the first manifold. Where necessary the gaseous component can also be separately collected without the necessity of using a hood or a separate processing step. The liquid component of the fluid along with filtrable substances may then be drawn through the filter medium thereby capturing the filtrable substances on the filter medium. The valve may be designed in one embodiment to sequentially access the first manifold and then the second manifold. In this application the gas and liquid are first separated before separating the liquid and solid or semi-solid filtrable components. Alternatively the valve may be designed to simultaneously access both the first and second manifold in which case gas, liquid and filterable substances may be simultaneously separated. In the preferred application the gas and liquid components are first separated before filtration to reduce the possibility of air contacting the filter medium.

Once the gaseous component is removed from the separation chamber the liquid component containing filterable materials can be drawn into or through the filter medium thereby preventing destruction of the filter medium where the filter medium is air impervious such as nitrocellulose. In addition the removal and possible separate collection of the gaseous component prevents the unwanted interference or reaction between the gaseous or air component of the fluid with the filtrable substance captured on the filter medium.

The multifunctional filtration apparatus by utilizing the first manifold and second manifold disposed on different sides of the filter medium together with a separation chamber allows the solid, liquid and gaseous components to be separately collected, treated and handled. The separate handling of the fluid components consisting of gas and liquid are as a result not drawn into the filter medium to interfere with either the filter medium or filtrable substances captured in the filter medium not only in the filtering operation but also in other optional phases of operation such as washing, reacting or other such steps which can also be carried out on the filter medium without cross-contamination of each of the individual samples trapped in the filter medium.

The invention is applicable to all types of filtration and filtration mediums including nitrocellulose filters and aerophobic membranes of macromolecular complexes such as are used in protein studies. Such biological applications in the past have required the utilization of manual transfers of liquids and filtrable substances through such filter mediums to prevent introduction of air into the filter medium or filtrable substances captured in the filter medium to prevent damage to the filter medium by exposure to the air or gases that may be present and should be removed in some of the fluids containing filtrable substances.

The invention accommodates such biochemical filtration procedures and prevents cross-contamination while providing for the rapid handling of such solutions containing filtrable substances. The apparatus of the invention also allows for the filtration through nitrocellulose or other aerophobic filter mediums by utilizing a layered filtration apparatus having a first manifold in the uppermost layer, a separation chamber disposed in a second layer which may be hinged or otherwise detachably secured to a third layer which forms a support for the filter medium. The third layer is similarly attached to the fourth layer which forms a second manifold disposed on the other side of the filter medium.

The apparatus allows fluids to be easily and rapidly transferred from test tubes or sample trays through the uppermost layer to the separation chamber in the second layer by use of the first manifold. The first manifold also allows gases to be removed from the transferred fluids through the first manifold before the second manifold in the third layer is activated to draw only the liquid component of the fluid through the filter medium which may include air impervious filters such as a nitrocellulose filter medium and thus trap the filtrable substances in the filter medium. The liquid component drawn through the filter medium into the second manifold can optionally be collected in the second manifold or be drawn from the second manifold and separately collected.

In accordance with the invention the gaseous component is prevented from damaging either the nitrocellulose filter medium or causing damage to filtrable substances trapped in the nitrocellulose filter medium since the gases are separated from the liquid by the physical differences between gases and liquids and by the second manifold. Subsequent washing or reacting of the substance captured on the filter medium may similarly be accomplished by transferring wash solutions into the separation chamber utilizing the first manifold and separating any gaseous components from the wash or reagent solutions added utilizing the first manifold to remove any air drawn in the transfer of wash solutions from the wash solution or reagent source or in the interconnecting lines in the separation chamber.

The invention is applicable to not only biological testing but all types of high speed rapid filtering operations which require the separate filtering of individual samples without cross-contamination and with minimal manual intervention. The high speed filtering apparatus of the invention further prevents tearing and destruction of the filter medium by the introduction of air or other gases under pressure into the filter paper or filter medium which in some testing operations could react with substances trapped in the filter medium or rupture the filter medium.

The apparatus of the invention is susceptible to many embodiments utilizing virtually any number and arrangement of test tubes or sample wells while providing for the individual filtration of any number of discrete samples utilizing the first manifold and the second manifold and separation chamber. The novel multifunctional filtration apparatus of the invention is adaptable to any number of test tubes and can be configured for one or more test tubes or designed for standard 24, 48, 96, 384 or more test tubes or sample well tray arrays. The novel multifunctional filtration apparatus in addition can be used with standard sample plates as is generally used in biological studies utilizing 96 wells in 8 columns of 12 rows in a square plate of about $4\frac{3}{4}$ inches by 3 inches in which the opening for each well is about 0.125 inch. These wells are also about 0.4 inch deep and hold only about 0.5 ml of sample. The invention is applicable to these small volumes or can be adapted to large volumes of 1,000 ml or more to provide for the transfer and separation of gases from the liquid by the first manifold and filtered utilizing the second manifold and subsequently washed or treated with other reagents without cross-contamination.

In a further embodiment of the invention the third layer or filter support layer of the novel multifunctional filtration apparatus may be modified to accommodate an entire 96 hole micro sample plate having individual wells terminating in a nitrocellulose filter medium as has been recently introduced by Costar, Inc. of Cambridge, Mass. which is currently used in many biological studies. In such an arrangement automated transfers can be made from one 96 hole micro sample plate using a vacuum to another micro sample plate with filter wells and filtration accomplished in accordance with the invention without tedious manual transfers and filter operations.

The novel arrangement of the first and second manifold together with a fluid separation chamber for the separation of transferred fluids into gaseous and liquid components together with a valve for activating the first and second manifolds to provide for the separate treatment and filtration of discrete samples allows for the ease of transfer of large and small quantities of filtrable materials to a filter medium and the separate filtering of each of the discrete samples without cross-contamination. In this manner the invention also provides for a multitude of filter mediums which may or may not be gas impervious to provide for rapid transfer, filtering and handling of filtrable components from fluids while allowing subsequent washings and reagent additions or reactions to not interfere with the filter medium. The arrangement is also useful in collecting noxious gases from the first manifold without the necessity of using a hood or other laboratory equipment as well as the collection of hazardous and radioactive fluids.

Wash solutions and reaction solutions may similarly be individually added to each of the discrete samples without cross-contamination. Wash solutions drawn by the vacuum may similarly contain gaseous components introduced from the hoses or lines before or between samples which are separated out of the fluid in the separation chamber before the fluid portion is drawn through the filter medium. The novel multifunctional filtration apparatus also preferably includes vacuum controlled purge lines connected to the valve to remove wash solutions or reagents from the lines so as to carefully control and manage the addition of the sample and solutions to the filter medium.

The novel separation chamber should have a total volume greater than the total volume of the sample to be transferred and filtered. The device of the invention can be constructed to accommodate samples and quantities of liquid from 0.1 ml to 1,000 ml or more. However in each case the total volume of the separation chamber should be about 5% to 100% greater and preferably 30–50% greater than the volume of fluid transferred where the multipositional valve is not designed to simultaneously access both the first manifold and the second manifold to provide for the simultaneous transfer and separation of liquids and gases and filterable substances. In embodiments where the multipositional valve simultaneously accesses both the first manifold and the second manifold the separation of chamber must only be of a size sufficient to accommodate the rate of flow and the filter capacity of the filter and provide room for the removal of gas without interfering with the filter.

The fluid injectors which inject fluid into the separation chambers also should extend down into the separation chamber sufficiently to prevent injected fluids from splashing at the tops and sides of the separation chamber. The fluid injectors should direct the transferred fluids to about the center of the filter medium where small amounts for example 0.1 ml to 5 mls are transferred and filtered. The length of the injector in relation to the length of the separation chamber is also related to the volume of the fluid being transferred and filtered. Where small volumes of fluid are being filtered and transferred the fluid injector should extend from about 25 to 90% the total length of the separation chamber. Where larger volumes of fluid are transferred the fluid injector should extend from 10 to 90% of the total length of the separation chamber.

The individual samples transferred and filtered without cross-contamination can thereafter be further purified, treated or analyzed without contamination or interference with either the filtered substances or the filter medium by the gaseous constituent of fluids transferred to the filter medium by the novel multifunctional filtration apparatus. Upon completion of the filtering process the filter medium can be washed or further reacted by the addition of reaction reagents or the individual micro sample plates containing the nitrocellulose filter medium may be removed for further laboratory work.

BRIEF DESCRIPTION OF THE DRAWINGS

For a better understanding of the invention, reference is made to the accompanying drawings in which:

FIG. 4 is a side elevational view partly in section of FIG. 3;

FIG. 5 is a side elevational view similar to FIG. 2 illustrating the operation of the first manifold of the invention;

FIG. 6 is a top plan view similar to FIG. 3 illustrating the position of the valve for transferring fluids in FIG. 5;

FIG. 20 is a front elevational view of the wash and evacuation arm of the multifunctional filtration apparatus of FIG. 17;

FIG. 21 is a top plan view of the uppermost layer or block of the multifunctional filtration apparatus of FIG. 17;

FIG. 22 is a side elevational view of FIG. 21;

FIG. 23 is a bottom plan view of FIG. 21;

FIG. 24 is a top plan view of the separation chamber layer or block of the multifunctional filtration apparatus of FIG. 17;

FIG. 25 is a bottom plan view of FIG. 24;

FIG. 26 is a side elevational view partly in phantom of FIG. 24;

FIG. 27 is a side elevational view partly in phantom illustrating the filtration support layer or block of the multifunctional filtration apparatus of FIG. 17;

FIG. 28 is a top plan view of FIG. 27;

FIG. 29 is a bottom plan of FIG. 27;

FIG. 29A is a perspective view partly in phantom illustrating the second manifold layer or block of the multifunctional filtration apparatus of FIG. 17;

FIG. 39 is a perspective view partially exploded illustrating a modification of the filter support layer and alternative micro sample well insert with filter insert and adaptor insert for filter paper support constructed in accordance with the invention;

FIG. 48 is a top plan view with the gasket partly in section of the third layer of the novel multifunctional filtration apparatus of FIG. 35;

FIG. 49 is a bottom plan view of FIG. 48;

FIG. 50 is a perspective view without a gasket partly in phantom of FIG. 48;

FIG. 51 is a front elevational view partly in phantom of FIG. 50;

FIG. 59 is a perspective view of the wash manifold portion of the multifunctional filtration apparatus of FIG. 36;

FIG. 60 is a bottom plan view of one of the wash well manifolds of FIG. 59;

FIG. 61 is a side elevational view partly in section of FIG. 59;

DETAILED DESCRIPTION OF THE PREFERRED EMBODIMENTS

The multifunctional filtration apparatus of the invention is applicable to all forms of high speed filtration which require the transfer and filtration of fluids containing filtrable substances from a container to a filter or filter membrane for removal of the filtrable substances. The invention is applicable to any number of samples as well as types of filter mediums or membranes whether or not they are impervious to air or gases by the utilization of a first manifold and separation chamber disposed on one side of the filter and a second manifold disposed on the other side of the filter. The invention achieves its advantages by creation of a pressure $P_1$ on the first manifold side of the filter and the creation of a second pressure $P_2$ on the second manifold side of the filter where $P_2$ is greater than $P_1$. The advantages of the invention are further achieved by utilizing $P_1$ to remove air or gaseous components from the $P_1$ side of the filter before or somewhat contemporaneous with the creation of $P_2$.

The invention is applicable to large quantities (1,000 ml or more) or small quantities of less than 0.5 mil volumes of filterable fluids. The invention is particularly advantageously applied to systems which utilized a filter or filter medium which is impervious to gases or where filterable materials captured in the filter cannot be contaminated with gases that would normally be drawn through or into the filter membrane or filter medium.

The advantages of the invention are achieved by utilizing a first manifold and separation chamber disposed on one side of the filter medium to provide for the transfer of fluids containing filterable substances. The first manifold and separation chamber also provides for the separation of transferred fluids into their gaseous and liquid components before the liquid component is drawn through the filter medium by utilizing the second manifold to separate the liquid from the filtrable substances. Subsequent washings or reaction of the materials captured in the membrane or filter may similarly be accomplished by using the first manifold to transfer fluids to the separation chamber before the fluid is once again separated into its liquid and gaseous components in the separation chamber. Once the gaseous component is removed from the transferred wash or reaction fluid in the separation chamber the second manifold is activated to draw the wash liquid or reagent into the filtered materials without the filter membrane or filtrable materials being contaminated by a gaseous component of the transferred fluid.

Figure 1:
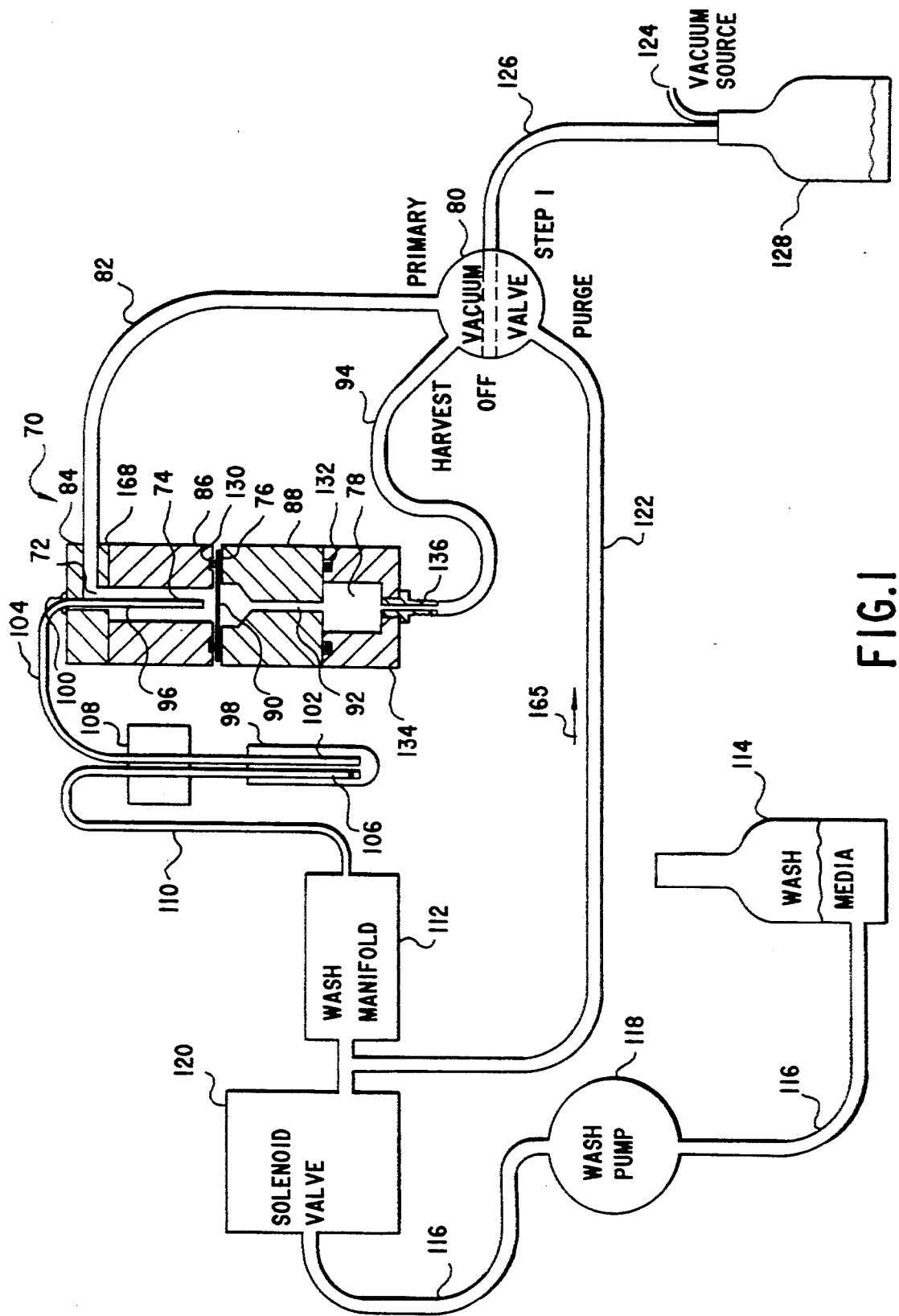
FIG. 1 is a diagrammatic side elevational view partly in section of the invention.

Referring now to FIGS. 1, 2, 3 and 4 a high speed multifunctional filtration apparatus 70 is illustrated having a first manifold 72, a separation chamber 74, a membrane or filter 76 and a second manifold 78. The first manifold 72 is connected to a multiposition vacuum valve 80 through a conduit 82 which is connected to either the second block or layer 86 or the first block or layer 84 as illustrated in FIG. 1. The first layer 84 is utilized for the purpose of creating the first manifold 72 in cooperation with a second block or layer 86 which together with the first layer 84 also forms the separation chamber 74. It will be recognized the first manifold can also be formed along with the separation chamber in a single upper layer but that for purposes of ease of construction it is generally preferable to utilize a first block or layer 84 and a second block or layer 86 to form the first manifold 72 and the separation chamber 74.

The third block or layer 88 is used as a filter support block which may include a screen or filter support 90 to provide support for a membrane or filter 76. The third layer or block 88 includes a channel 92 which connects the filter paper support 90 to the second manifold 78 which is connected to valve 80 by means of a conduit 94. The purpose of the third layer 88 and fourth layer 134 is to create a higher pressure side $P_2$ on filter 76 than on the lower pressure side $P_1$ or filter 76 in separation chamber 74. As will be recognized by those skilled in the art the $P_2$ side of the filter can be created by the combination of Layer 88 and layer 134 into a single layer with grooves similar to layer 184.

The high speed multifunctional filtration apparatus 70 further includes a fluid injector 96 which extends down into chamber 74 from about 2% to 95% of the total length of chamber 74. The length of injector 96 is dependent upon the volume of fluids transferred as well as the type of sample being transferred from a test tube 98 to the separation chamber 74. Generally where large volumes of fluids are utilized injector 96 can be shorter since it is not as important to get all or almost all of the sample deposited at or near the center of the membrane or filter 76. However where small volumes of fluid containing small amounts of filterable materials are utilized it is preferable to extend the length of injector 96 to almost the complete length of chamber 74 to direct the sample removed from test tube 98 directly onto the center of the membrane or filter 76 so that splashing of the sample around the sides of chamber 74 is minimized.

Figure 38:
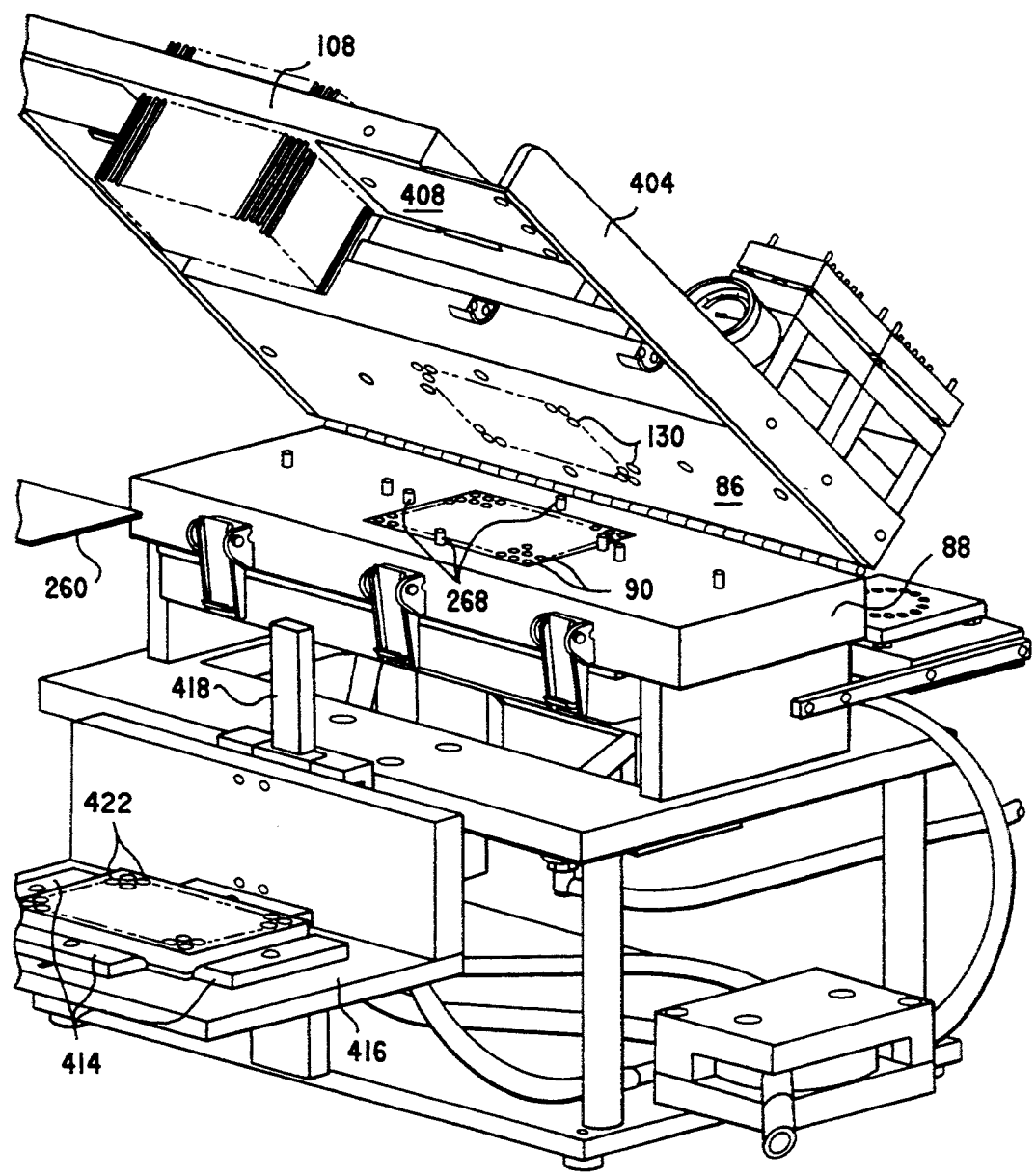
FIG. 38 is a perspective view of FIG. 37 partially exploded and with portions removed for purposes of illustration illustrating the moveable sample support tray.
Figure 43:
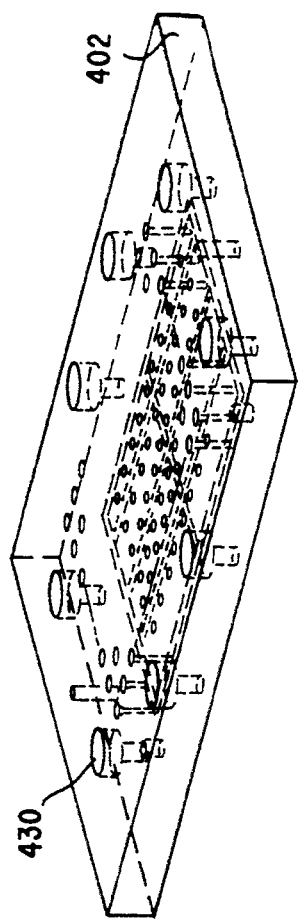
FIG. 43 is a perspective view of FIG. 40.

Injector 96 is sealed by means of a seal 100 at the top of layer 84 to provide an airtight seal so that first manifold 72 can be evacuated by placing the multiposition vacuum valve 80 in the PRIMARY position. Injector 96 at the top end is connected to a fluid pick up needle 102 by a conduit 104. The fluid pickup needle 102 is disposed adjacent to and in a closely spaced arrangement with a wash or reagent addition needle 106. Wash or reagent addition needle 106 is spaced from pickup needle 102 at a distance of less than the diameter of the test tube 98 or the diameter of a well in a test plate (about 0.125 in) which wells of a similar test plate is illustrated in FIG. 38 in connection with a further embodiment of the multifunctional filtration apparatus of the invention.

The fluid pickup needle 102 and wash or reagent addition needle 106 are positioned in a housing 108 which may be manually moved to the sample test tube 98. The wash or reagent addition needle 106 is connected via a conduit 110 to a wash manifold 112 which is connected to a wash or reagent media 114 by a conduit 116 which is also connected to a wash pump 118 which is controlled by a solenoid valve 120 to pump wash fluid or a reagent to the wash manifold 112 and conduit 110 and then into test tube 98 through wash or reagent addition needle 106.

Figure 7:
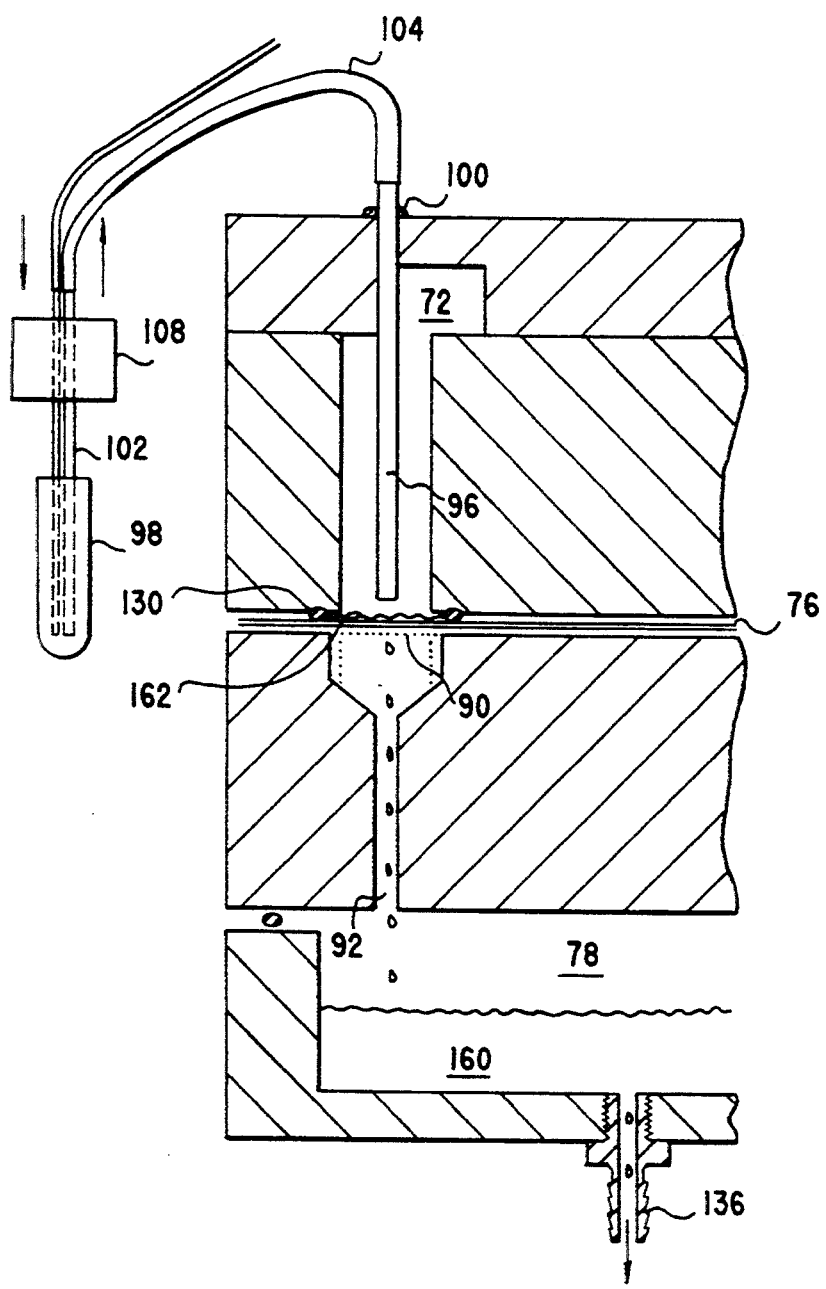
FIG. 7 is a side elevational view similar to FIG. 2 illustrating the utilization of the second manifold.
Figure 8:
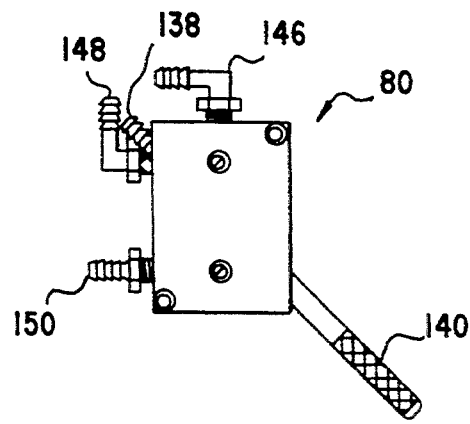
FIG. 8 is a top plan view similar to FIG. 3 illustrating the position of the valve to filter or harvest samples as illustrated in FIG. 7.
Figure 9:
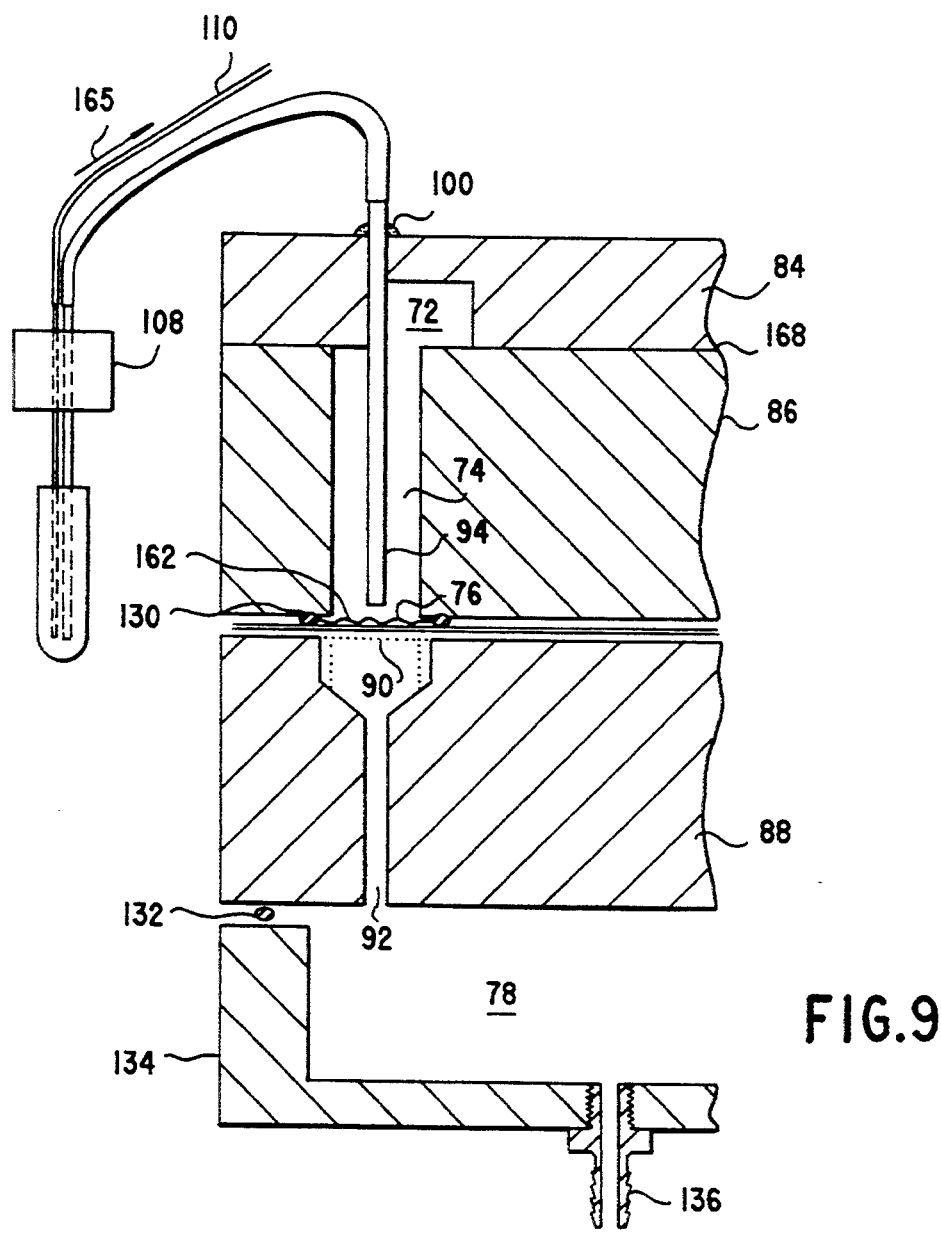
FIG. 9 is a side elevational view similar to FIG. 2 illustrating the purge operation of the invention.
Figure 10:
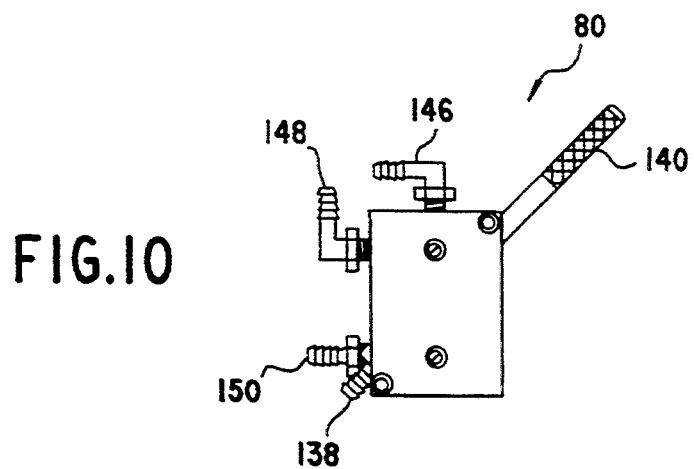
FIG. 10 is a top plan view similar to FIG. 3 illustrating the position of the valve to accomplish the purge operation of the invention as illustrated in FIG. 9.

Multiposition vacuum valve 80 is connected to a purge conduit 122 to allow the vacuum source 124 to evacuate any wash or reagent fluid remaining in wash or reagent addition needle 106 as well as fluid in conduit 110 and wash manifold 112 through conduit 122 when the multiposition vacuum valve 80 is placed in the PURGE position (FIG. 9 and 10). The purge allows fluids to be removed from high speed filtration apparatus through purge conduit 122 and through valve 80 and into trap reservoir 128 through conduit 126. The high speed multifunctional filtration apparatus also includes an O-ring or seal 130 to provide a seal around the bottom of chamber 74 and the membrane or filter 76. O-ring 130 together with seal 132 between the fourth block or layer 134 and the third block or layer 88 results in the filtration of liquids on filter 76 when valve 80 is moved to the HARVEST position (FIGS. 7 and 8) to evacuate the second manifold 78. A suitable fitting 136 is provided to connect conduit 94 to layer 134.

Figure 3:
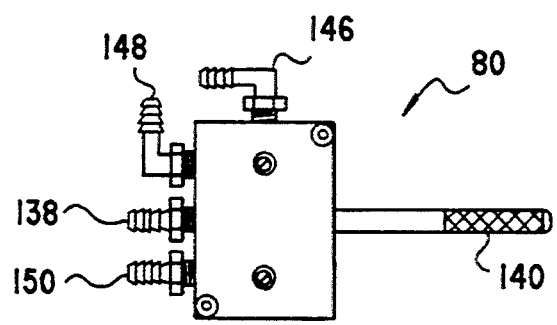
FIG. 3 is a top plan view of a vacuum control valve for operating the invention.
Figure 2:
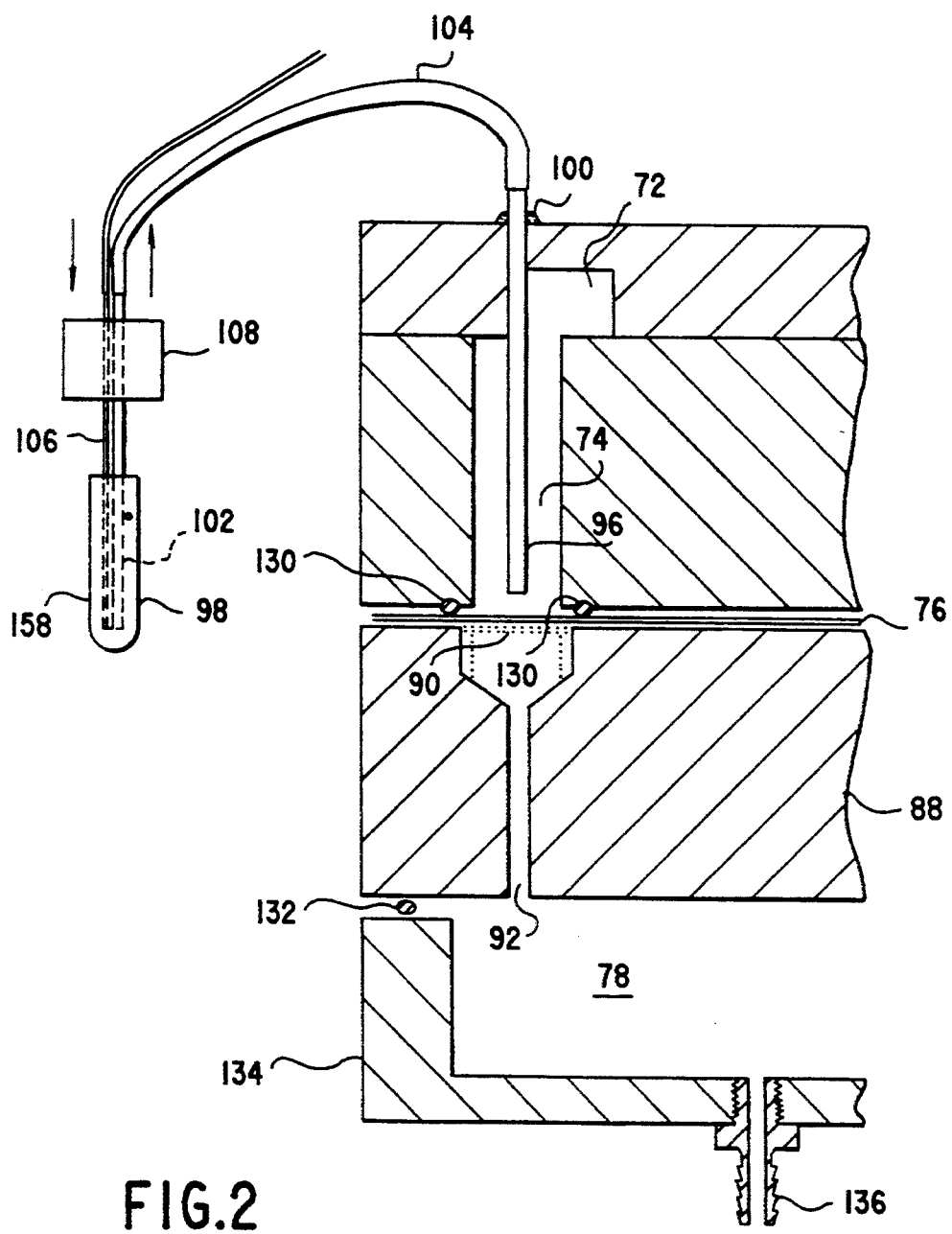
FIG. 2 is a fragmentary side elevational view of the first and second manifolds, fluid injector and separation chamber of the invention.

The multipositional vacuum valve 80 is illustrated in FIGS. 3 and 4 and includes PRIMARY, HARVEST, OFF and PURGE positions. Valve 80 is preferably arranged such that a vacuum port fitting 138 is connected to a vacuum source 124 through conduit 126 attached to fitting 138 so that when handle 140 is rotated in housing 142 an alignment of the port 143 and opening 152 is selectively accomplished by rotatable body 144 with the primary port fitting 146, the harvest port fitting 148 and the purge port fitting 150. The vacuum port fitting 138 and opening 152 are not in alignment with either the primary, harvest or purge fitting when handle 140 is in the OFF position (FIG. 3). As soon as handle 140 is rotated, for example to the PURGE position, the opening 156 in housing 142 comes in alignment with opening 152 in rotatable body 144 to open purge line 122 to vacuum source 124 through conduit 126 attached to vacuum port fitting 138 to allow the evacuation of wash manifold 112, conduit 110 and wash or reagent addition needle 106. Similarly, each position of valve 80 other than the OFF position selectively opens each of the fittings 146, 148 and 150 to conduits 82, 94 and 122 respectively to the vacuum source 124.

Referring now to FIGS. 1-6, the transfer of fluids from test tube 98 to separation chamber 74 is illustrated. In operation handle 140 (FIG. 3) is moved from the OFF position to the PRIMARY position (FIG. 6) which results in the transfer of fluid 158 from test tube 98 (FIG. 2) to separation chamber 74 by drawing the fluid 158 through needle 102 and through conduit 104 and discharging fluid 158 together with air or gases in conduit 104 and air from test tube 98 after fluid 158 has been removed through injector 96 on to the top of membrane or filter 76. The movement of handle 140 of valve 80 to the PRIMARY position connects the vacuum fitting 138 port 143 and hole 152 with primary port fitting 146 and conduit 82 by evacuating first manifold 72. The evacuation of manifold 72 through conduit 82 not only provides for the rapid transfer of fluid 158 from test tube 98 to separation chamber 74 (FIG. 5) but also allows for the separation and removal of the gaseous component of fluid 158 and any air or gases drawn through conduit 104 or from test tube 98 after the transfer of fluid 158 by the removal of all gaseous components from separation chamber 74 through conduit 82.

Once fluid 158 has been transferred to separation chamber 74 and all gases 157 (FIG. 5) are separated and removed from fluid 158 through first manifold 72 and the liquid portion of fluid 158 containing filtrable substances remains in separation chamber 74 above the membrane or filter 76 until handle 140 is moved from the PRIMARY position to the HARVEST position (FIG. 8) which results in the connection of the opening in vacuum fitting 138 with the passage 152 to the opening in the harvest port fitting 148 which results in the application of vacuum to second manifold 78 (FIG. 7) through conduit 94 (FIG. 1) resulting in the drawing of the liquid portion 160 of fluid 158 through the membrane or filter 76 and the capture of filtrable substances 162 on membrane or filter 76.

In this manner the gaseous component of fluid 158 and any air drawn through conduit 104 or from test tube 98 during the transfer of fluid 158 is not drawn into membrane or filter 76 and as a result is not available to interfere with the filtrable substance 162 on filter 76 or with an air impervious filter medium such as a nitrocellulose filter medium or a biological membrane. Thereafter if the filtrable substance 162 is to be reacted with a reagent handle 140 is moved to the OFF position (FIG. 3) and a new test tube 98 containing reagent is placed in position and handle 140 is moved back to the primary position (FIG. 6) and the reagent solution is transferred from test tube 98 to separation chamber 74 (FIG. 5) so that the gaseous component may be separated in separation chamber 74 and removed through manifold 72 before the reagent or reaction solution is reacted with substance 162 on filter 76. Thereafter handle 140 is again moved to the harvest position (FIG. 8) and the solution is drawn through the membrane or filter 76 into the second manifold 78 in a manner similar to that previously described.

In the event the addition of a reagent is not required, but instead a washing of test tube 98 is desired, a switch 164 (FIG. 20) on housing 108 may be utilized to activate the solenoid valve 120 to activate wash pump 118 to pump wash fluid from the wash media 114 through conduit 116 to the wash manifold 112 and conduit 110 to the wash or reagent addition needle 106 to wash any remaining contents of test tube 98 out of test tube 98 while handle 140 remains in the PRIMARY position to use vacuum to simultaneously withdraw the wash fluid and any remaining contents of test tube 98 out through conduit 104 into separation chamber 74. The continuous application of vacuum draws the wash fluid into separation chamber 74 and results in the separation of the gaseous component of the fluid from the liquid component of the fluid before it is drawn through filter 76 by moving handle 140 from the PRIMARY position to the HARVEST position.

Once all reacting and washing has been completed handle 140 is moved to the PURGE position (FIG. 10) to connect the passage 152 with the opening in vacuum fitting 138 to the opening in purge port fitting 150 to connect conduit 122 with wash manifold 112 to remove fluid from wash or reagent addition needle 106, conduit 110 and wash manifold 112 (FIGS. 1 and 9) in the direction of arrow 165. In this manner the wash manifold and wash or reagent addition needle 106 may be cleared to prevent any possibility of contamination with a new set of samples.

The advantages of the invention are achieved by the utilization of the first manifold, second manifold and one or more separation chambers disposed between the first and second manifold. The combination of manifolds and separation chamber may be conveniently formed by employing four separate layers, two of which layers 86 and 88 may be opened and closed with respect to each other by means of a hinge 166 (FIG. 18) or by other means to allow for the insertion of a membrane or filter 76 between layers 86 and 88.

In the preferred application of the invention four layers 84, 86, 88 and 134 are utilized to form the first manifold, separation chamber and second manifold. The top layer 84 may be screwed or bolted to the second layer 86 with a suitable seal or gasket 168 to form an airtight manifold 72 at the top of separation chamber 74. As indicated the top layer may be hinged by a hinge 166 to the bottom two layers 88 and 134 to allow the top two layers 84 and 86 to be easily separated from the third layer 88 to change or add a new membrane or filter 76. An O-ring or seal 130 is provided to provide a fluid tight seal for the first and second manifolds and to prevent cross-contamination between individual samples where a plurality of samples are utilized as will be described hereinafter in greater detail.

The filter support or third block or layer 88 is secured to the fourth layer 134 by means of screws or other mechanical closure and includes a seal 132 which may be in the form of an O-ring to provide an airtight seal between layers 88 and 134. In the preferred embodiment of the invention each of the layers 84, 86, 88 and 134 are mechanically attached to allow service and disassembly after use as well as for the ease of modification and substitution of various components as will be described hereinafter in greater detail. The ease of disassembly is particularly important in various biological types of testing using radioactive or hazardous components where sterilization or other processes for thoroughly cleaning the multifunctional filtration apparatus might be desired.

Referring now to FIGS. 11–16 the application of the invention to provide for the high speed transfer and filtration of four separate samples without cross-contamination is illustrated. As previously discussed the invention is applicable to any number of samples where the rapid transfer and filtration of solutions containing filtrable substances is desired from either test tubes or from biological sample wells or sample plates. Any number of test tubes or samples can be provided including even or odd numbers, but the most utilized numbers of samples are generally 24, 48 and 96 with new sample trays including as many as 384 samples utilizing a tray similar to the 96 micro well sample tray except having 384 micro sample wells.

Figure 11:
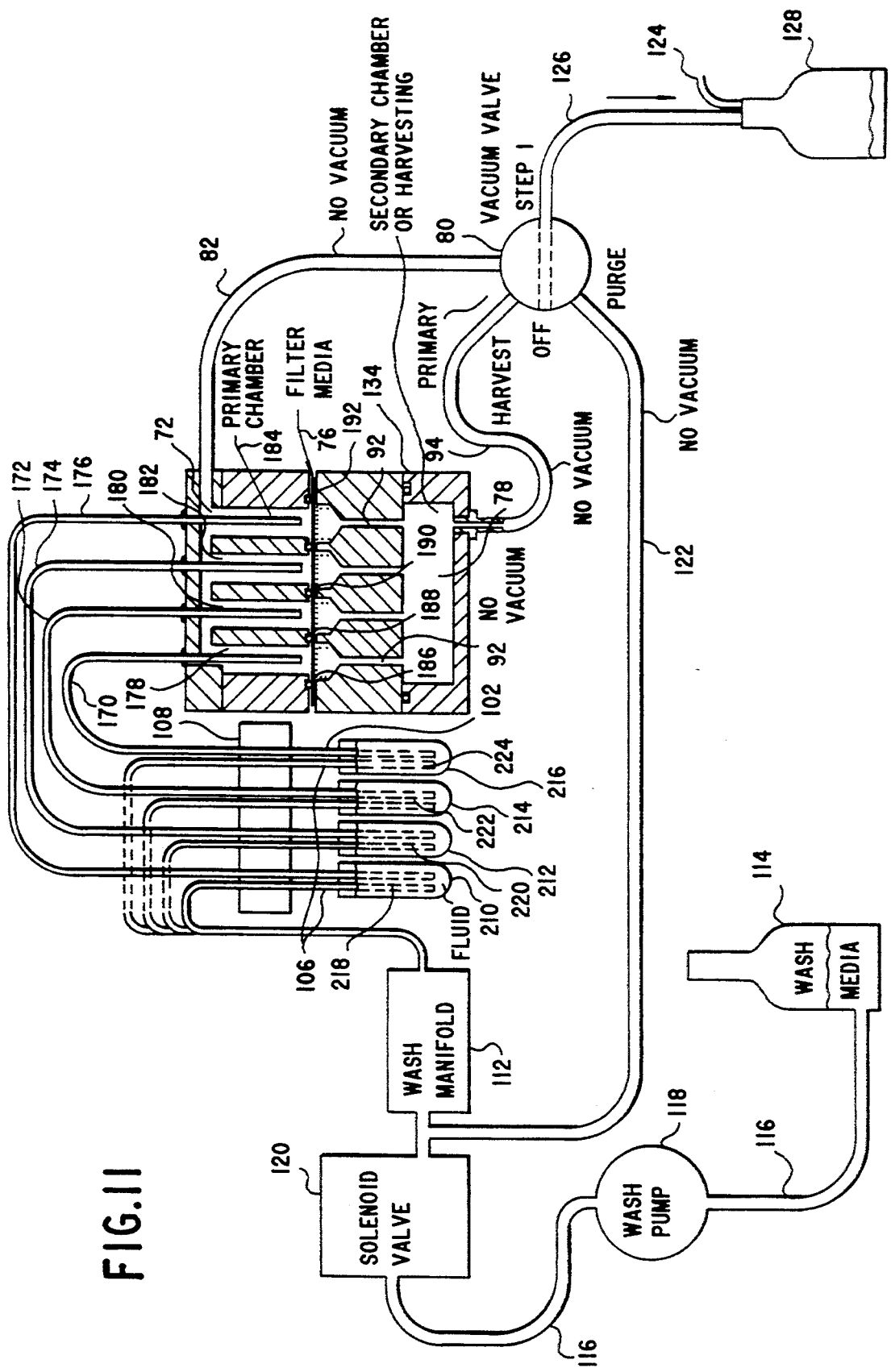
FIG. 11 is a schematic view partly in section illustration of the invention utilizing multiple samples.

The high speed multifunctional filtration apparatus as illustrated in FIG. 11 includes the multiposition vacuum valve 80, primary conduit 82, harvest conduit 94, purge conduit 122 and wash conduit 116, wash manifold 112, solenoid valve 120, wash pump 118 and wash media 114 which have been numbered similar to those already discussed with reference to FIGS. 1–10. The major difference between FIG. 1 and FIG. 11 is that FIG. 11 includes four separate test tubes each containing a different sample of fluid containing a filtrable substance and the housing 108 now includes four pair of fluid pickup needles 102 and wash or reagent addition needles 106. Each of the wash or reagent addition needles 106 are separately connected to a common wash manifold 112 and each of the fluid pickup needles 102 are separately connected via separate conduits 170, 172, 174 and 176 to four separate separation chambers 178, 180, 182 and 184.

The tops of each of the separate separation chambers 178, 180, 182 and 184 are connected to a common first manifold 72 which is connected via conduit 82 to vacuum valve 80. Cross-contamination between each of the samples is prevented by utilizing four separate O-rings 186, 188, 190 and 192 to encircle the bottom of each separate separation chamber and provide for each of the four discrete filter areas on filter medium 76 to prevent cross-contamination of samples. Similarly four separate screens or filter support members 90 are provided along with four separate channels 92 which connect with the common second manifold 78. It will be recognized by those skilled in the art the separate collection of filtrates can be accomplished by adding optional injector needles 194, 196, 198 and 200 along with sample containers 202, 204, 206 and 208 (FIG. 12) where the collection of the effluent is also desired. Generally collection of the filtrate is not desired in many filtering operations but can be easily accommodated in accordance with the present invention by allowing for the easy separation of layers 88 and 134 by providing for latches or other quick release means for providing for the separations of layers 88 and 134.

The process for rapidly transferring and filtering a plurality of samples from a multiple of individual test tubes 210, 212, 214 and 216 to a plurality of individual separation chambers 178, 180, 182 and 184 is similar to that described with respect to FIGS. 1–10. More particularly the multipositional vacuum valve 80 is placed in the OFF position, the four test tubes 210, 212, 214 and 216 are introduced to the paired fluid pickup needles 102 and wash or reagent addition needles 106 for each of the test tubes. The paired fluid pickup needles 102 and wash or reagent addition needles 106 are held in position by housing 108.

Figure 12:
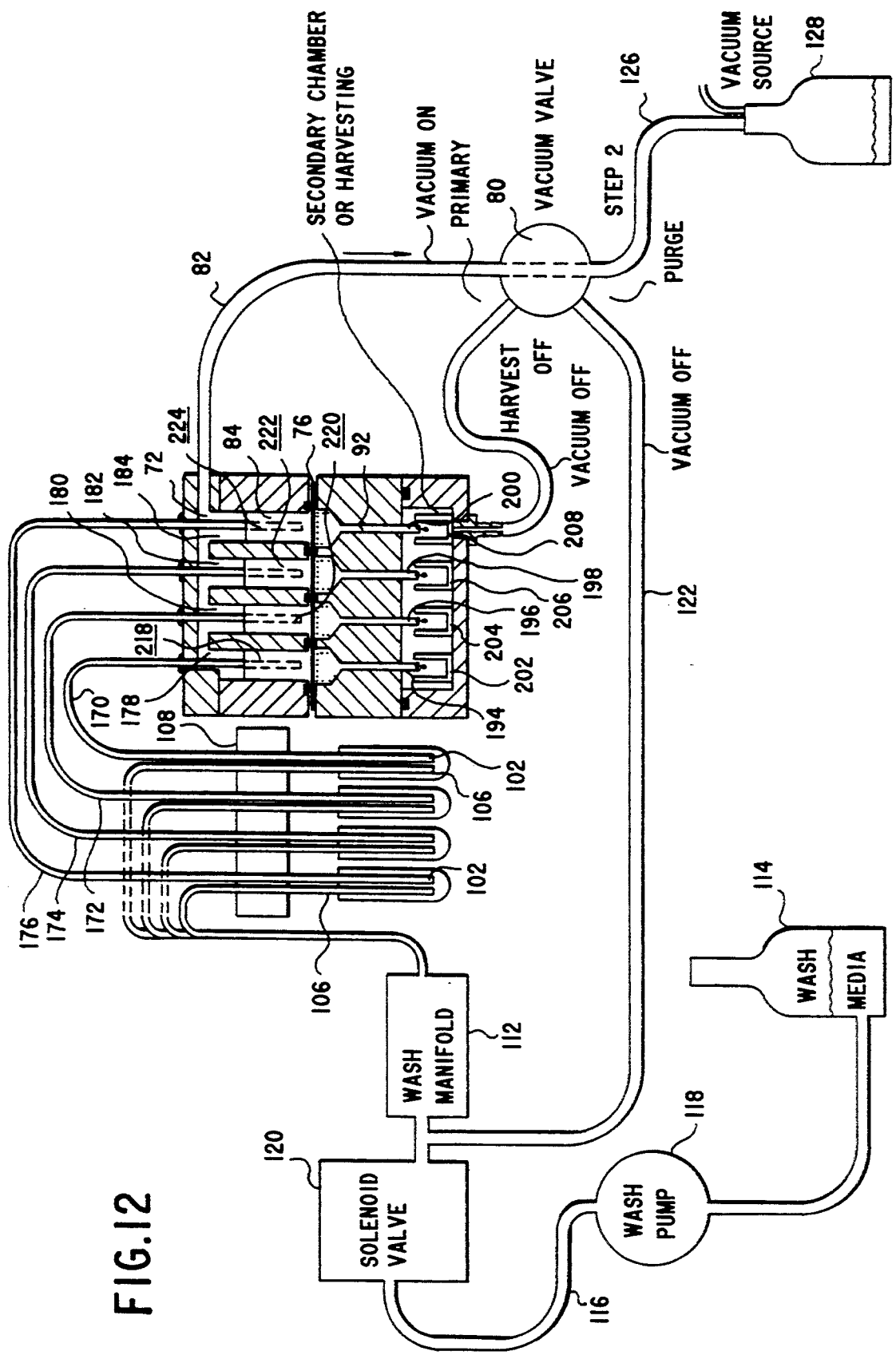
FIG. 12 is an illustration similar to FIG. 11 illustrating the transfer of fluids from the separate test tubes without cross-contamination in accordance with the invention.
Figure 13:
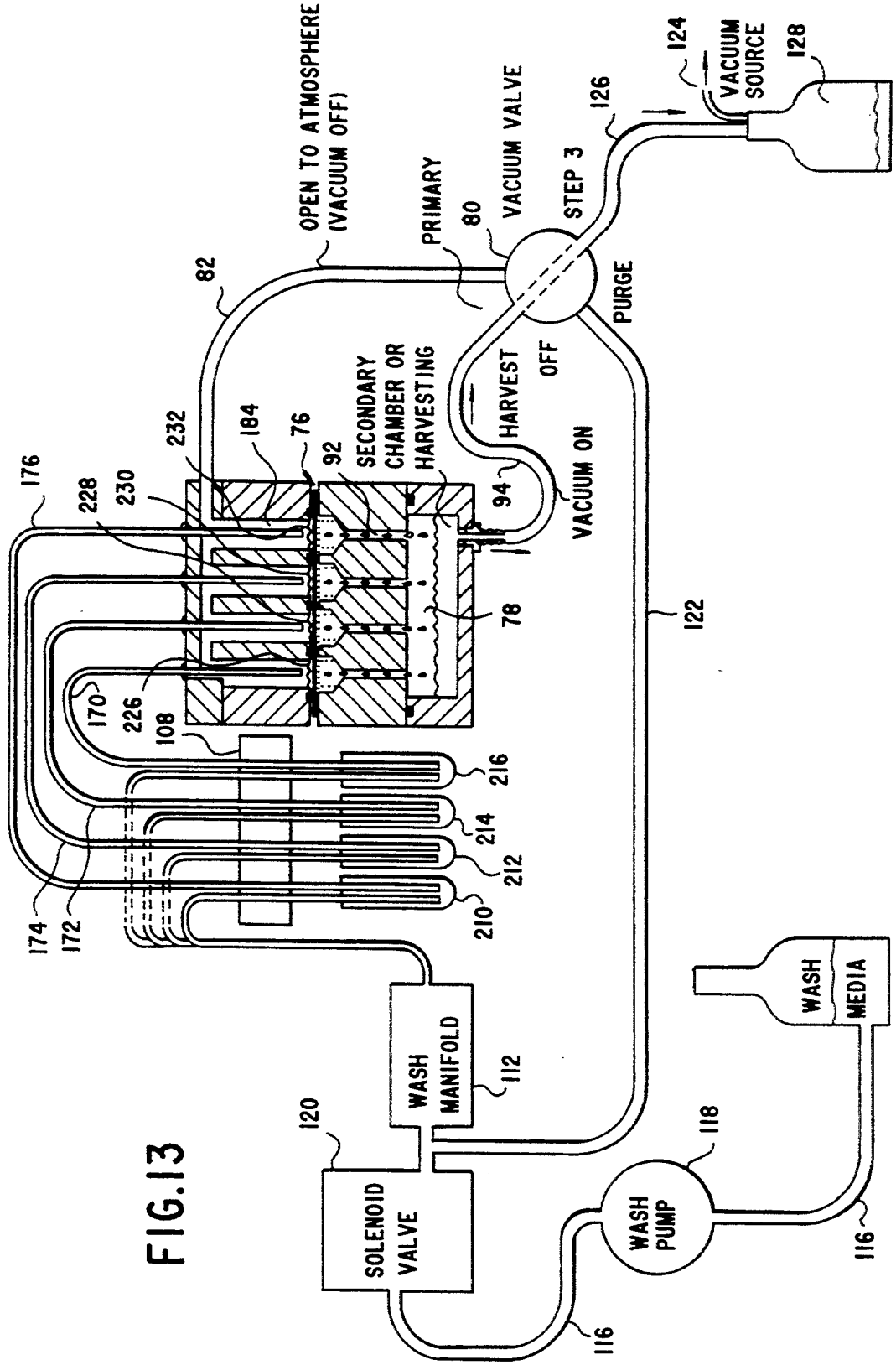
FIG. 13 is an illustration similar to FIG. 11 illustrating the filtering or harvesting of the multiple discrete samples without cross-contamination in accordance with the invention.
Figure 14:
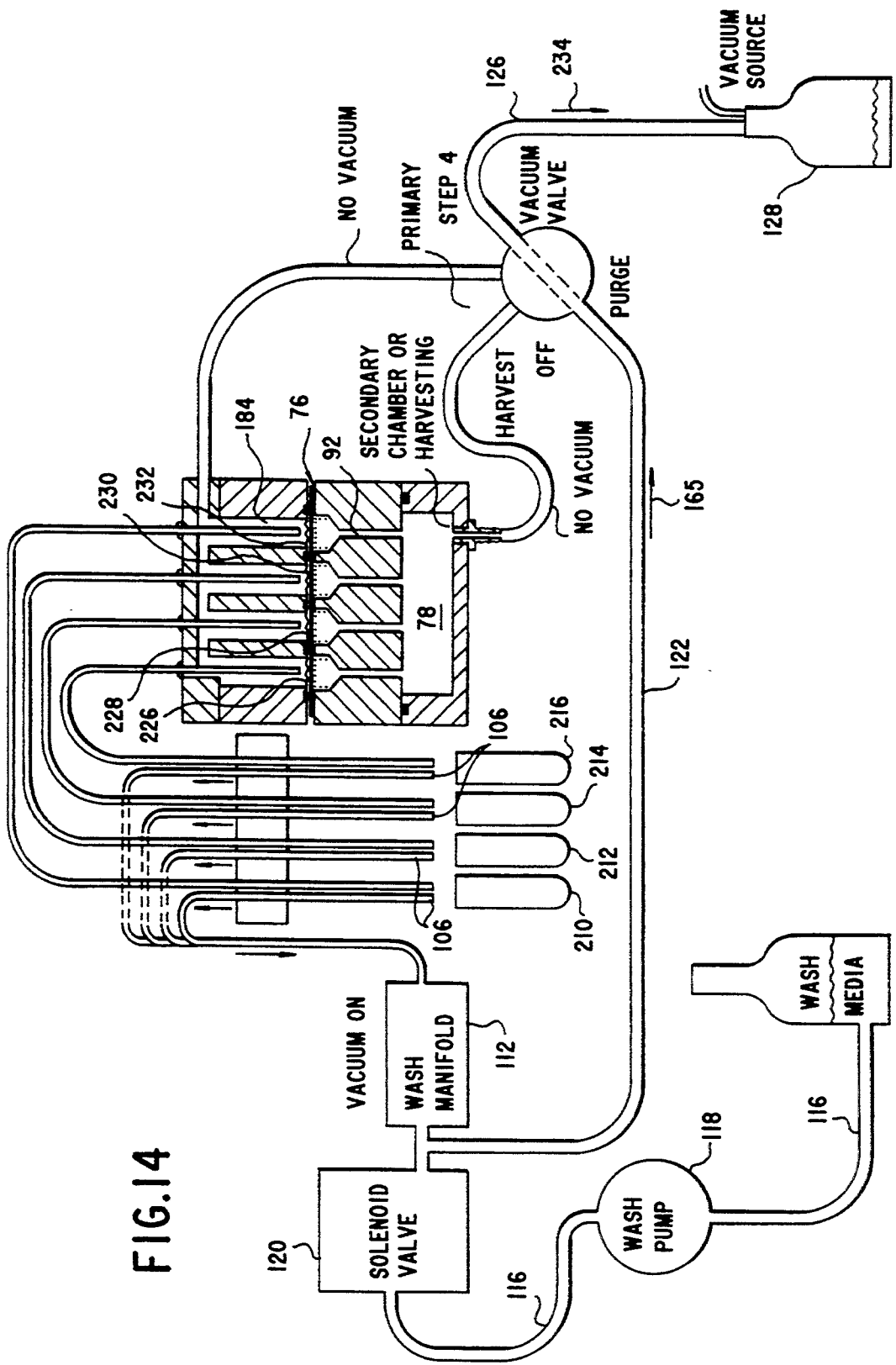
FIG. 14 is an illustration similar to FIG. 11 illustrating the purging of the apparatus in accordance with the invention.

Once the four test tubes 210, 212, 214 and 216 are in place (FIG. 11) the multiposition vacuum valve 80 is moved to the PRIMARY position to introduce a vacuum to conduit 82 to evacuate the first manifold 72 resulting in the transfer of each of the respective separate fluids 218, 220, 222 and 224 to each of the separate separation chambers 178–184 (FIG. 12). Once the four separate fluids 218, 220, 222 and 224 are in the respective separate separation chambers 178–184 the gaseous components of fluid 218, 220, 222 and 224 as well as air drawn through the conduits 170–176 and from the test tubes 210–216 is removed by conduit 82 through first manifold 72.

After the removal of the gaseous component of all the transferred fluids the multiposition vacuum valve 80 is then moved from the PRIMARY to the HARVEST position (FIG. 13) which results in the introduction of a vacuum to the second manifold 78 resulting in each of the liquids 218, 220, 222 and 224 being drawn into the second manifold 78 or into separate containers 202, 204, 206 and 208 provided for the second manifold 78. The filtrable substances 226, 228, 230 and 232 remain on membrane or filter 76 segregated from each other by means of O-rings 186, 188, 190 and 192. Once all of the liquid component of fluid 218, 220, 222 and 224 has been drawn through the filter 76, valve 80 may be returned to the OFF position or returned to the PRIMARY position to provide for the addition of wash solution to each of the four test tubes 210, 212, 214 and 216.

The test tubes 210, 212, 214, 216 are washed with valve 80 in the PRIMARY position while a switch 164 on housing 108 (FIG. 20) is depressed to open solenoid valve 120 and activate wash pump 118 to pump wash fluid from wash media 114 through conduit 116 to wash manifold 112 and into each of the four separate wash or reagent addition needles 106 and into each of the test tubes 210, 212, 214 and 216 while the wash fluids introduced into each of the test tubes 210, 212, 214 and 216 is drawn through each of the conduits 170, 172, 174 and 176 into the individual separation chambers 178, 180, 182 and 184 to separately wash each of the samples without cross-contamination.

Once the washing has been completed test tubes 210, 212, 214 and 216 are removed from each of the pairs of fluid pickup needles 102 and wash or reagent addition needles 106, the vacuum valve 80 is moved to the HARVEST position (FIG. 13) to draw the wash fluid into second manifold 78 and remove the wash fluid from the second manifold through conduit 94 and conduit 126 to trap reservoir 128. Thereafter valve 80 is moved to the PURGE position (FIG. 14) to result in the application of vacuum to conduit 122 to remove wash solution from each of the wash or reagent addition needles 106 drawing the wash solution back into wash manifold 112 and back through conduit 122 to trap reservoir 128 in the direction of arrow 165 and arrow 234. Once this is completed multipositional valve 80 is returned to the OFF position as indicated in FIG. 15.

After washing additional fluids or reacting agents may be introduced to the filtered substances 226, 228, 230 and 232 captured in or on the membrane or filter 76. As will also be recognized by those skilled in the art heating and cooling may be provided to layers 86 and 88 by utilizing heating baths or elements to provide desired reaction temperatures and conditions for further treating filterable substances 226, 228, 230 and 232 captured by the membrane or filter. The heating or cooling elements may or may not be controlled by timers or computers to further provided advantages to the high speed multifunctional filtration devices constructed in accordance with the invention.

Figure 15:
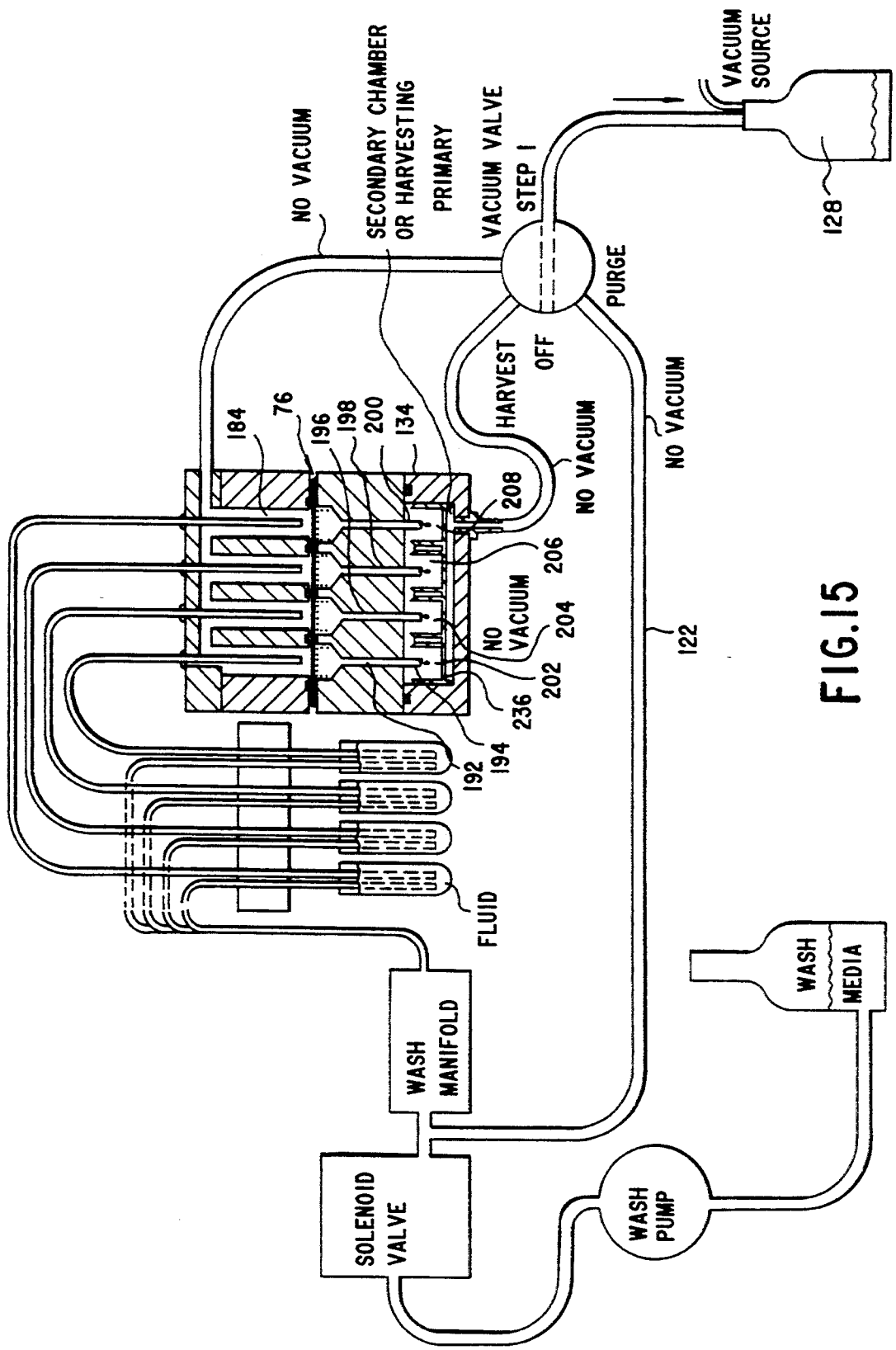
FIG. 15 is an illustration similar to FIG. 11 illustrating the separate addition of wash fluids or reagents to each of the individual test tubes.

Referring now to FIG. 15 the importance of detachably securing bottom layer 134 to layer 88 is illustrated since such detachable securement and optional additional space in the second manifold allows the addition of tray to support each of the separate collection tubes 202-208 where the collection of the filtrate is necessary for analytical or test purposes or where the filtrate includes hazardous or radioactive materials. In such cases the rapid and easy removal of the fourth layer 134 is desired since the removal of the separate tubes 202-208 may be desirable to allow the collection of wash and other reagents while at the same time providing rapid and easy access for the removal and replacement of the fourth layer.

Figure 16:
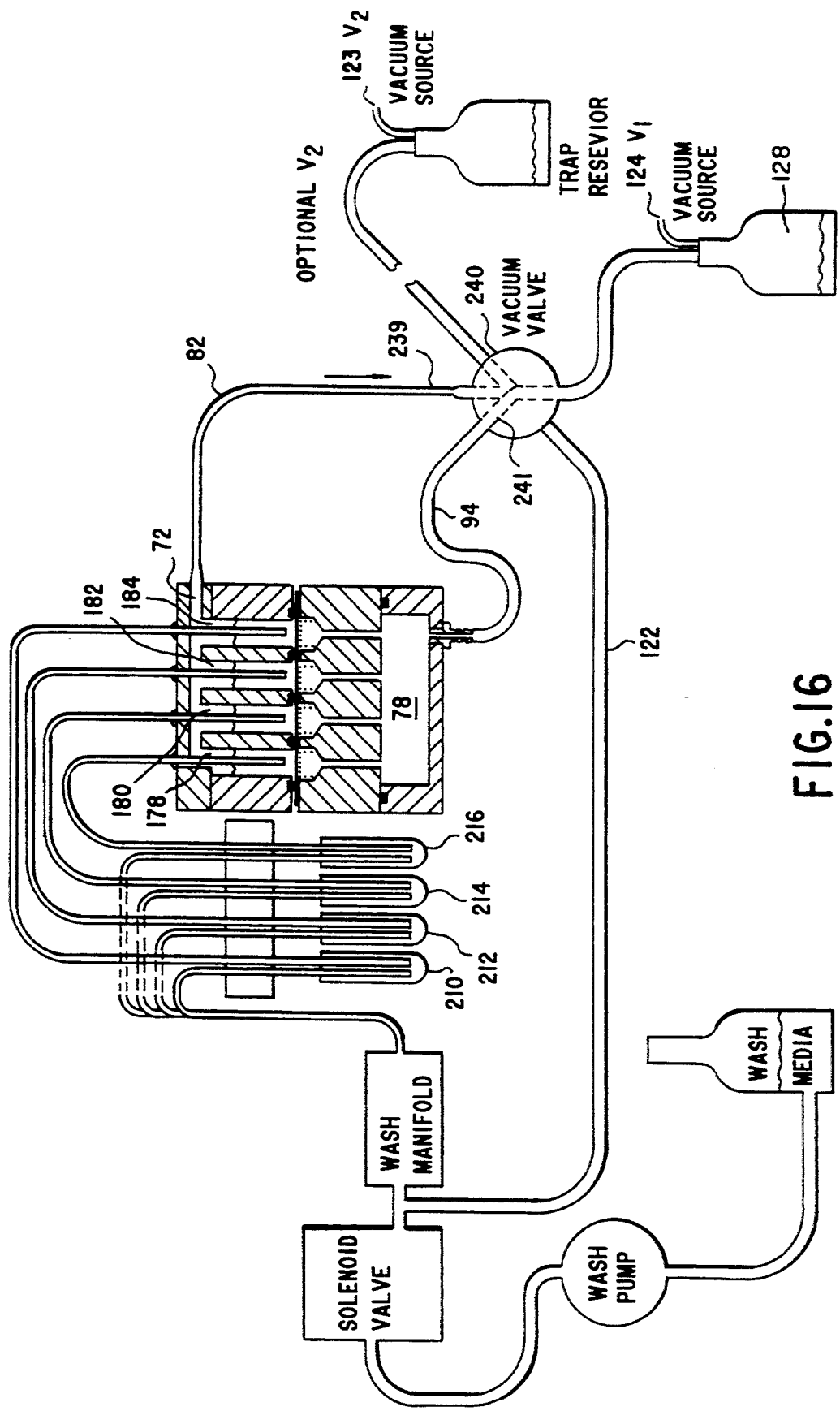
FIG. 16 is an illustration similar to FIG. 11 illustrating an alternative embodiment of the valve of the novel multifunctional filtration apparatus to provide for the simultaneous transferring and filtering in one operation along with the optional provision of two vacuum sources $V_1$ and $V_2$ in accordance with the invention.

Referring now to FIG. 16 a further modification of the invention is illustrated wherein multiposition vacuum valve 80 has been substituted with a dual vacuum port valve 240. The purpose of dual vacuum port valve 240 is to simultaneously introduce vacuum to both the first manifold and second manifold instead of the alternative application of vacuum to the first manifold and then to the second manifold as has heretofore been discussed with respect to FIGS. 11-15. In the modification illustrated in FIG. 16 dual vacuum port valve 240 simultaneously allows vacuum to access both the primary conduit 82 and harvest conduit 94 so that transfer, separation and filtration occur in a single step. Vacuum port valve 240 as illustrated in FIG. 16 allows the transfer of fluids from test tubes 210, 212,214 and 216 into separation chambers 178-184 where the gas, liquid and filterable materials are simultaneously separated in the separation chamber.

In the preferred application of the embodiment utilizing valve 240 a single vacuum source 124 is utilized to provide a vacuum for both conduit 82 and 94. The vacuum provided for chamber 78 by conduit 94 should be greater than the vacuum provided for in chamber 72 by conduit 82 which can be accomplished by making passage 239 of a smaller diameter than passage 241 in valve 240. Alternatively and in some applications where fluids from second manifold 78 should be separated from first manifold due to the toxicity of the materials or for other considerations it may be desirable to utilize two vacuum sources such as vacuum source $V_1$ 124 connected to conduit 94 through passage 241 and vacuum source $V_2$ 123 connected to conduit 82 through passage 239. In such applications it is generally preferable to have the vacuum volume of $V_1$ greater than $V_2$ except where large volumes of gas are to be removed from first manifold 72.

Vacuum port valve 240 allows the gaseous components to be drawn out through manifold 72 via conduit 82 while the liquid portion of the fluid is being be drawn through the membrane or filter medium 76 and the filtrate is captured on an aerophobic or aerophyllic filter is employed in a fairly simultaneous operation. The dual vacuum port valve 240 may be advantageously employed where a continuous filtering process is desired or where substantial amounts of gaseous components such as carbonated fluids are being utilized which require a fairly steady or constant removal of large volumes of fluids with small volumes of filterable materials. In addition it will be appreciated by those skilled in the art that dual vacuum port valve 240 can be constructed so that either the harvest or primary ports open and close as needed during the filtration process especially where two separate vacuum sources $V_1$ and $V_2$ are employed to make certain the gaseous component of the fluid is separated from the liquid component prior to the filtration and separation of the solid or filtrable component from the liquid component.

Referring now to FIGS. 17-29 the application of the invention to a multifunctional filtration apparatus for transferring, separating and filtering through all types of filter medium whether they are impervious to air or not utilizing 24 separate samples is illustrated in which similar parts have been numbered similar to those described in connection with FIGS. 1 and 11. The multifunctional filtration apparatus 242 of FIG. 17-19 includes a first layer 84, a second layer 86, a third layer 88 and a fourth layer 134 which like the layers in FIGS. 1 and 11 form the first manifold, separation chamber, filter support and second manifold.

The wash pump 118 is not illustrated in FIGS. 17-29 but is connected to conduit 116 remote from apparatus 242. The multifunctional filtration apparatus 242 of FIG. 17 includes twenty-four separate separation chambers and twenty-four pairs of fluid pickup needles 102 and wash or reagent addition needles 106 held in a housing 108. Twenty-four separate conduits 110 are connected at one end to the twenty-four separate wash or reagent addition needles 106. The twenty-four separate conduits 110 are connected at the other end to the wash manifold 112 (FIG. 18) which is connected to solenoid 120 including a solenoid valve connector 454 through conduit 116 to the wash media 114 (FIG. 1). The fluid pickup needles 102 similarly include twenty-four separate conduits 104 which direct fluids received by the pickup needles 102 to a distribution conduit 244 which then distribute the fluid to each of the conduits 104 to 24 separate fluid injectors 96 (FIG. 22) disposed through the first layer 84.

Figure 17:
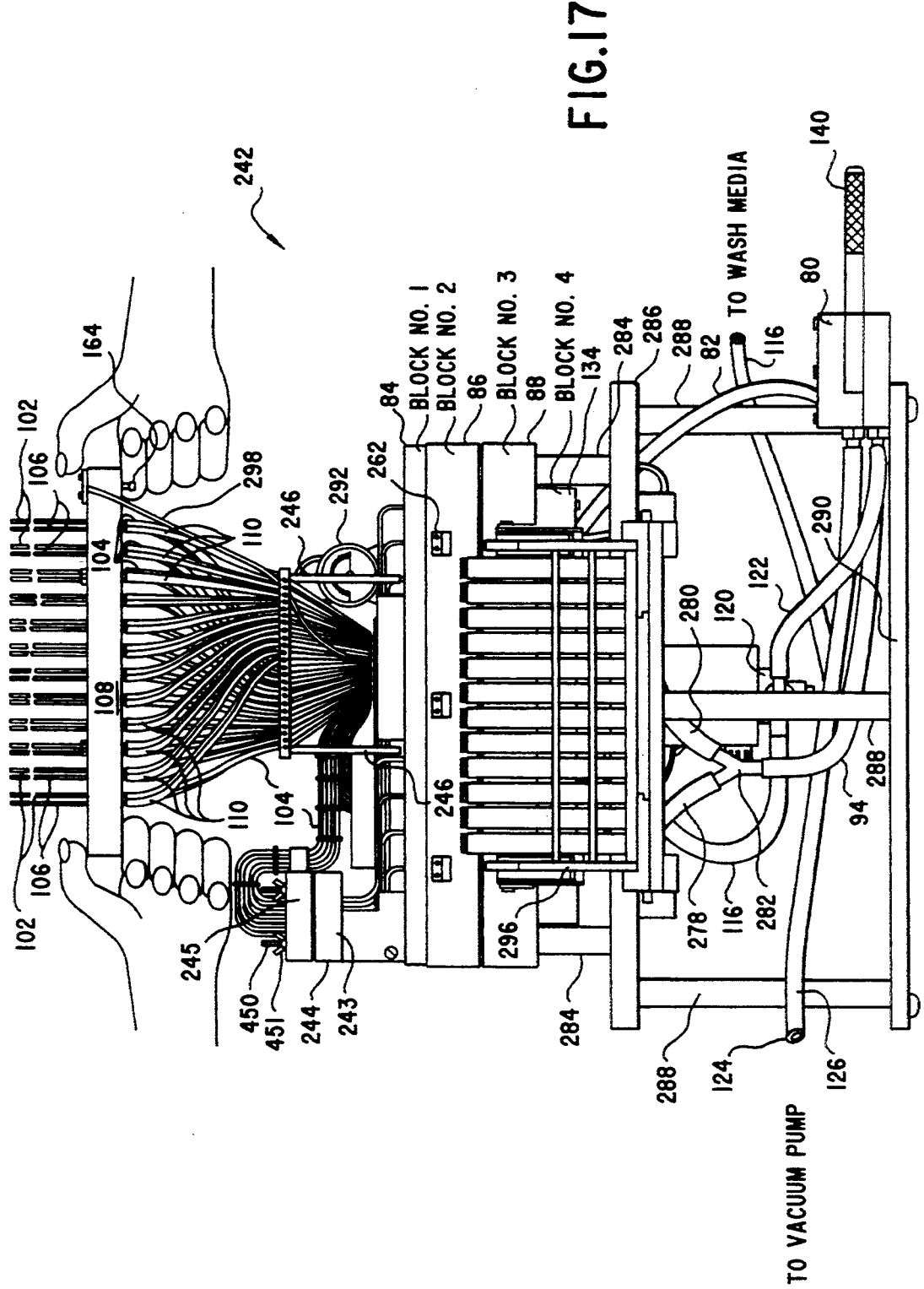
FIG. 17 is a front elevational view of a multifunctional filtration apparatus for handling 24 separate samples constructed in accordance with the invention.
Figure 34:
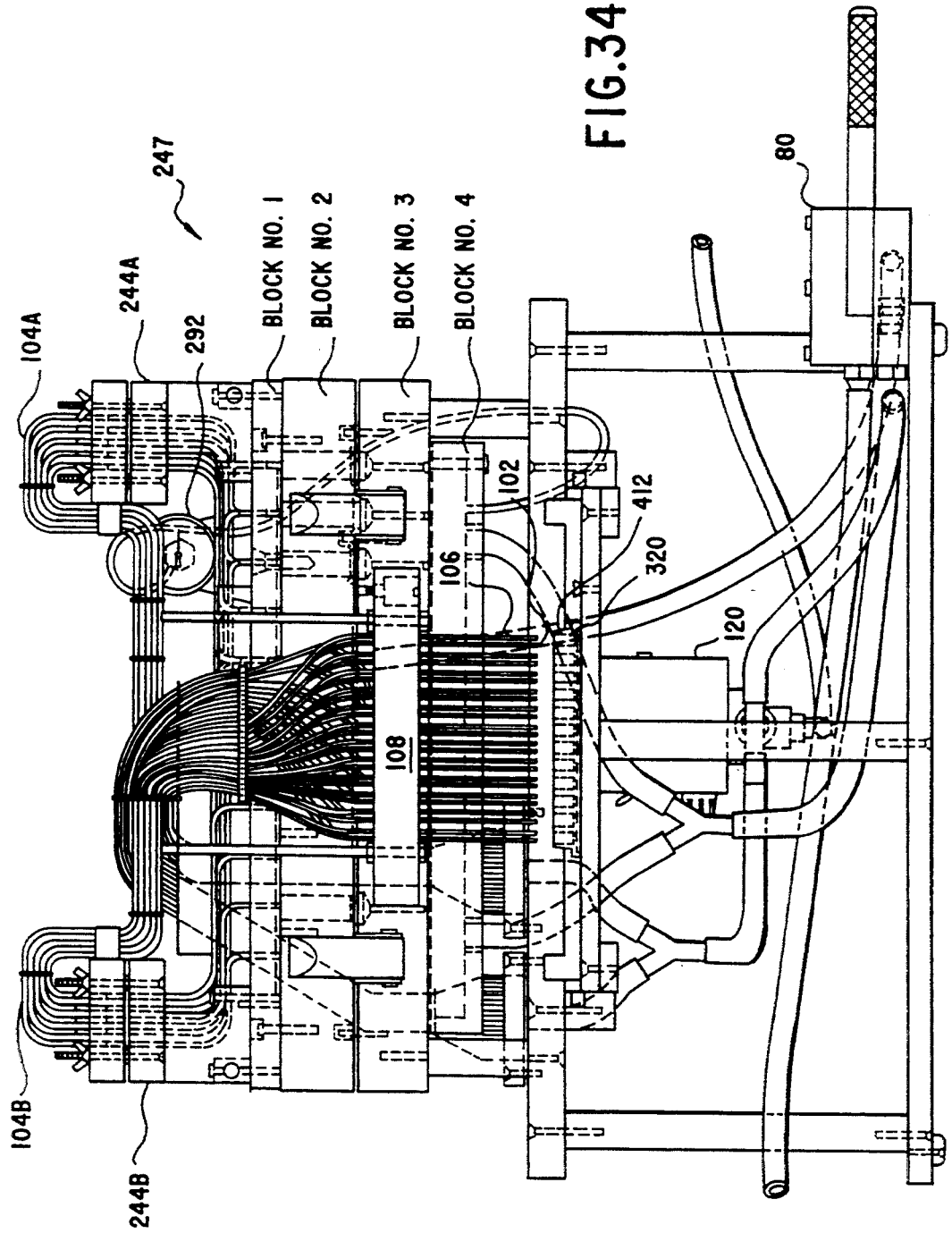
FIG. 34 is a front elevational view partially in phantom of FIG. 30 illustrating the various components and a modification of the wash and evacuation arm for use with micro sample wells.
Figure 37:
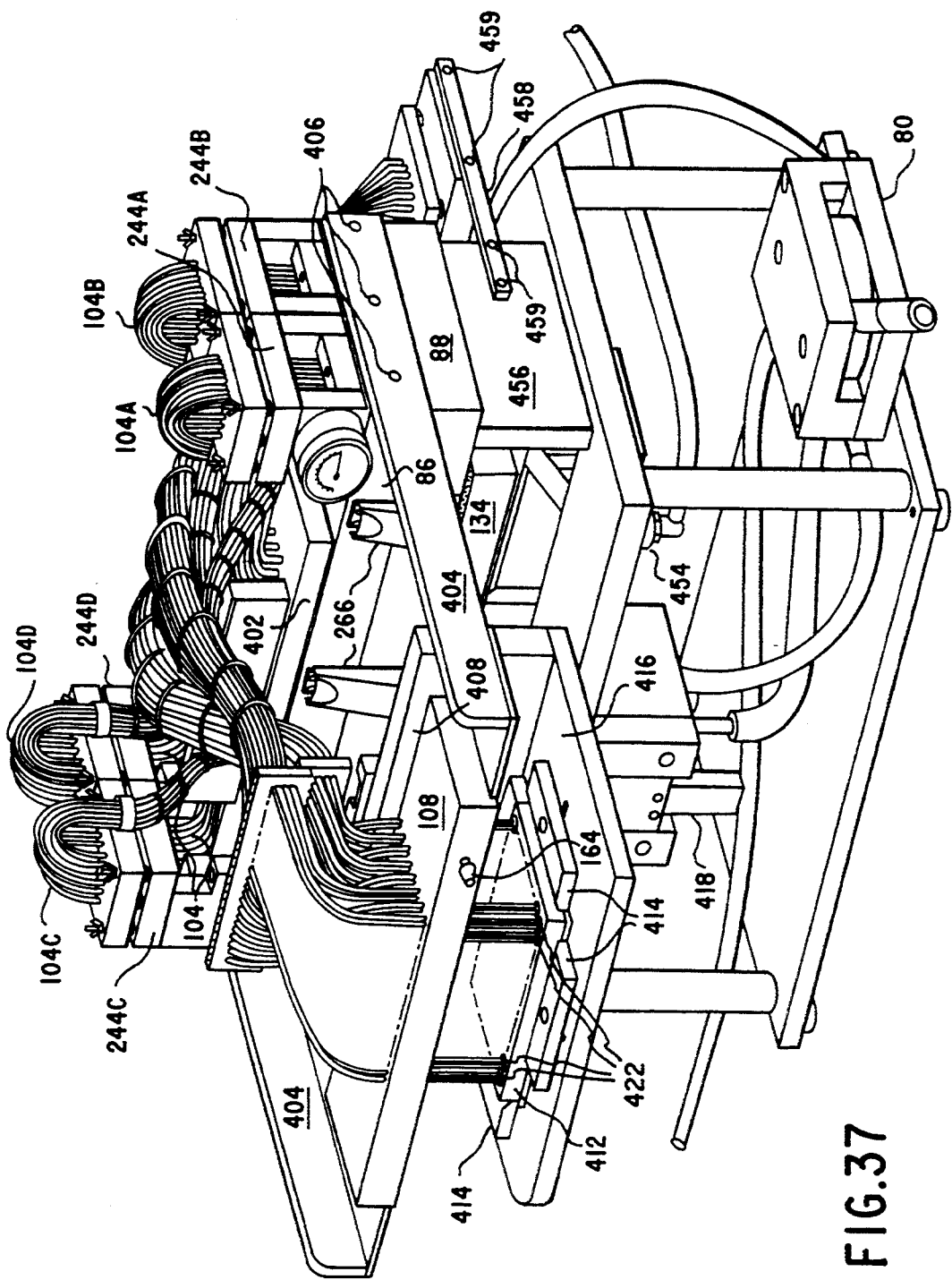
FIG. 37 is a perspective view of FIG. 35 utilizing a 96 well micro sample plate instead of test tubes.

The purpose of the distribution conduit 244 is to assist in channeling the twenty-four separate conduits 104 evenly across the top surface of layer 84 and to make certain all the hoses 104 are of the correct length for purposes of ease of handling housing 108 which is moved manually from its storage position in FIG. 17 to its position of use similar to that shown in FIG. 34. Distribution conduit 244 and wash manifold 112 are each held in place by a series of bolts 450 secured by wing nuts 451 to secure base 243 to plate 245. Plate 113 of wash manifold 112 is similarly attached to base 111 by bolts 450 and wing nuts 451. The separability of plate 113 with conduits 110 and plate 245 with conduits 104 provides for the easy replacement of housing 108 with long needles 102 and 106 to be easily replaced with a housing 108 with short needles 102 and 104 for use with micro sample wells similar to that as illustrated in FIG. 37.

Housing 108 may also include a pair of support rods 246 extending from housing 108 which are designed to fit into holes 248 in layer 84 (FIG. 21). Each of the twenty-four conduits 104 connected to the distribution conduit 244 are cut to individual lengths to connect with the top openings 250 (FIG. 21 and FIG. 22) of each of the fluid injectors 96. The top layer 84 also includes a plurality of openings for bolts or screws 252 for tightly securing layer 84 to layer 86. On the bottom side of layer 84 a first manifold 72 is formed by connecting a groove 254 with each of the injectors 96. A vacuum fitting 256 is provided in layer 84 to connect the first manifold 72 formed by groove 254 with conduit 82 (FIG. 18) and multiposition vacuum valve 80.

The first layer 84 is bolted or screwed to the second layer 86 and a suitable gasket or sealant is utilized fluid-tight connection between layer 84 and 86. The attachment of layer 84 to 86 results in the twenty-four fluid injectors 96 extending down into the twenty-four individual separation chambers 74 in a manner as was similarly described with respect to FIG. 1. The layer 86 (FIG. 24, 25 and 26) includes a number of threaded holes 258 for receiving bolts or screws from the openings for bolts or screws 252 (FIG. 21) for securing the layer together. In addition holes 248 may extend down into the second layer 86 to assist in the support of rods 246 when housing 108 is in its stored position as shown in FIG. 17.

Figure 19:
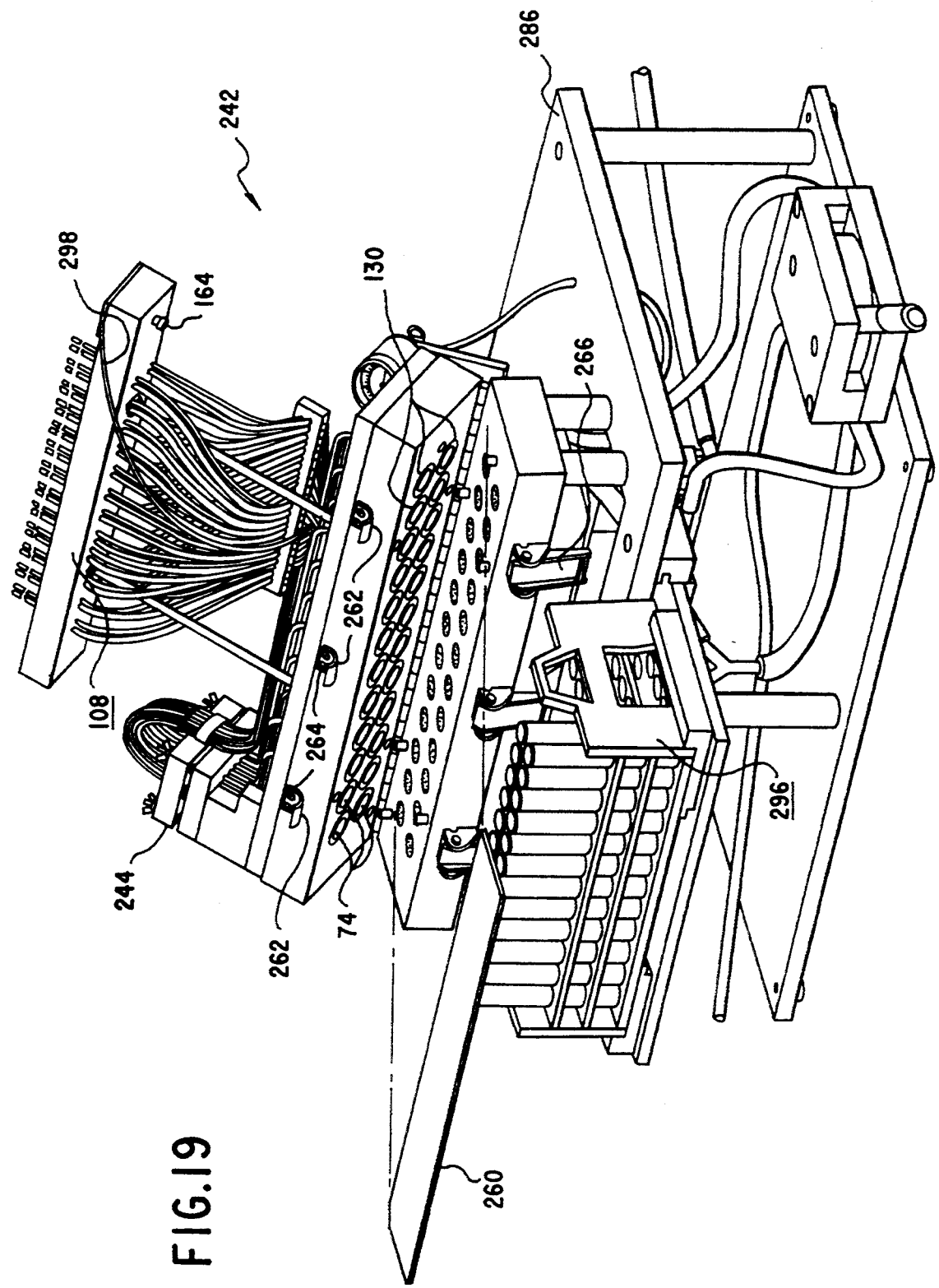
FIG. 19 is a perspective view of the multifunctional filtration apparatus of FIG. 17 illustrating the insertion of the filter medium.

Each of the twenty-four separation chambers 74 formed in layer 86 (FIGS. 19, 24, 25 and 26) terminate in a separate individual O-ring 130 for separating each of the separation chambers from each other when the twenty-four separation chambers are placed in contact with a nitro-cellulose or other filter medium 260 (FIG. 19). Layer 86 also includes latch hooks 262 which are held in place by screws 264 which in combination with latches 266 in layer 88 and hinge 166 provides for the tight closure of layers 84 and 86 against layers 88 and 134 to provide a fluid tight seal. The O-rings 130 surrounding each of the separation chambers 74 further provide a fluid-tight seal around the abutting area of the filter medium 260 to prevent cross-contamination between each of the individual samples transferred from each of the test tubes in test tube rack 296 to each of the twenty-four separation chamber 74 and filtered through filter medium 260.

Block or layer 86 may be either pivoted closed against block or layer 88 by utilizing a hinge 166 or layer 86 and layer 88 may be separated by raising or lowering layer 86 with respect to layer 88 by utilizing support rods (not shown) in which case additional latch hooks 262 and latches 266 should also be utilized in place of hinge 166 to secure layers 86 and 88 together to provide a fluid-tight connection between the upper layer 84 and 86 forming the upper half of the multifunctional filtration apparatus and the lower half of the multifunctional apparatus made up of layers 88 and 134. In either case optional guidance pins 268 may be provided in layer 88 or layer 86 (FIG. 27) for insertion into optional alignment holes 270 which may be disposed in layer 86 or 88 (FIG. 25) to assist in the alignment, positioning and securing of the filter medium 260 between layers 86 and 88.

Block or layer 88 also includes twenty-four individual screens or filter support elements 90 disposed on the top side of block or layer 88 for supporting the filter medium. The bottom side of block or layer 88 terminates in twenty-four channels 92 which may include injectors 194 similar to those described with respect to FIG. 15 where collection of the filtrate is desired. The third layer may also include a number of threaded openings 272 (FIG. 29) for attaching fourth layer 134 which include corresponding holes 274 for attaching layer 134 to layer 88. A seal 132 (FIG. 30) is provided to form an airtight seal between layer 134 and layer 88 and a pair of vacuum opening 276 are provided in the bottom of layer 134 for the attachment of a vacuum fitting 136 for attachment to a pair of conduits 278 and 280 for attachment to a Y-fitting 282 (FIG. 17) which attaches to harvest conduit 94 that is connected to multiposition vacuum valve 80 and vacuum source 124 via conduit 126 as heretofore described with respect to the embodiments in FIG. 1 and FIG. 11.

Figure 18:
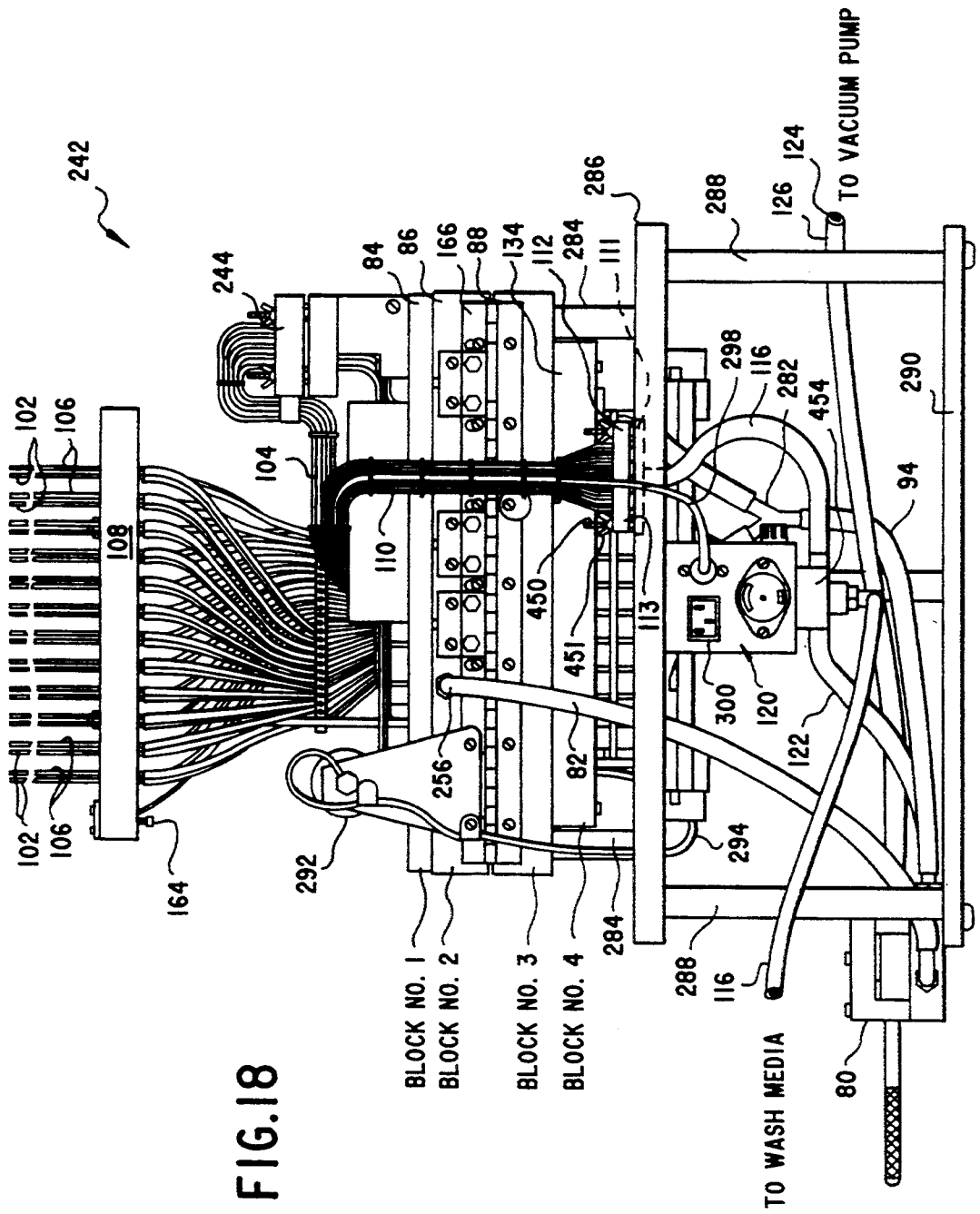
FIG. 18 is a rear elevational view of the multifunctional filtration apparatus of FIG. 17.

The novel high speed filtration apparatus 242 as illustrated in FIG. 18 also includes a conduit 116 connected to the wash media 114 through a wash pump (not shown) similar to that already described with respect to FIGS. 1 and 11. The conduit 116 is interconnected through a solenoid valve connector 454 of solenoid 120 to open and close the valve between conduit 116 to the wash media and conduit 122 to the purge line upon the activation and deactivation of switch 164. Wash manifold 112 is connected via conduits 110 to the individual wash or reagent addition needles 106 to provide wash fluids to the individual test tubes as has previously been described with respect to FIGS. 1 and 11.

The purpose of using Y-fitting 282 and conduits 278 and 280 with vacuum holes 276 is to provide a more even distribution of the vacuum in the second manifold 78 formed by layer 134 where a large number of fluid pickup needles 102 are utilized. In larger embodiments of multifunctional filtration devices constructed in accordance with the invention more than two vacuum holes 276 may be provided in the second manifold 78 to more evenly distribute the vacuum pressure in the space defining the second manifold 78 in the bottom layer 134.

The novel multifunctional filtration apparatus may be supported by a stand having a pair of uprights 284 for supporting layers 84, 86, 88 and 134. The pair of uprights 284 may be further supported by platform 286 which may itself be supported by four support rods 288 as well as a bottom 290 which form a housing for the valve 80, solenoid 120 as well as the conduits 82, 94, 122 and 126. An optional vacuum gauge 292 may also be provided having a line 294 connected to the second manifold 78 for reading vacuum pressure. Alternatively two optional vacuum gauges may be provided particularly where two vacuum sources are provided as heretofore discussed with respect to FIG. 16 for reading pressures in the first manifold 72 and the second manifold 78. Platform 286 can also be used to provide support for a rack of test tubes 296 which contain twenty-four or forty-eight test tubes from which filtrable fluids will be transferred from twenty-four test tubes to the individual separation chambers 74 for separation of the gaseous and fluid components before filtration of the filtrable substances through the filter medium 260.

Figure 62:
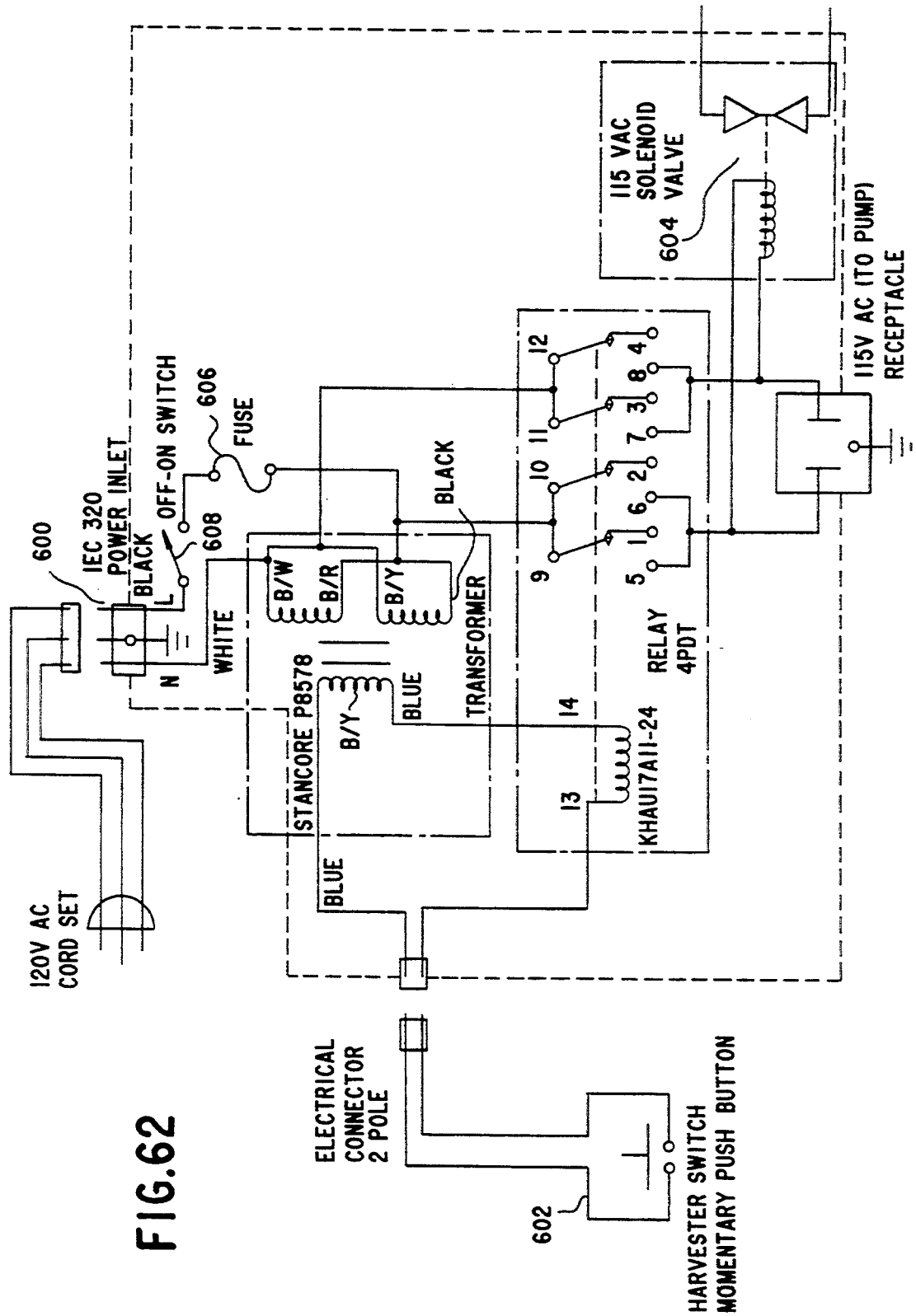
FIG. 62 is an electronic schematic diagram of circuitry which may be utilized in 120 Volt applications in connection with the multifunctional filtration apparatus of the invention.
Figure 63:
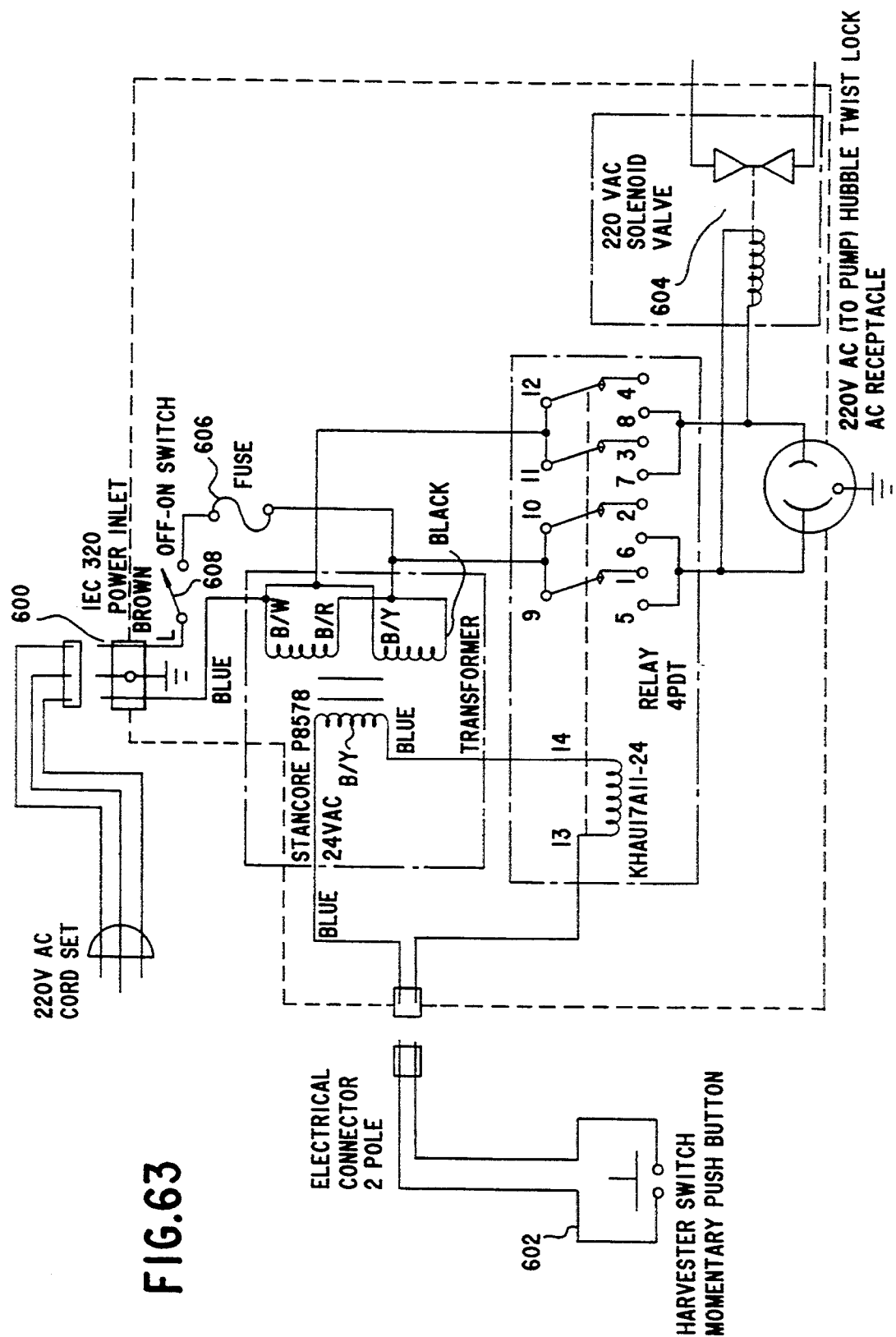
FIG. 63 is a further electrical schematic diagram of circuitry which may be used for 208, 220 or 230 Volt applications of multifunctional filtration apparatus constructed in accordance with the invention.

The multifunctional filtration apparatus 242 also includes a switch 164 connected via electrical line 298 to a solenoid 120 for controlling the wash pump and opening and closing the solenoid valve connector 454 for the introduction of wash fluids into wash or reagent addition needles 106. The solenoid 120 may be mounted to the platform 286 as illustrated in FIG. 18 or remotely mounted with the wash pump. Suitable solenoids for use with the invention may obtained from Valcor Scientific of Springfield, N.J. under the trade designation SV 51C 19 N 34-8. A plug 300 is provided to supply power to the multifunctional filtrational apparatus which may be adapted to run on 115 Volts (FIG. 62) or 208, 220 or 230 Volts as illustrated in FIG. 63.

Referring now to FIGS. 30-34 a multifunctional filtration apparatus 243 capable of transferring, separating and filtering samples from forty-eight individual test tubes is illustrated which is similar to the multifunctional filtration apparatus previously described with respect to FIGS. 1, 11 and 17 in which similar parts have been numbered similarly. The major difference between the multifunctional filtration apparatus of FIG, 17 and 30 is that the multifunctional filtration apparatus of FIG, 30 includes twice as many fluid pickup needles 102 and wash or reagent addition needles 106 and separation chambers 74 as does the multifunctional filtration apparatus illustrated in FIG. 17.

The requirements for handling forty-eight separate samples not only requires forty-eight fluid pickup needles 102 but also forty-eight wash or reagent addition needles 106 in housing 108, The additional pick-up needles can be accommodated with two distribution conduits 244A and 244B each carrying twenty-four of the conduits 104A and 104B which are connected to the forty-eight pick-up needles 102 disposed in housing 108, The two distribution conduits 244A and 244B are connected to bottom plates 243A and 243B to assist in the rapid removal and replacement of housing 108 with long needles for one with short needles as heretofore described as well as for distributing fluids through conduits 104 across the surface of layer 84.

The forty-eight version of the multifunctional filtration apparatus also includes two wash manifolds 112A and 112B (FIG, 31) for supplying wash fluids through conduit 110A and 110B to injector needles 106 in housing 108, The wash manifolds 112A and 112B are connected by conduits 116A and 116B to a Y-fitting 302 which connects wash line conduit 116 to wash manifolds 112A and 112B.

Figure 35:
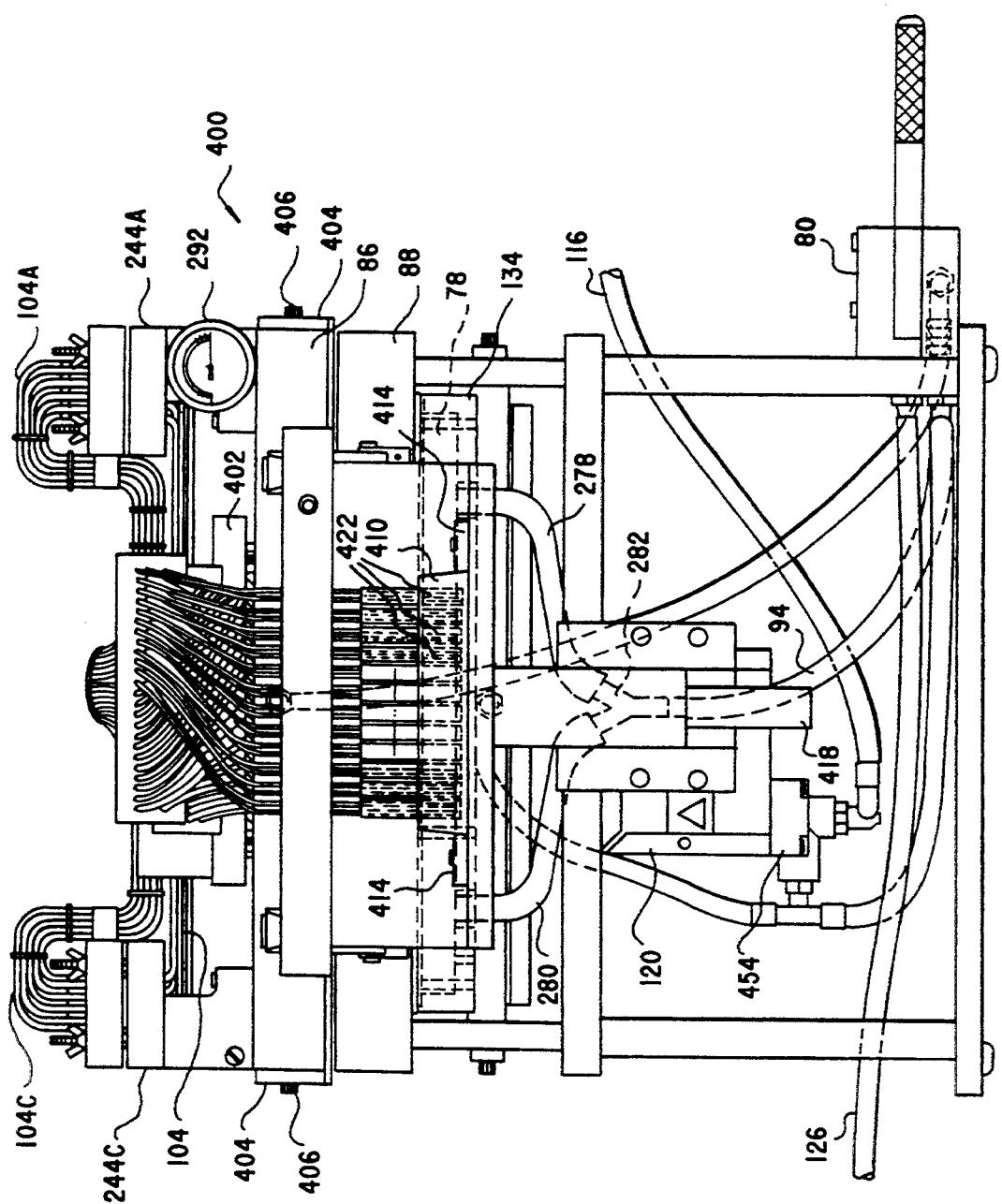
FIG. 35 is a front elevational view partly in phantom of a multifunctional filtration apparatus for transferring and filtering 96 separate samples.

The function and operation of the multifunctional filtration apparatus 243 of FIGS. 30-34 is similar to that previously described except the multifiltration apparatus 243 includes forty-eight separate separation chambers 74 (FIG. 33) which receive fluids from forty-eight separate injector needles 304 disposed in first layer 84 (FIG. 35). Each of the injector needles 304 are connected by each separate conduit 104 through distribution conduit 244A or 244B to a separate fluid pickup needle 102 similar to conduit 104 of FIG. 1.

Each of the fluid pick up needles 102 when activated by valve 80 in the PRIMARY position introduces vacuum via conduit 82 (FIG. 31) to layer 86 which is connected to layer 84 through a borehole and connecting conduit 308 (FIG. 33) to introduce a vacuum in the first manifold created by the inter connection of all of the grooves 310 in layer 84 to draw fluids containing filtrable substances from each of the forty-eight test tubes contained in test tube rack 312. The removal of the fluids from the forty-eight test tubes to the forty-eight separate separation chambers 74 and on top of filter medium 260 results in the separation of the gaseous component which is withdrawn through the first manifold formed by the grooves 310 through the conduit 82.

Figure 33:
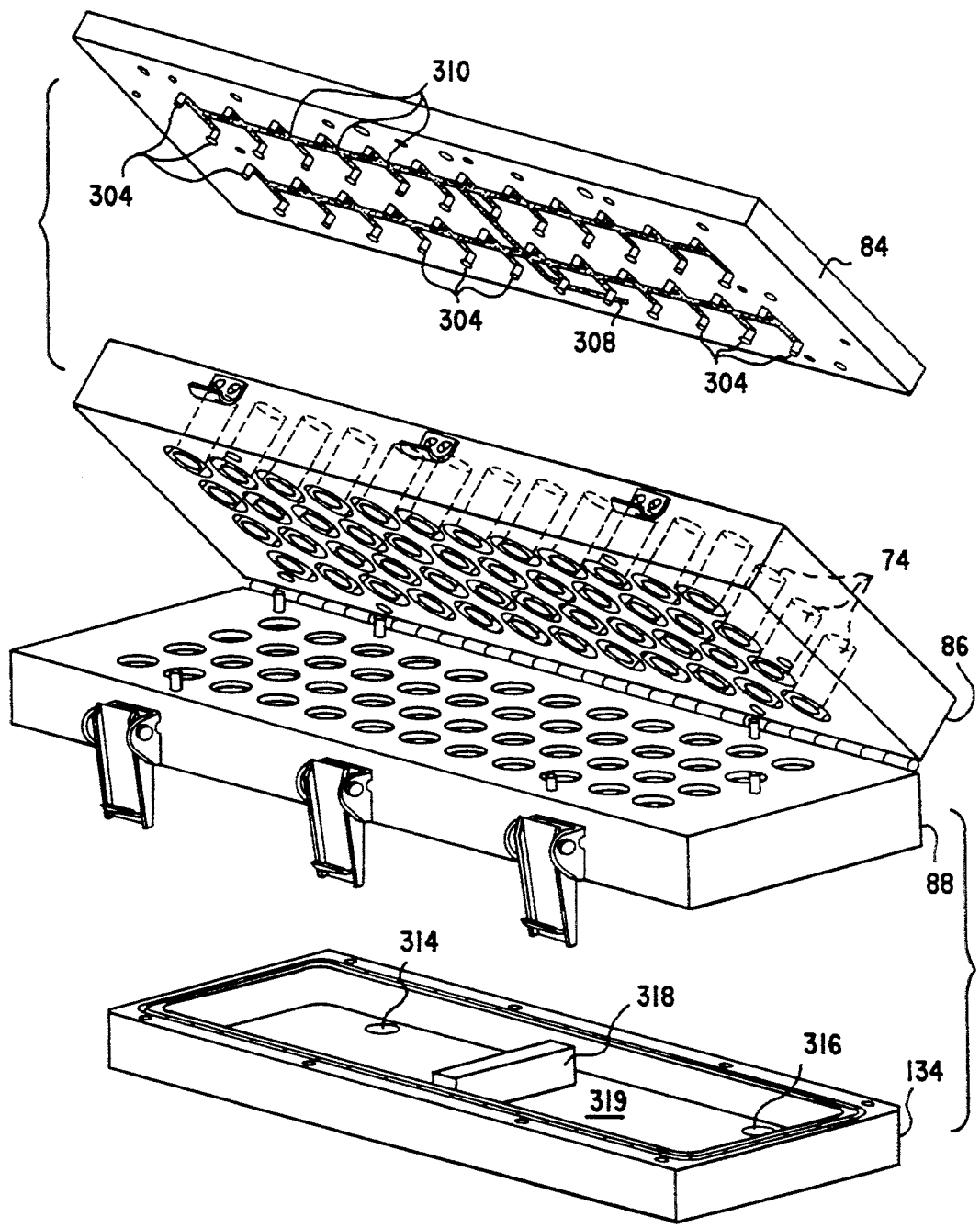
FIG. 33 is an exploded perspective view of the four blocks of the multifunctional filtration apparatus of FIG. 30 illustrating the first manifold, the separation chambers and second manifold.

The liquid and filtrable substances remain in each of the separate separation chambers 74 until the multipositional valve is moved from the PRIMARY position to the HARVEST position at which time vacuum is directed to the second manifold 78 (FIG. 31) by drawing a vacuum through conduit 94 and through Y-fitting 282 to conduits 278 and 280 which are connected to layer 134 through openings 314 and 316 (FIG. 33). The purpose of Y-fitting 282 and conduits 278 and 280 which provides a dual connection with second manifold 78 through holes 314 and 316 is to provide a more even distribution of vacuum in the total area provided by manifold 78 than would otherwise be achieved utilizing a single hole. In addition layer 134 includes a spacing block 318 (FIG. 33) to make certain the vacuum when applied to manifold 78 does not deform the bottom 319 of layer 134 up against the bottom of layer 88. The introduction of vacuum to manifold 78 results in the drawing of the liquid component through filter medium 260 and the collecting of the filtrable substances contained in the liquid on filter medium 260.

Thereafter valve 80 may be moved from the HARVEST position back to the PRIMARY position to once again introduce a vacuum to fluid pickup needles 102 in the manner previously discussed while switch 164 is depressed to open the solenoid valve connector 454 and to activate the wash pump to pump wash fluid through conduit 116 through Y-fitting 302 and into conduits 116A and 116B to wash manifold 112A and 112B and through each of the twenty-four conduits 110A and 110B to wash or reagent addition needles 106 into the test tubes in rack 312 while fluid pickup needles 102 pick up the wash fluid being introduced into the forty-eight test tubes and direct the wash fluid through conduits 104A and 104B and the distribution conduit 244A and 244B and the conduit 104 separately into the respective forty-eight injector needles 304 and into the forty-eight respective separate separation chambers 74. In the forty-eight separate separation chambers the wash fluids and gases drawn through the needles 102 and conduits during the transfer are separated into liquid and gaseous components of the fluid by once again removing the gaseous component through the grooves 310 forming the first manifold 72 and out through conduit 82.

The wash fluids and any materials removed by the forty-eight pickup needles 102 and washed through the forty-eight separate conduits 104 and injector needles 304 are filtered into filter medium 260 by moving valve 80 from the PRIMARY position back to the HARVEST position to introduce vacuum to manifold 78 in a manner similar to that previously described with respect to the initial filtering operation.

Once the samples have been transferred and collected onto filter medium 260 subsequent washing and reacting with various other reagents may take place by either introducing test tubes or a large vessel to the pick-up needles 102 or substituting the desired reagent for the wash media bottle 114 and allowing the desired reagents to be successively added or reacted on the materials collected in the filter medium 260 without the introduction or drawing through of air onto the filter medium 260 by utilizing the first manifold to remove all gas components through the first manifold. Once all the washing and reacting is completed without the introduction of air into the filter medium 260 valve 80 is moved to the PURGE position thereby opening the vacuum to conduit 122 which closes the valve in solenoid valve connector 454 to allow fluids to be drawn back from wash or reagent addition needles 106 and the twenty-four separate conduits 110A and 110B (FIG. 31) as well as the wash manifolds 112A and 112B back through conduits 116A and 116B and conduit 116 to assure the removal of residual wash materials or reagent materials from wash or reagent addition needles 106 before the valve 80 is returned to the OFF position. The purge of the novel multifiltration apparatus allows the removal of all wash fluids or reagents from the conduit supply lines to prevent unwanted addition of fluids to a new set of samples or for subsequent filtration operations.

Figure 31:
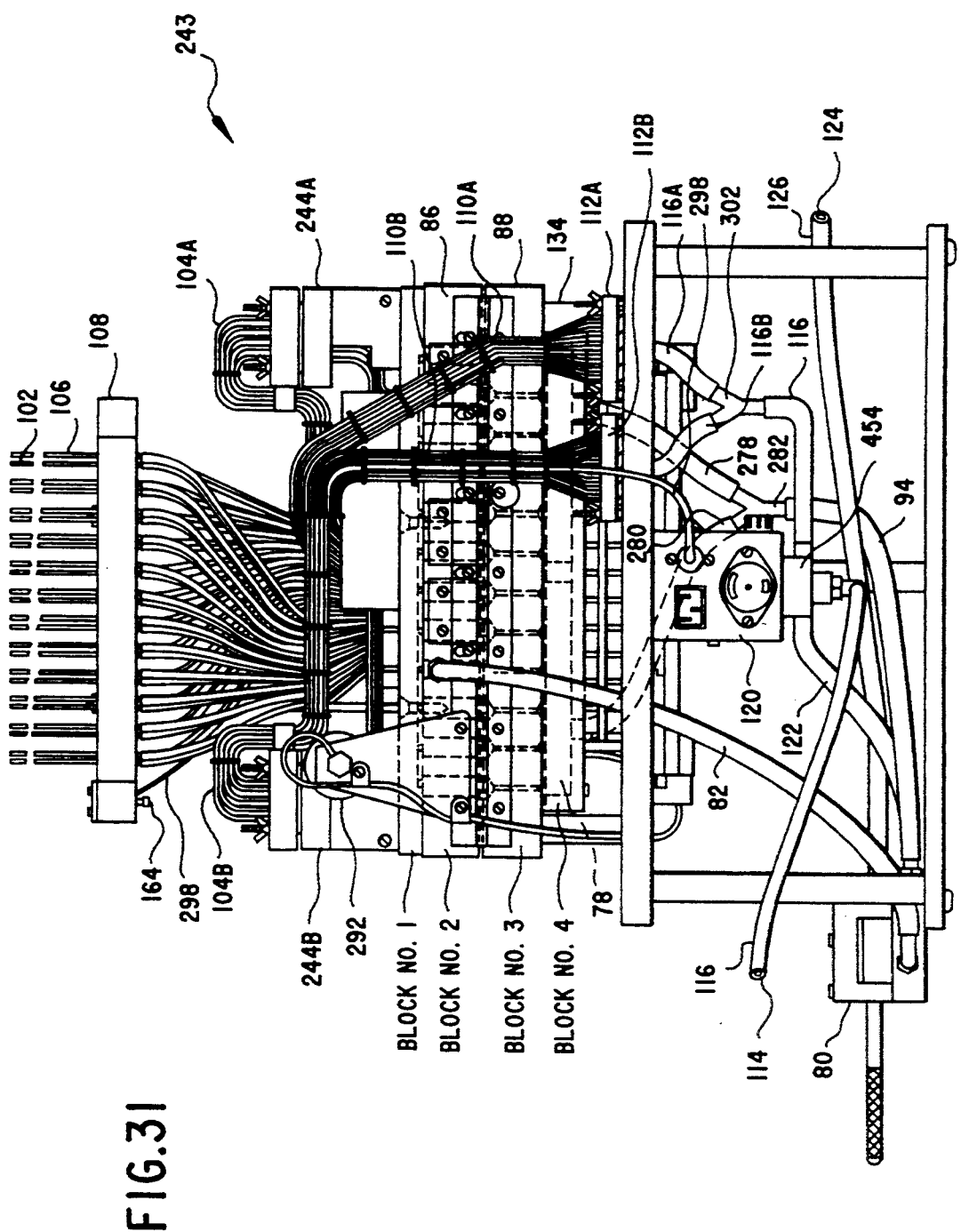
FIG. 31 is a rear elevational view of FIG. 30 partly in phantom.
Figure 32:
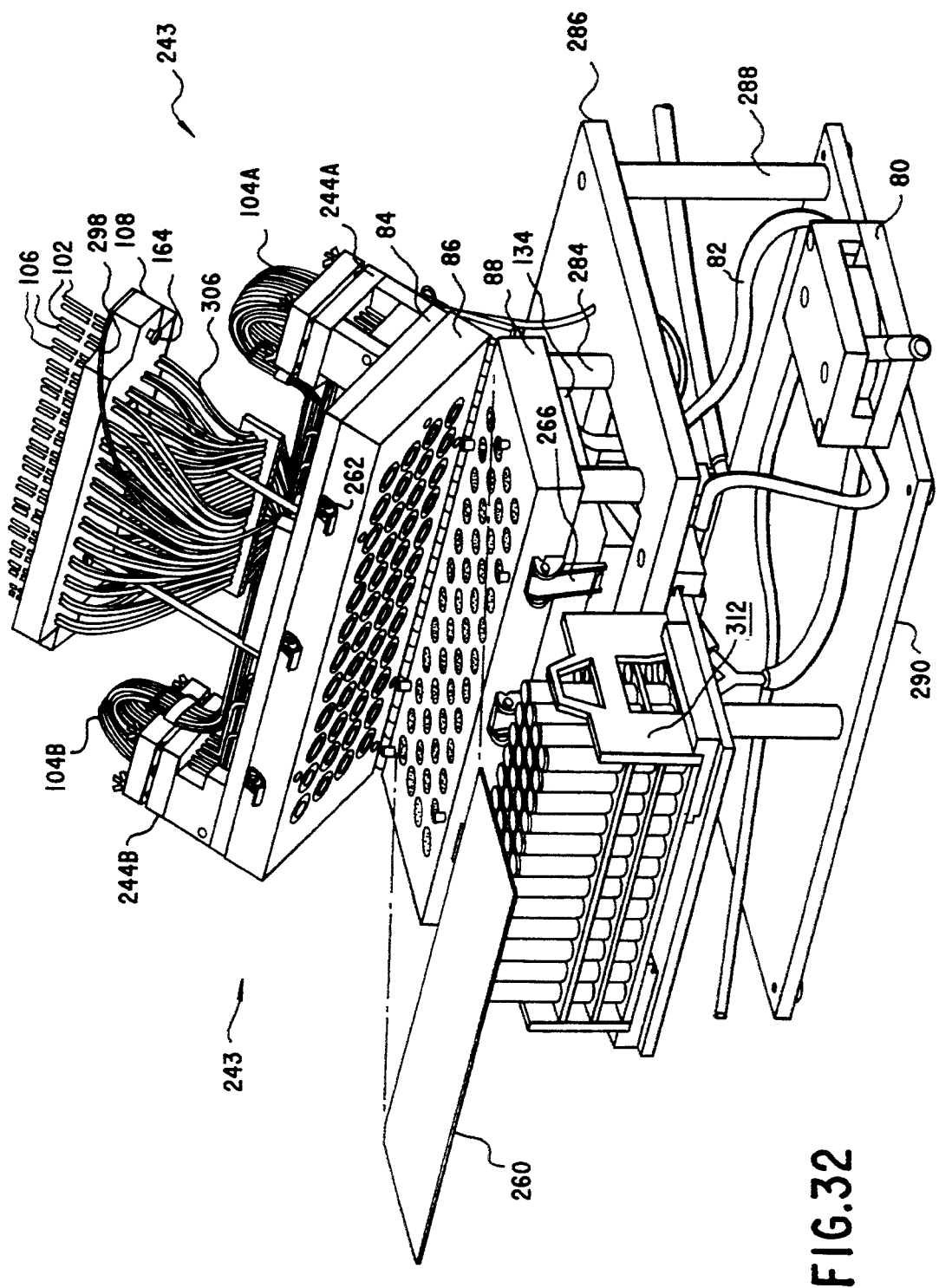
FIG. 32 is a perspective view of the multifunctional filtration apparatus of FIG. 30 opened and partially exploded to illustrate the addition of filter paper.

The multifunctional filtration apparatus 247 as illustrated in FIG. 34 is similar to the cell harvester 243 as illustrated in FIGS. 31–33 except for a minor modification in the fluid pickup needles 102 and wash or reagent addition needles 106. In all other respects the multifunctional filtration apparatus 243 illustrated in FIG. 34 is similar to the multifunctional filtration apparatus 243 previously discussed with respect to FIGS. 31–33. The housing 108 may remain substantially unchanged except for the possible closer spacing and shortening of fluid pickup needles 102 and wash or reagent addition needles 106. The housing 108 may be modified so that the needles 102 and 106 are arranged in closer proximity to each other and may be of a smaller cross sectional diameter so as to fit into a forty-eight well or one half of the 96 wells of a 96 micro sample plate 320 which is generally used in biological and biochemical assays. In the case of the multifunctional filtration apparatus 247 of FIG. 34 smaller volumes of liquid are traditionally employed so that the length and size of the individual needles are preferably decreased to provide less dead space and volume while at the same time accommodating the smaller openings of the one half or 48 wells of a standard ninety-six well micro sample plate.

In all other aspects of the invention apparatus 243 is the same as apparatus 247 including the separation chambers, first manifold, second manifold and the function and operation of valve 80. The only other optional modification in the case of the multifunctional filtration apparatus is illustrated in FIG. 34 is the utilization of a larger or more powerful wash pump to more precisely deliver small quantities of wash fluid to each of the forty-eight wash or reagent addition needles 106 for washing out samples from each of the forty-eight wells of sample plate 320. Each of the wells of plate 320 include typically about 0.1 to 0.5 mil. volume of the sample which require greater precision in sampling handling. Otherwise all aspects of the operation of the multifunctional filtration apparatus 247 illustrated in FIG. 34 is the same as the multifunctional filtration apparatus of FIGS. 30–34 as heretofore has been described.

Figure 42:
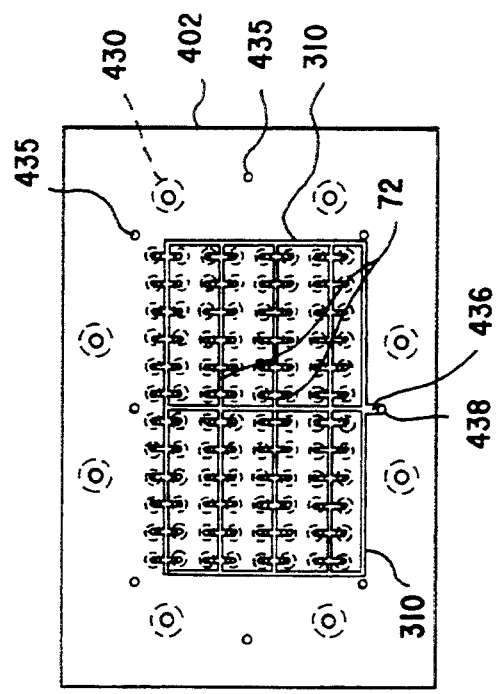
FIG. 42 is a bottom plan view of FIG. 40.
Figure 40:
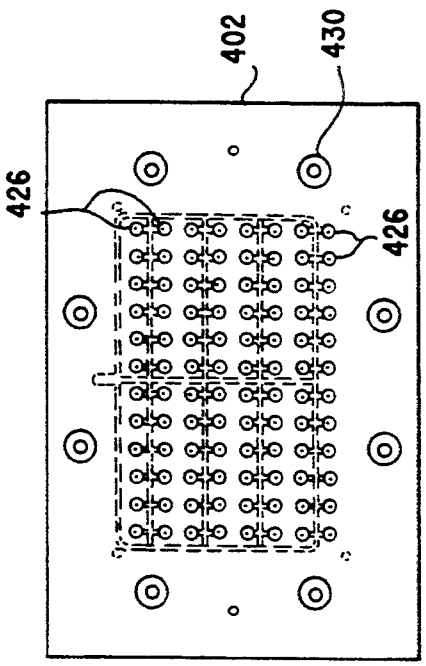
FIG. 40 is a top plan view of the first layer of the novel multifunctional filtration apparatus of FIG. 35.
Figure 41:
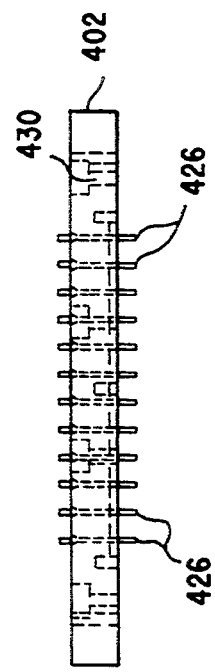
FIG. 41 is a front elevational view partly in phantom of the top plate of FIG. 40.
Figure 46:
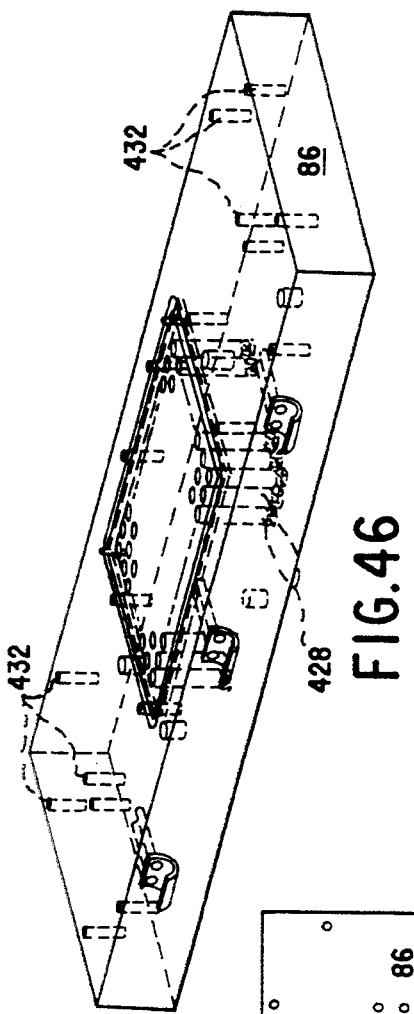
FIG. 46 is a perspective view of FIG. 44.
Figure 47:
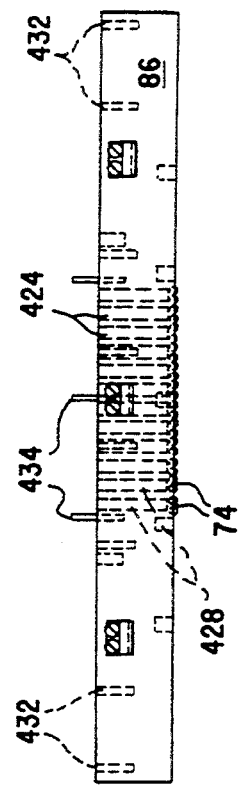
FIG. 47 is a front elevational view partly in phantom of FIG. 44.
Figure 44:
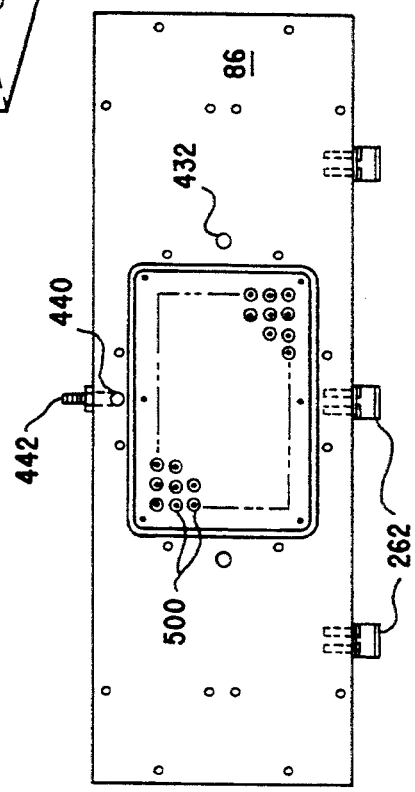
FIG. 44 is a top plan view of the second layer of the novel multifunctional filtration apparatus of FIG. 35.
Figure 45:
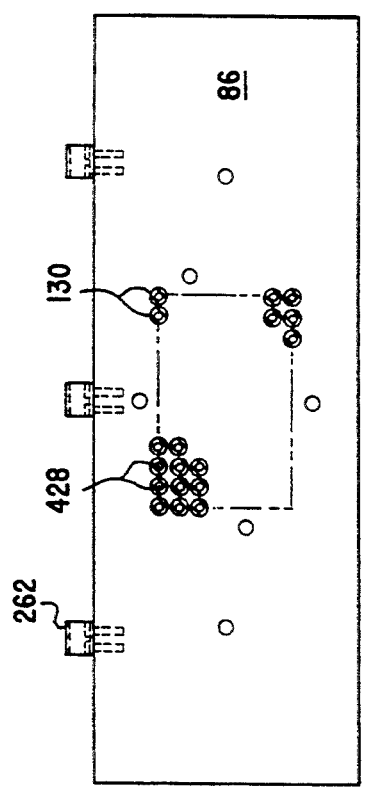
FIG. 45 is a bottom plan view of FIG. 44.

Referring now to FIG. 35, 36, 37 and 38 a multifunctional filtration apparatus 400 is illustrated which provides for the automated transfer of ninety-six separate samples to ninety-six separate separation chambers for the separation of the gaseous and liquid components from the fluid before the separate filtering of the remaining liquid and filtrable component through any type of filter medium. The ninety-six sample multifunctional filtration apparatus 400 is similar to the multifunctional filtration apparatus of FIGS. 1, 11, 17 and 30 as heretofore described and includes the same elements including multiposition vacuum valve 80 with its OFF, HARVEST, PRIMARY and PURGE positions along with associated conduits which connect the first manifold 72 (FIG. 42) formed in a modified first layer 402, a second manifold 78 formed in a fourth layer 134 and ninety-six separate separation chambers formed in the second layer or block 86.

Figure 30:
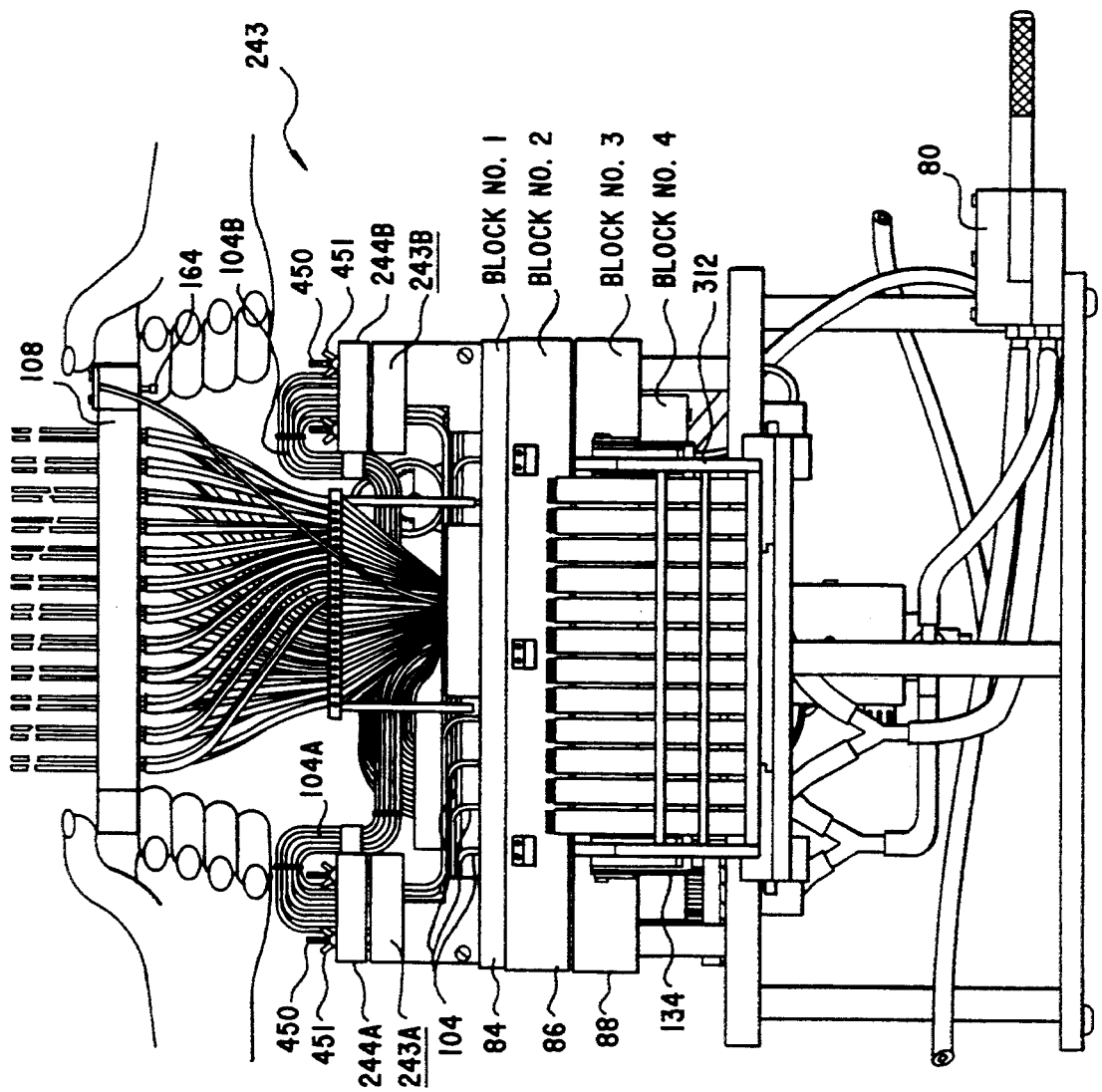
FIG. 30 is a front elevational view of a multifunctional filtration apparatus for transferring and filtering 48 separate samples from test tubes constructed in accordance with the invention.

The third block or layer 88 of multifunctional filtration apparatus 400 serves as a filter medium support similar to those discussed in connection with previous embodiments of the invention but modified to accommodate 96 separate samples. The third layer may be separated from the second layer 86 by means of a hinge 166 (FIG. 36) or other mechanical means. The multifunctional filtration apparatus 400 similarly includes all the previous elements of FIG. 18 and FIG. 30 in which similar elements have been numbered the same. The differences between the embodiments as illustrated in FIG. 30 and FIG. 35 pertains to the difference in the provision for ninety-six separate test tubes or sample wells as opposed to forty-eight with the accompanying addition of the additional number of separation chamber conduits 110, 104, distribution conduits 244 and wash manifolds 112 as well as utilizing ninety-six pickup needles 102 and wash or reagent addition needles 106.

The generally small volumes of liquid employed in such small samples generally about 0.5 mls to 2 mls necessitates a further modification of the needle support housing 108 to include not only the provision for the ninety-six pickup needles 102 and ninety-six wash or reagent addition needles 106 but also their attachment to a support structure such as layer 86 via support bars 404 which may be attached to layer 86 by screws 406. Support bars 404 support a support member 408 for carrying and maintaining the position of housing 108 carrying wash or reagent addition needles 106 and fluid pickup needles 102 with respect to a sample plate or tray 410 for containing ninety-six test tubes or a micro sample tray or plate 412 having ninety-six wells (FIG. 37) which is maintained in registry position by employing a plurality of sliding spacers 414 for positioning the sample tray 410 or micro sample plate 412. Layer 86 may be separated from layer 88 for the addition of any type of the filter medium 260 as is illustrated in FIG. 38. Four optional guidance pins 268 may be utilized to assist in the positioning of filter medium 260 between layer 86 and 88 before the layers are secured together using latches 262 prior to transferring, separating and filtering fluids.

The sliding spacers 414 (FIG. 37) are preferably carried on a tray 416 which can be raised or lowered with respect to support 408 by employing a rod, bar or other slide mechanism 418 which may include a slide or geared assembly for precisely raising and lowering the sample tray 410 or micro sample plate 412 for alignment with the ninety-six fluid pickup needles 102 and ninety-six wash or reagent addition needles 106 carried on housing 108 and supported by support 408. In this manner the fluid pickup needles 102 and injector needles 106 maintain registry with the ninety-six openings 422 in the micro sample plate 412 or the test tubes 424 in tray 410.

The multifunctional filtration apparatus 400 includes four distribution conduits 244A, 244B, 244C and 244D (FIG. 37) each containing twenty-four of the ninety-six conduits 104A, 104B, 104C and 104D and which are connected to twenty-four of the ninety-six fluid pickup needles 102. The distribution conduits 244A, 244B, 244C and 244D evenly distribute each of the twenty-four conduits 104A, 104B, 104C and 104D to ninety-six separate conduits 104 across the top of a modified first layer 402 (FIGS. 40–43) to provide for the even injection through ninety-six separate injectors 426 into the ninety-six separate separation chambers 428 provided in layer 86 (FIGS. 44–47). Layer 402 may be attached to layer 86 by means of bolts tightened through holes 430 provided in layer 402 which are designed to be received by a threaded corresponding hole 432 in layer 86 (FIGS. 40, 45, 46 and 47). Alignment pins 434 may also be provided in the top of layer 86 for alignment with holes 435 in layer 402 to assist in the joining of layer 402 to layer 86. Layer 402 also includes a first manifold 74 created by the interconnection of grooves 310 which connect to a conduit 436 which terminates in an end 438 for mating with a hole 440 in layer 86 which is connected to a fitting 442 for connection to conduit 82 and vacuum valve 80 (FIG. 36).

The ninety-six multifunctional filtration apparatus 400 differs from the forty-eight variety filtration apparatus of FIGS. 31 and 32 by the utilization of four separate wash manifolds 12A, 112B, 112C and 112D which in combination provides wash fluids for ninety-six individual wash or reagent addition needles 106. The four separate wash manifolds 112A, 112B, 112C and 112D (FIG. 36) receive wash fluid through a common manifold 444 which is connected by fitting 446 to conduit 452 which is connected to solenoid valve connector 454 and conduit 122. Each of the separate wash manifolds 112A, 112B, 112C and 112D include twenty-four ports 448 (FIG. 60) for supplying wash fluids pumped into wash manifold 444 through conduit 122 from the wash pump. The four separate manifolds 112A, 112B, 112C and 112D (FIG. 61) include bolts 450 and seals 452 for closing manifold 444 so that wash fluids supplied by wash pump 118 through conduit 116 evenly provides wash fluid to common manifold 444 and each of the four separate manifolds 112A, 112B, 112C and 112D.

Figure 36:
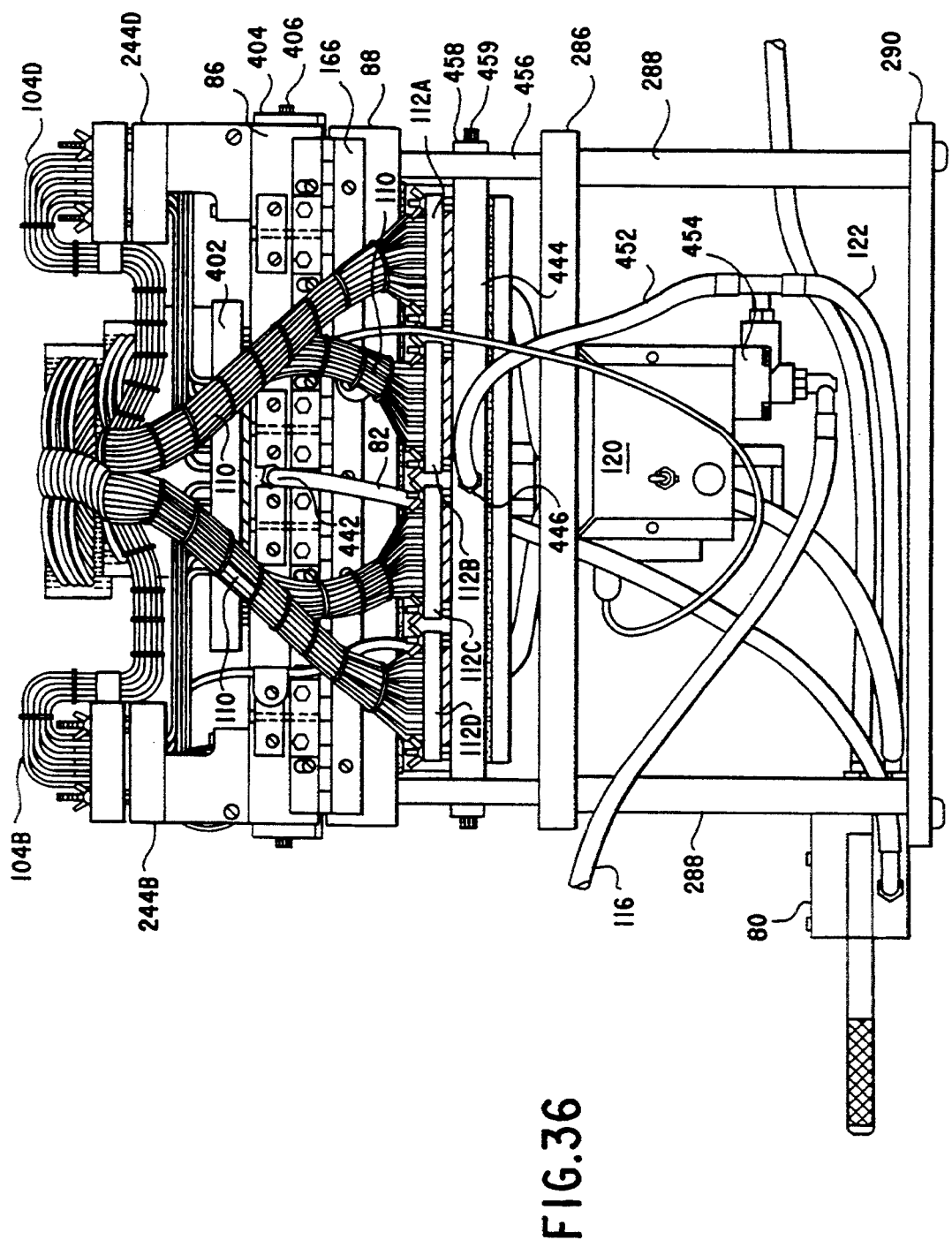
FIG. 36 is a rear elevational view of FIG. 35.

In FIG. 36 the connections to common manifold 444 are such that fluid from wash pump 118 goes through solenoid valve connector 454 and is directed through conduit 452 and into common manifold 444 and to the wash or reagent addition needles 106 when switch 164 as depressed. When switch 164 is not depressed the valve in solenoid valve connector 454 is closed thereby allowing vacuum to be introduced to conduit 122 and draw any wash fluids remaining in wash or reagent addition needles 106 back through the needles and through the ninety-six separate conduits 110 and through the manifolds 112A, 112B, 112C and 112D and through the common manifold 444 and through conduit 452 and conduit 122 to the trap reservoir 128. As a result conduit 452 serves a dual function of not only supplying wash fluid through conduit 116 but also cooperates with the purge conduit for purging fluid through conduit 122.

Common manifold 444 along with the four individual wash manifolds 112A, 112B, 112C and 112D are supported on support members 456 (FIG. 37) by two support brackets 458 held in place by screws 459. The multifunctional filtration apparatus for ninety-six samples like the multifunctional filtration apparatus of FIG. 33 for forty-eight samples is supported by a platform 286 which is supported by four support rods 288 connected to a bottom 290 which provides a base for the attachment of valve 80. In operation the multifunctional filtration apparatus 400 for ninety-six samples operates exactly the same as heretofore described with respect to the one, four, twenty-four and forty-eight varieties of multifunctional filtration apparatus as has heretofore been described. The washing is activated by a wash switch 164 on housing 108 in a manner similar to that heretofore described. The operation and function of the first manifold, second manifold and separation chambers being the same except that each of them includes provision for ninety-six separate samples and test tubes and ninety-six separate separation chambers for the handling without cross-contamination of ninety-six samples.

The major difference between the ninety-six variety of multifunctional filtration apparatus of course is the provision for smaller sized samples along with the smaller size of the filter medium and the smaller size openings 422 of the micro sample plate 412 and the resulting importance of maintaining close tolerances between the fluid pickup needles and injector needles and the test tube and micro sample plate. Also as heretofore described smaller quantities of wash fluids and filterable fluids requires the more precise handling including transfer, separation and filtration along with the requirement for smaller separation chambers due to the smaller quantities of fluids being transferred, separated and filtered in the ninety-six variation of the multifunctional filtration apparatus of the invention. It is also desirable to use the more powerful wash pump described in the forty-eight sample embodiment of the invention to provide for the more even flow and distribution of wash fluids.

Referring now to FIG. 39 a further embodiment of the invention is illustrated where a modified third layer 88 includes a recess 490 for receiving either a micro sample plate with filters 460 or a filter support insert for supporting any type of filter medium 260. In some cases it is desirable to transfer from a micro sample plate 412 and filter samples directly onto a micro sample plate with filters 460 which can be provided with the embodiment as illustrated in FIG. 39 having a recess 490. The micro sample plate with filters also known as filter plates are available from Costar Inc. of Cambridge, Mass.

Figure 52:
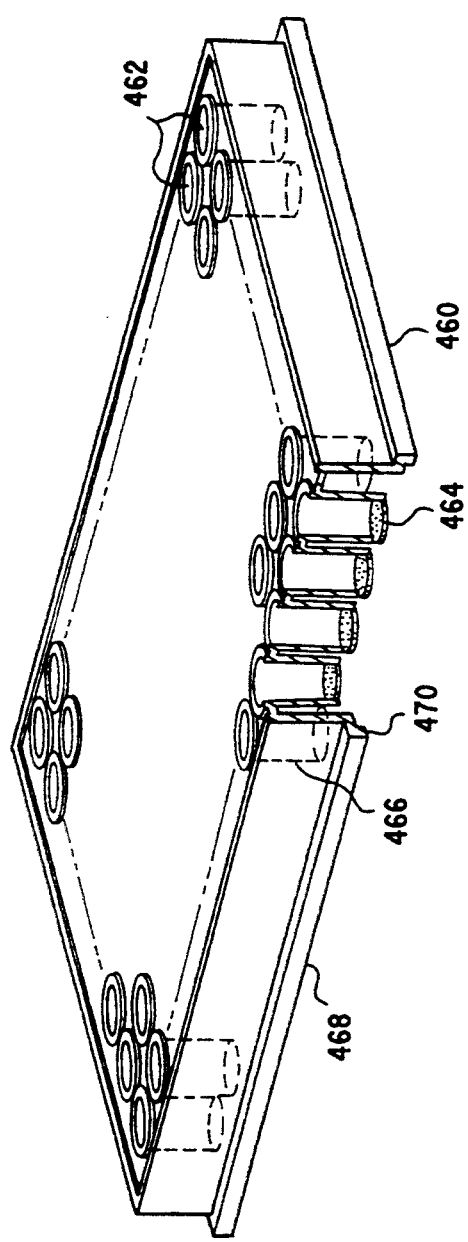
FIG. 52 is a perspective view partly in section of a prior art micro sample well filter plate as may be used in the novel multifunctional filtration apparatus of FIG. 39 of the invention.
Figure 54:
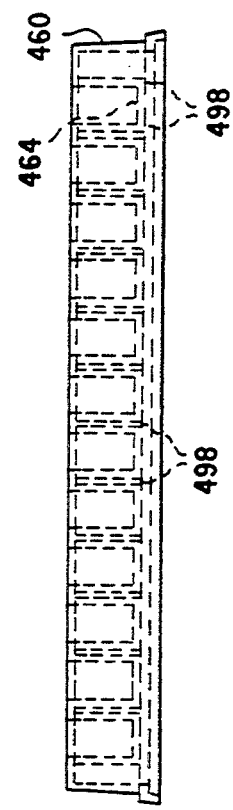
FIG. 54 is a side elevational view partly in phantom of the prior art FIG. 52.
Figure 53:
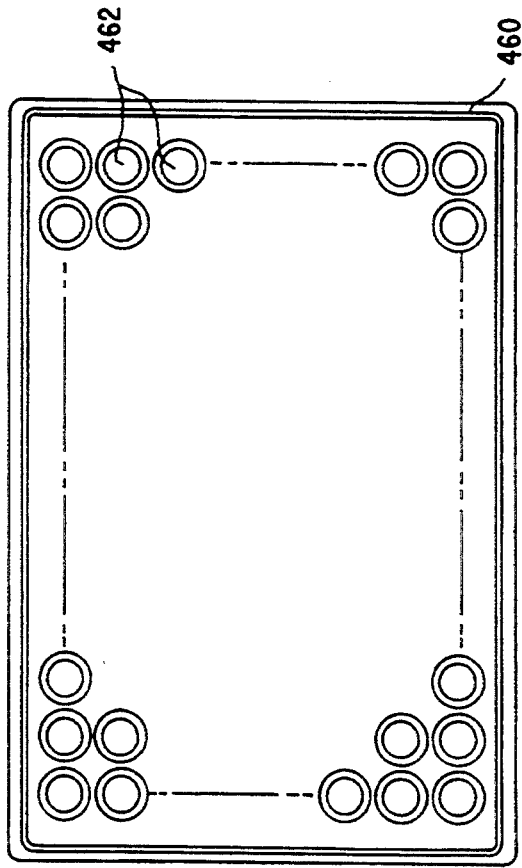
FIG. 53 is a top plan view of the prior art FIG. 52.
Figure 56:
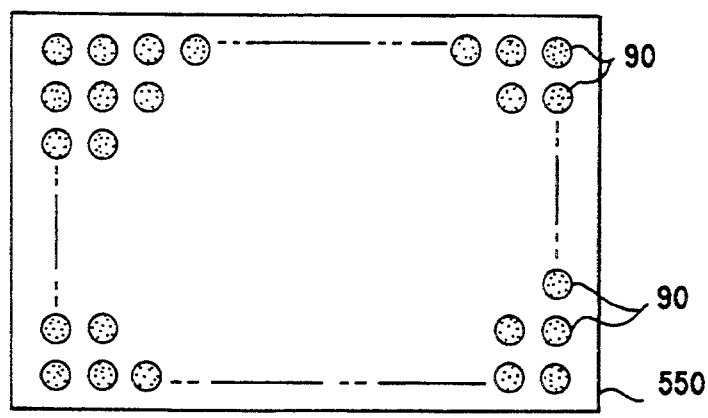
FIG. 56 is a top plan view of FIG. 55.
Figure 57:
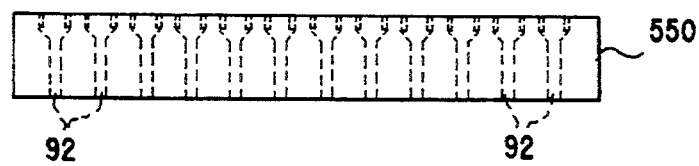
FIG. 57 is a side elevational view partly in phantom of FIG. 55.
Figure 58:
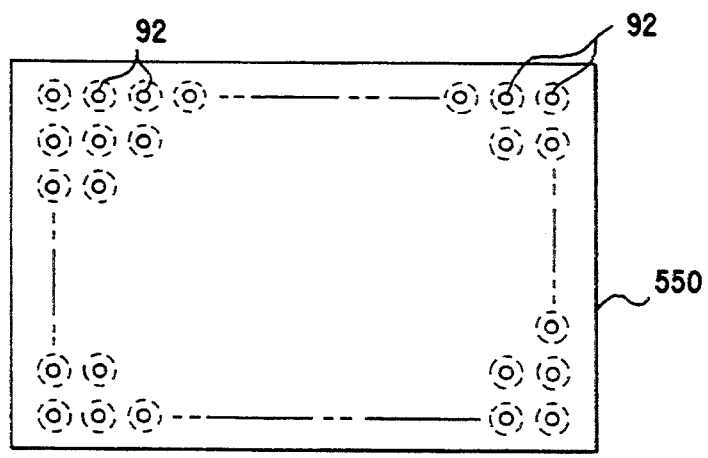
FIG. 58 is a bottom plan view partly in phantom of FIG. 55.
Figure 55:
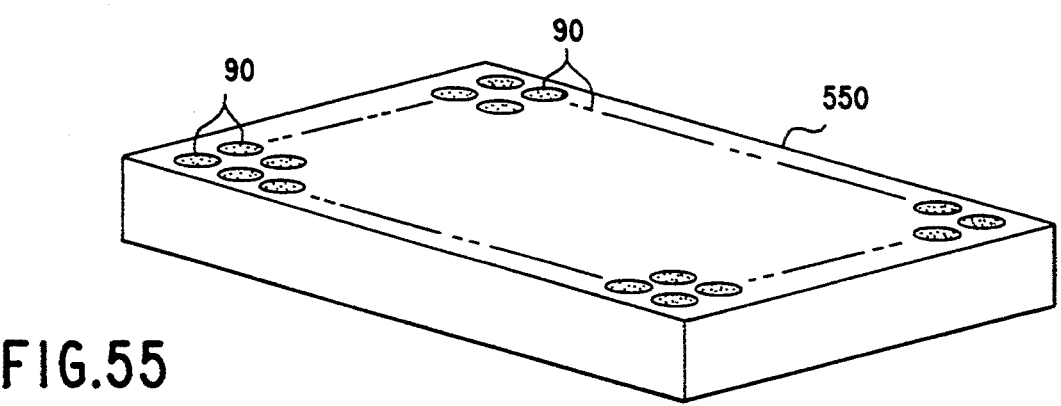
FIG. 55 is a perspective view of an adaptor insert as may be used with the alternative embodiment of multifunctional filtration apparatus as illustrated in FIG. 39.

The micro sample filter plates 460 (FIGS. 52–54) are in most respects similar to the micro sample plate 412 in that they include ninety-six wells made up of eight columns of twelve rows making up the ninety-six openings 462 similar to the micro sample plate 412. The major difference however between micro sample plate 460 and plate 412 resides in the nitrocellulose filters 464 at the bottom of each of the openings 462. The nitrocellulose filters 464 located at the bottom of each of the ninety-six openings 462 have heretofore required the manual transfer and filtration of fluids due to the fragility and aerophobic nature of the filter. The micro sample plate 460 includes a side wall 466 terminating in a ridge 468 providing a supporting surface 470. The features of the micro sample plates with filters 460 are utilized together with recess 490 in modified layer 88 (FIG. 50) to provide for the transfer, separation and filtration of samples from ninety-six small test tubes (FIG. 35) or a micro sample plate 412 (FIG. 37) directly onto micro sample filter plate 460 (FIG. 39) by the modification of layer 88 as illustrated in FIGS. 48–51.

The modification of layer 488 is further illustrated in FIGS. 48, 49, 50 and 51 is similar to layer 88 as previously discussed except modified layer 488 includes a recess 490 of a size sufficient to receive the width of the micro sample plate with filters 464. The recess 490 is of a generally rectangular configuration and includes a further rectangular shaped groove 492 for receiving ridge 468 of sample plate with filters 464. A gasket 494 having holes 491 is placed in recess 490 to provide a seal around each of the filters 464 in the bottom of micro sample plate with filters 464 designed to fit into the opening 492 around the perimeter of the sample plate with filters 460 so that when seated gasket 494 (only a portion of which is shown in FIG. 48) provides a fluid-tight seal between the bottom side 498 of each nitrocellulose bottoms of filters 464 of micro sample plate with filters 460.

The micro sample plate with filters 460 when placed within recess 490 (FIG. 42) and layer 86 is closed over micro sample plate with filters 464 by utilizing hinges 166 and latch hooks 262 a fluid-tight seal exists around each of the individual filters 464 and the gasket 494 so that the bottom sides of filters 464 are in alignment with holes 500 so that activation of the second manifold draws liquid through each of the ninety-six nitrocellulose bottoms of filters 464 and through the ninety-six openings 500 in modified layer 488.

The modified multifunctional filtration apparatus of FIG. 39 operates in the same manner as was previously discussed with respect to FIGS. 35–38 except for the provision for the modified layer 488 and the utilization of micro sample plates with filters 464. The modified layer 488 of FIG. 39 is easily converted to operate on a standard filter medium 260 by utilizing insert 550 which is designed to fill recess 490. Once insert 550 is placed in recess 490 modified layer 488 assumes a configuration similar to layer 88 as illustrated in FIG. 38 so that any filter medium 260 may be placed over insert 88 and modified layer 488 would operate the same as layer 88. Insert 550 as illustrated in FIGS. 55–58 includes 96 openings which may include ninety-six screens or filter support members 90. Insert 550 includes ninety-six channels 92 for alignment with the ninety-six channels 92 in modified layer 488.

The modification of layer 488 along with insert 550 can be further modified by eliminating the second manifold layer 134 by incorporating the second manifold directly into modified layer 488 by utilizing connecting grooves (not shown) to connect the channels 92 in a manner similar to that accomplished with layer 402 (FIG. 42) to create the second manifold in modified layer 488. In such a modification conduit 94 would be attached directly to modified layer thereby entirely eliminating fourth layer 134 since the second manifold 78 would be incorporated directly into layer 88.

In operation the multifunctional filtration apparatus 400 as illustrated in FIGS. 35–37 and 38 utilize the same connections both electrically and vacuum to operate switch 164 and multipositional valve 80 to allow the ninety-six fluid pickup needles to draw fluid from a samples tray 410 or micro sample plate 412 through the ninety-six separate conduits 104 to the ninety-six separate fluid injectors 96 into the ninety-six openings 462 of micro sample plates with filters 464 or on filter member 260. The fluid including liquid, gaseous and filtrable materials deposited in each of the openings 462 of micro sample plate with filter 464 are then separated by utilizing the openings 462 as well as the 96 separation chamber in layer 86 by removing the gaseous components of the fluid through first manifold 72 formed by grooves 310 through conduit 82.

Thereafter when valve 80 is moved from the PRIMARY position to the HARVEST position, second manifold 78 is activated thereby drawing fluids through each of the nitrocellulose bottoms of filters 464 and capturing filtrable materials in nitrocellulose bottoms of filters 464 while fluids are drawn through channels 92 into manifold 78 and removed through conduit 94. Subsequent washings or reactions of materials contained in nitrocellulose bottoms of filters 464 is accomplished in the same manner as heretofore described with respect to the multifunctional filtration apparatus of FIG. 1, FIG. 11, FIG. 18, FIG. 30 and FIG. 34.

The electrical schematic which may be utilized for FIG. 1, FIG. 11, FIG. 18, FIG. 30 and FIG. 34 or any of the embodiments of the multifunctional filtration apparatus of the invention is illustrated in FIGS. 64 and 65. The circuitry as illustrated in FIGS. 62 and 63 may be utilized for a 115 Volt application (FIG. 62) or a 200, 220 or 230 Volt application as illustrated in FIG. 63. The circuitry as illustrated in FIG. 62 and 63 may be utilized for multifunctional filtration apparatus having filtration wells and separation chambers whether one, four, twenty-four, forty-eight, ninety-six, three hundred forty-eight or more and whether or not the number of wells are odd or even.

The electronic circuitry of FIG. 62 and 63 includes power inlet 600 and circuitry 602 for the harvester switch 164 for activating the solenoid valve 120 and includes solenoid valve circuitry 604. A fuse 606 and ON-OFF switch 608 is provided. The circuitry as illustrated in FIGS. 62 and 63 may be modified to suit particular requirements.

Solenoid valve 120 and related circuitry 604 may be removed from the housing of the multifunctional filtration apparatus and attached to the wash pump 118 as may be required in future OSHA regulations which may require the separation of electrical circuitry from the fluid handling components of the invention. Such rearrangement and modification of the electrical components from the fluid components is readily accomplished by those of ordinary skill in the art.

As heretofore discussed the invention may be modified in a number of ways to suit particular requirements for chemical, biochemical and biological testing. As heretofore discussed the filtrate, wash fluids or gaseous products may be collected separately by utilizing separate collection cells or test tubes disposed in the second manifold or disposed downstream from the first or second manifold. In addition the number of separate filtration separation chambers as well as the size of the separation chambers may be increased or decreased to any number whether odd or even utilizing the aspects of the invention which include the provision for a first manifold, a second manifold and a separation chamber disposed therebetween.

The optimal four layers utilized to construct multifunctional filtration apparatus of the invention may also be changed and modified to suit particular requirements for the creation of the first manifold and separation chamber disposed on one side of the filter medium and a second manifold disposed on the other side of the filter medium. The four layers may be reduced to three layers as heretofore described or to only an upper layer providing for the first manifold and separating chamber and a lower layer providing for filter support and a second layer to achieve the advantages of the invention.

The number of individual filtration samples collected on the filter medium furthermore may be rearranged in any pattern, whether rectangular or circular, to suit particular requirements within the contemplation of the invention. The novel invention includes the high speed automated transfer of fluids from individual test tubes or wells in sample tray to a filtration medium where a first manifold connected to a vacuum through a multipositional valve separates liquid from gaseous components and allows for the removal of the gaseous components prior to the separation of liquid components from filtrable components utilizing the second manifold.

The invention not only includes the ability to rapidly transfer and automatedly handle a large number of samples but also allows the samples to be filtered through any type of filter medium, whether the medium is hydrophobic or aerophobic since all gaseous components of the fluid are removed before the liquid and filtrable materials are drawn through the filter medium. In this way gaseous components of the fluid are not available to interfere with either the filter medium or materials captured in the filter medium which might otherwise interfere with the test results or assay by introducing gaseous components to the filter medium or sample contained in the filter medium or destroy the filter medium by rupturing an aerophobic filter medium which would otherwise be impervious to gases.

As discussed the invention is susceptible to a wide number of changes and modifications by those skilled in the art to transfer, separate and filter fluids from one group of containers or test tubes including micro sample plates to any type of filter medium or on to micro sample plate with filters by the modification of the various individual layers or blocks which form the various layers of the multifunctional filtration apparatus. The attachment of the layers to one another as well as the number of layers may be modified by those skilled in the art including the utilization of quick-release layers or fasteners for quickly attaching and removing layers to result in the quick and rapid change-over from one type of sample, i.e. test tubes to filter plate or the utilization of collection vessels in the first or second manifold. These and other applications of the invention are contemplated utilizing the first manifold, second manifold and separation chamber in combination with a multipositional valve in accordance with the invention. These and other such modifications of the invention are contemplated by those skilled in the art and are intended to be included within the scope of the following claims.

What is claimed is:

1. A multifunctional filtration apparatus comprising:
   (a) a first manifold;
   (b) a second manifold;
   (c) a separation chamber disposed between said first manifold and said second manifold;
   (d) a filter support disposed between said separation chamber and said second manifold; and
   (e) a valve having a vacuum inlet and a first outlet and a second outlet, said first outlet operatively connected to said first manifold or said separation chamber and said second outlet operatively connected to said second manifold.

2. The multifunctional filtration apparatus of claim 1 further comprising an injector having one end disposed outside said first manifold and the other end disposed in said separation chamber for injecting fluids in said separation chamber.

3. The multifunctional filtration apparatus of claim 2 wherein said injector extends from about 25 to 90 percent of the length of said separation chamber.

4. The multifunctional filtration apparatus of claim 2 further comprising a fluid pick up needle operatively connected to said injector.

5. The multifunctional filtration apparatus of claim 4 further comprising a wash or reagent addition needle operatively connected to a wash manifold for adding wash or reagent fluids wherein said wash or reagent addition needle is in a distanced relationship to said fluid pick up needle.

6. The multifunctional filtration apparatus of claim 5 further comprising a purge conduit operatively connected to said wash manifold and said valve.

7. The multifunctional filtration apparatus of claim 6 further comprising a pump for pumping wash or reagent fluids to said wash manifold.

8. The multifunctional filtration apparatus of claim 1 wherein said separation chamber is divided into a plurality of separation chambers.

9. The multifunctional filtration apparatus of claim 8 wherein said plurality of separation chambers is at least four.

10. The multifunctional filtration apparatus of claim 8 wherein said plurality of separation chambers is at least twenty-four.

11. The multifunctional filtration apparatus of claim 8 wherein said plurality of separation chambers is at least forty-eight.

12. The multifunctional filtration apparatus of claim 8 wherein said plurality of separation chambers is at least ninety-six.

13. The multifunctional filtration apparatus of claim 8 wherein said plurality of separation chambers is at least three hundred eighty-four.

14. The multifunctional filtration apparatus of claim 1 wherein said valve includes means for selectively connecting said vacuum inlet with said first outlet and said second outlet.

15. The multifunctional filtration apparatus of claim 14 further comprising an injector for injecting fluids having one end disposed outside said first manifold and the other end disposed in said separation chamber.

16. The multifunctional filtration apparatus of claim 15 wherein said injector extends from about 25 to 90 percent of the length of said separation chamber.

17. The multifunctional filtration apparatus of claim 14 further comprising a fluid pick up needle operatively connected to said injector.

18. The multifunctional filtration apparatus of claim 17 further comprising a wash manifold operatively connected to a fluid addition needle wherein said fluid addition needle is in a distanced relationship to said fluid pick up needle.

19. The multifunctional filtration apparatus of claim 18 further comprising a purge conduit operatively connected to said wash manifold and said valve.

20. The multifunctional filtration apparatus of claim 19 further comprising a pump for pumping fluids to said wash manifold.

21. The multifunctional filtration apparatus of claim 20 wherein said separation chamber is divided into a plurality of separation chambers and said injector is divided into a plurality of injectors and said fluid pick up needle is divided into a plurality of fluid pick up needles and said fluid addition needle is divided into a plurality of fluid addition needles.

22. The multifunctional filtration apparatus of claim 21 wherein said plurality of separation chambers is at least four and said plurality of injectors is at least four and said plurality of fluid pick up needles is at least four and said plurality of fluid addition needles is at least four.

23. The multifunctional filtration apparatus of claim 21 wherein said plurality of separation chambers is at least twenty-four and said plurality of injectors is at least twenty-four and said plurality of fluid pick up needles is at least twenty-four and said plurality of fluid addition needles is at least twenty-four.

24. The multifunctional filtration apparatus of claim 21 wherein said plurality of separation chambers is at least forty-eight and said plurality of injectors is at least forty-eight and said plurality of pick up needles is at least forty-eight and said plurality of fluid addition needles is at least forty-eight.

25. The multifunctional filtration apparatus of claim 21 wherein said plurality of separation chambers is at least ninety-six and said plurality of injectors is at least ninety-six and said plurality of pick up needles is at least ninety-six and said plurality of fluid addition needles is at least ninety-six.

26. A filtration apparatus for transferring and filtering fluids comprising:
 (a) a first layer having a first manifold and a separation chamber;
 (b) a second layer having a filter support and a second manifold;
 (c) means for detachably joining said first layer to said second layer; and
 (d) a valve having a vacuum inlet and a first outlet and a second outlet, said first outlet operatively connected to said first layer and said second outlet operatively connected to said second layer.

27. The filtration apparatus for transferring and filtering fluids of claim 26 further comprising an injector in said first layer for injecting fluid in said separation chamber.

28. The filtration apparatus for transferring and filtering fluids of claim 27 further comprising a plurality of fluid pick up needles operatively connected to a plurality of injectors.

29. The filtration apparatus for transferring and filtering fluids of claim 28 further comprising a wash manifold operatively connected to a plurality of wash addition needles wherein said wash addition needles are in a distanced relationship to said fluid pick up needles.

30. The filtration apparatus for transferring and filtering fluids of claim 29 further comprising a purge conduit operatively connected to said wash manifold and said valve.

31. The filtration apparatus for transferring and filtering fluids of claim 30 further comprising a wash manifold valve and a solenoid for opening and closing said wash manifold valve.

32. The filtration apparatus for transferring and filtering fluids of claim 30 further comprising a support structure for holding said fluid pick up needles and said wash addition needles in a distanced relationship to one another.

33. The filtration apparatus for transferring and filtering fluids of claim 30 wherein said filter support and said second manifold are separable from each other in said second layer.

34. The filtration apparatus for transferring and filtering fluids of claim 33 further comprising a liquid injector disposed in said filter support for injecting liquids into said second manifold.

35. The filtration apparatus for transferring and filtering fluids of claim 34 wherein said second manifold includes means for collecting liquids injected in said second manifold from said liquid injector.

36. The filtration apparatus for transferring and filtering fluids of claim 30 further comprising means for providing said vacuum inlet of said valve simultaneous access to said first outlet and said second outlet.

37. The filtration apparatus for transferring and filtering fluids of claim 36 wherein said simultaneous access to said first outlet can provide a vacuum pressure $P_1$ and said simultaneous access to said second outlet can provide a vacuum pressure $P_2$ wherein said vacuum pressure $P_2$ is greater than said vacuum pressure $P_1$.

38. The filtration apparatus for transferring and filtering fluids of claim 36 wherein said valve includes a second vacuum inlet and means for connecting said vacuum inlet with said first outlet and said second vacuum inlet and said second outlet.

39. The filtration apparatus for transferring and filtering fluids of claim 30 wherein said second layer includes a sample tray recess.

40. The filtration apparatus for transferring and filtering fluids of claim 39 further comprising a filter support insert for filling said sample tray recess.

41. The filtration apparatus for transferring and filtering fluids of claim 30 wherein said separation chamber in said first layer is divided into a plurality of separation chambers.

42. The filtration apparatus for transferring and filtering fluids of claim 41 further comprising a plurality of wash addition needles, a plurality of fluid pick up needles and a plurality of injectors.

43. The filtration apparatus for transferring and filtering fluids of claim 42 wherein said plurality of separation chambers are at least twenty-four and said plurality of wash addition needles are at least twenty-four and said plurality of fluid pick up needles are at least twenty-four and said plurality of injectors is at least twenty-four.

44. The filtration apparatus for transferring and filtering fluids of claim 42 wherein said plurality of separation chambers are at least forty-eight and said plurality of wash addition needles are at least forty-eight and said plurality of fluid pick up needles are at least forty-eight and said plurality of injectors is at least forty-eight.

45. The filtration apparatus for transferring and filtering fluids of claim 44 wherein said second layer includes a forty-eight well sample tray recess.

46. The filtration apparatus for transferring and filtering fluids of claim 42 wherein said plurality of separation chambers are at least ninety-six and said plurality of wash addition needles are at least ninety-six and said plurality of fluid pick up needles are at least ninety-six and said plurality of injectors is at least ninety-six.

47. The filtration apparatus for transferring and filtering fluids of claim 46 wherein said second layer includes a ninety-six well sample tray recess.

48. A filtration apparatus for filtering through all types of filter mediums comprising:
 (a) a first layer having a first manifold;
 (b) a second layer having a separation chamber;
 (c) a third layer providing a filter support medium;
 (d) a fourth layer having a second manifold;
 (e) means for detachably opening and closing said second layer with respect to said third layer; and
 (f) a valve having a vacuum inlet and a first outlet and a second outlet, said first outlet operatively connected to said first layer and said second outlet operatively connected to said fourth layer.

49. The filtration apparatus for filtering through all types of filter mediums of claim 48 further comprising an injector having one end disposed outside said first layer and the other end disposed in said separation chamber.

50. The filtration apparatus for filtering through all types of filter mediums of claim 49 further comprising a fluid pick up needle operatively connected to said injector.

51. The filtration apparatus for filtering through all types of filter mediums of claim 50 further comprising a wash manifold operatively connected to a wash addition needle wherein said wash addition needle is in a distanced relationship to said fluid pick up needle.

52. The filtration apparatus for filtering through all types of filter mediums of claim 51 further comprising a purge conduit operatively connected to said wash manifold and said valve.

53. The filtration apparatus for filtering through all types of filter mediums of claim 52 further comprising a housing for holding a plurality of fluid pick up needles and a plurality of wash addition needles in a distanced relationship to one another.

54. The filtration apparatus for filtering through all types of filter mediums of claim 53 wherein said third layer and said fourth layer include means for detachably opening and closing said third layer and said fourth layer.

55. The filtration apparatus for filtering through all types of filter mediums of claim 53 wherein said third layer includes a sample tray recess.

56. The filtration apparatus for filtering through all types of filter mediums of claim 55 further comprising a filter support insert for filling said sample tray recess.

57. The filtration apparatus for filtering through all types of filter mediums of claim 53 wherein said separation chamber in said second layer is divided into a plurality of separation chambers.

58. The filtration apparatus for filtering through all types of filter mediums of claim 57 further comprising a plurality of wash addition needles, a plurality of fluid pick up needles and a plurality of injectors.

59. The filtration apparatus for filtering through all types of filter mediums of claim 58 wherein said plurality of separation chambers are at least twenty-four and said plurality of wash addition needles are at least twenty-four and said plurality of fluid pick up needles are at least twenty-four and said plurality of injectors is at least twenty-four.

60. The filtration apparatus for filtering through all types of filter mediums of claim 58 wherein said plurality of separation chambers are at least forty-eight and said plurality of wash addition needles are at least forty-eight and said plurality of fluid pick up needles are at least forty-eight and said plurality of injectors is at least forty-eight.

61. The filtration apparatus for filtering through all types of filter mediums of claim 60 wherein said second layer includes a forty-eight well sample tray recess.

62. The filtration apparatus for filtering through all types of filter mediums of claim 58 wherein said plurality of separation chambers are at least ninety-six and said plurality of wash addition needles are at least ninety-six and said plurality of fluid pick up needles are at least ninety-six and said plurality of injectors is at least ninety-six.

63. The filtration apparatus for filtering through all types of filter mediums of claim 62 wherein said second layer includes a ninety-six well sample tray recess.

* * * * *